(12) United States Patent
Bornhop

(10) Patent No.: US 8,445,217 B2
(45) Date of Patent: May 21, 2013

(54) FREE SOLUTION MEASUREMENT OF MOLECULAR INTERACTIONS BY BACKSCATTERING INTERFEROMETRY

(75) Inventor: Darryl J. Bornhop, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 12/674,610

(22) PCT Filed: Sep. 20, 2008

(86) PCT No.: PCT/US2008/077145
§ 371 (c)(1),
(2), (4) Date: Oct. 4, 2011

(87) PCT Pub. No.: WO2009/039466
PCT Pub. Date: Mar. 26, 2009

(65) Prior Publication Data
US 2012/0015376 A1    Jan. 19, 2012

Related U.S. Application Data

(60) Provisional application No. 60/973,829, filed on Sep. 20, 2007.

(51) Int. Cl.
*G01N 33/53* (2006.01)
(52) U.S. Cl.
USPC .................................................... 435/7.2
(58) Field of Classification Search
None
See application file for complete search history.

(56) References Cited

U.S. PATENT DOCUMENTS

| 4,895,431 A | 1/1990 | Tsujiuchi et al. |
| 4,976,154 A | 12/1990 | Schneider et al. |

(Continued)

FOREIGN PATENT DOCUMENTS

| EP | 1746385 A1 | 1/2007 |
| FR | 2 766 922 A | 2/1999 |

(Continued)

OTHER PUBLICATIONS

Abato, et al., "An enzymatic method for determining enantiomeric excess," *J Am Chem Soc*, 123:9206-9207 (2001).

(Continued)

*Primary Examiner* — N. C. Yang
*Assistant Examiner* — Richard Moerschell
(74) *Attorney, Agent, or Firm* — Ballard Spahr LLP

(57) ABSTRACT

Disclosed are methods, systems, and apparatuses for the free solution measurement of molecular interactions by backscattering interferometry (BSI). Molecular interaction can be detected between analytes in free-solution wherein at least one of the analytes is label-free and detection is performed by back-scattering interferometry. Further, molecular interaction can be detected between analytes in free-solution, wherein at least one of the analytes is label-free, wherein one of the analytes is present in a concentration of less than about $5.0 \times 10^{-7}$ M. Also disclosed are label-free, free-solution, and/or real-time measurements of characteristic properties and/or chemical events using the disclosed techniques. The disclosed methods can have very low detection limits and/or very low sample volume requirements. Also disclosed are various biosensor applications of the disclosed techniques. This abstract is intended as a scanning tool for purposes of searching in the particular art and is not intended to be limiting of the present invention.

22 Claims, 21 Drawing Sheets

U.S. PATENT DOCUMENTS

| | | | |
|---|---|---|---|
| 4,990,925 A | 2/1991 | Edelsohn et al. | |
| 5,073,024 A | 12/1991 | Valette et al. | |
| 5,120,131 A | 6/1992 | Lukosz | 356/351 |
| 5,273,633 A | 12/1993 | Wang et al. | |
| 5,325,170 A | 6/1994 | Bornhop | 356/128 |
| 5,479,257 A | 12/1995 | Hashimoto | |
| 5,485,312 A | 1/1996 | Horner et al. | |
| 5,502,561 A | 3/1996 | Hutchins | 356/336 |
| 5,613,013 A | 3/1997 | Schuette | |
| 5,659,318 A | 8/1997 | Madsen et al. | |
| 5,698,518 A * | 12/1997 | Carson et al. | 514/9.7 |
| 5,781,304 A | 7/1998 | Kotidis et al. | |
| 5,804,453 A | 9/1998 | Chen | |
| 5,817,462 A | 10/1998 | Garini et al. | |
| 5,915,034 A | 6/1999 | Nakajima et al. | |
| 5,953,439 A | 9/1999 | Ishihara et al. | |
| 5,995,645 A | 11/1999 | Soenksen et al. | |
| 6,108,458 A | 8/2000 | Hart | |
| 6,198,532 B1 | 3/2001 | Cabib et al. | |
| 6,381,025 B1 | 4/2002 | Bornhop et al. | 356/517 |
| 6,480,282 B1 * | 11/2002 | Chinowsky et al. | 356/445 |
| 6,493,090 B1 | 12/2002 | Lading et al. | 356/484 |
| 6,529,279 B2 | 3/2003 | De Groot et al. | |
| 6,532,061 B2 | 3/2003 | Ortyn et al. | |
| 6,533,914 B1 | 3/2003 | Liu | 204/601 |
| 6,576,430 B1 * | 6/2003 | Hsieh et al. | 435/7.1 |
| 6,741,361 B2 | 5/2004 | Marron | |
| 6,744,950 B2 | 6/2004 | Aleksoff | |
| 6,798,509 B2 | 9/2004 | Sonehara et al. | |
| 6,809,828 B2 * | 10/2004 | Bornhop et al. | 356/517 |
| 6,980,299 B1 | 12/2005 | de Boer | |
| 7,130,060 B2 | 10/2006 | Bornhop et al. | 356/517 |
| 7,173,986 B2 | 2/2007 | Wu | 375/343 |
| 7,202,076 B2 | 4/2007 | Cunningham et al. | |
| 7,300,803 B2 | 11/2007 | Lin et al. | |
| 2002/0022603 A1 * | 2/2002 | Lichtenberger | 514/78 |
| 2004/0058058 A1 | 3/2004 | Shchegolikhin et al. | |
| 2004/0218184 A1 * | 11/2004 | Jorgenson et al. | 356/419 |
| 2005/0014179 A1 * | 1/2005 | Karlsson et al. | 435/6 |
| 2005/0190372 A1 | 9/2005 | Dogariu | |
| 2005/0227374 A1 | 10/2005 | Cunningham | |
| 2005/0244863 A1 | 11/2005 | Mir | |
| 2006/0012800 A1 | 1/2006 | Bornhop et al. | 356/517 |
| 2006/0039004 A1 | 2/2006 | De Boer et al. | |
| 2006/0256343 A1 | 11/2006 | Choma et al. | |
| 2006/0275179 A1 * | 12/2006 | Viovy et al. | 422/100 |
| 2007/0054339 A1 | 3/2007 | Lin et al. | |

FOREIGN PATENT DOCUMENTS

| | | |
|---|---|---|
| WO | WO 01/14858 | 3/2001 |
| WO | WO 02/059579 * | 8/2002 |
| WO | WO 2004/023115 | 3/2004 |
| WO | WO 2007/002178 | 1/2007 |

OTHER PUBLICATIONS

Adányi et al., "Development of immunosensor based on OWLS technique for determining Aflatoxin B1 and Ochratoxin A," *Biosens Bioelectron* 22:797-802 (2007).

Alunni, et al., "Mechanisms of inhibition of phenylalanine ammonialyase by phenol inhibitors and phenol/glycine synergistic inhibitors," *Arch Biochem and Biophys* 412(2):170-175 (2003).

Anderson, et al., "Fabrication of topologically complex three-dimensional microfluidic systems in PDMS by rapid prototyping," *Anal Chem* 72(14):3158-64 (2000).

Andersson et al., "TV shearography: quantitative measurement of shear-magnitude fields by use of digital speckle photography," Applied Optics, vol. 39:2565 (2000).

Anuta, "Digital Registration of Multispectral Video Imagery," Society of Photo-optical Instrumentation Engineers Journal, vol. 7:168 (1969).

Arnold, "Design by directed evolution," *Accounts Chem Res* 31(3):125-131 (1998).

Bobbitt, et al., "Direct and Indirect Polarimetry for Detection in Microbore Liquid-Chromatography," *Anal Chem* 56:1577-1581 (1984).

Borman, "Combinatorial chemistry," *Chem & Eng News* vol. 80 No. 45:43-57 (2002).

Bornhop, "Microvolume index of refraction determinations by interferometric backscatter," *Applied Optics*, vol. 34:3234-39 (1995).

Bornhop, et al., "Free-Solution, Label-Free Molecular Interactions Studied by Back-Scattering Interferometry," *Science*, vol. 317 No. 5485:1732-1736 (2007).

Bornhop, et al., "Polarimetry in capillary dimensions," *Anal Chem* 68:1677-1684 (1996).

Bouchara, "Efficient algorithm for computation of the second-order moment of the subpixel-edge position," Applied Optics, vol. 43:4550 (2004).

Brawer, et al., "Screening for prostatic carcinoma with prostate specific antigen," *J. Urol.*, 147:841-845 (1992).

Brenan, et al., "High throughput, nanoliter quantitative PCR," *Drug Discovery Today: Tech*, 2:247-253 (2005).

Brockhaus et al., "Thermadynamic studies on the interaction of antibodies with β-amyloid peptide," *J Phys Chem B*, 111:1238-43 (2007).

Brockman et al., "A Multistep Chemical Modification Procedure to Create DNA Arrays on Gold Surfaces for the Study of Protein—DNA Interactions with Surface Plasmon Resonance Imaging," *J Am Chem Soc*, vol. 121 issue 35:8044-8051 (1999).

Burke et al., "Stopped-flow enzyme assays on a chip using a microfabricated mixer," *Anal Chem*, 75(8):1786-1791 (2003).

Campitelli et al., "Shear horizontal surface acoustic wave based immunosensing system," *Int Conf on Solid State Sensors and Actuators*, Jun. 16-19, 1:187-190 (1997).

Choquette et al., "Wavenumber Standards for Near-infrared Spectrometry," Handbook of Vibrational Spectroscopy, John M. Chalmers and Peter R. Griffiths (Editors), 2002, p. 1-7.

Cohen, et al., "In vitro enzyme evolution: the screening challenge of isolating the one in a million," *Trends in Biotechnol*, 19:507-510 (2001).

Collignon et al., "Automated multimodality image registration based on information theory", Information Processing in Medical Imaging (Y. Bizais, C. Barillot and R. Di Paola, eds.), Kluwer Academic Publishers, Dordrecht, pp. 263-274, 1995.

Duffy et al., "Rapid prototyping of microfluidic systems in poly(dimethylsiloxane)," *Anal Chem*, 70:4974-4984 (1998).

Fan, et al., "Electrochemical interrogation of conformational changes as a reagentless method for the sequence-specific detection of DNA" *Proc Natl Acad Sci U S A*, 100(16): 9134-9137 (2003).

Finn, "Emerging methods for the rapid determination of enantiomeric excess," *Chirality*, 14:534-540 (2002).

Fox, et al., "Assay Innovations Vital to Improving HTS," *Drug Discovery and Development*, Mar. 2000:40-43.

Fricke-Begemann et al., "Speckle interferometry: three-dimensional deformation field measurement with a single interferogram," Applied Optics, vol. 40:5011 (2001).

Gibbs, et al., "Imaging polarimetry for high throughput chiral screening," *Biotech Progress*, 19:1329-1334 (2003).

Gloge, et al., "The behavior of substrate analogues and secondary deuterium isotope effects in the phenylalanine ammonia-lyase reaction," *Arch of Biochem and Biophys*, 359:1-7 (1998).

Gloge, et al., "Phenylalanine ammonia-lyase: The use of its broad substrate specificity for mechanistic investigations and biocatalysis—Synthesis of L-arylalanines," *Chemistry—A European Journal*, vol. 6, issue 18:3386-3390 (2000).

Grant No. R01 EB003537-01A2 awarded by National Institutes of Health.

Greisen, et al., "PCR primers and probes for the 16S rRNA gene of most species of pathogenic bacteria, including bacteria found in cerebrospinal fluid," *J Clin Microbiol*, 32:335-351 (1994).

Grosse, et al., "Deep wet etching of fused silica glass for hollow capillary optical leaky waveguides in microfluidic devices," *J Micromech and Microeng*, 11:257-262 (2001).

Guizar-Sicairos et al., "Efficient subpixel image registration algorithms," Optics Letters, vol. 33:156-158 (2008).

Guo, et al., "Measurement of enantiomeric excess by kinetic resolution and mass spectrometry," *Angew Chem Int Ed*, 38:1755-1758 (1998).

Harrison, et al., "Capillary Electrophoresis and Sample Injection Systems Integrated on a Planar Glass Chip," *Anal Chem*, 64(17):1926-1932 (1992).

Harteveld et al., "Detection of Staphylococcal Enterotoxin B employing a piezoelectric crystal immunosensor," *Biosens Bioelectron* 12(7):661-667 (1997).

Hodgins, "Yeast Phenylalanine Ammonia-Lyase—Purification, Properties, and Identification of Catalytically Essential Dehydroalanine," *J Biol Chem*, 246(9):2977-85 (1971).

Hofstetter, et al., "Antibodies as chiral selectors for the determination of enantioenrichment," *Enantiomer*, 6:153-158 (2001).

Horton et al., "Interference patterns of a plane-polarized wave from a hollow glass fiber," *J Opt Soc Am*, 63:1204-1210 (1973).

Hubbard et al., "Calmodulin binding by calcineurin," *J Biol Chem* 262(31):15062-15070 (1987).

Huntley, "Speckle photography fringe analysis: assessment of current algorithms," Applied Optics, vol. 28:4316 (1989).

Jacobson, et al., "Fused Quartz Substrates for Microchip Electrophoresis," *Anal Chem*, 67:2059-2063 (1995).

Jacobson, et al., "Microfluidic devices for electrokinetically driven parallel and serial mixing," *Anal Chem*, 71:4455-4459 (1999).

Kalghatgi, et al., "Microbial L-phenylalanine ammonia-lyase. Purification, subunit structure and kinetic properties of the enzyme from *Rhizoctonia solani*," *Biochem J*, 149:65-75 (1975).

Kalinina, et al., "Nanoliter scale PCR with TaqMan detection," *Nucleic Acid Research*, 25(10):1999-2004 (1997).

Kerker, et al., "Scattering of Electromagnetic Waves from Concentric InfiniteCylinders," *J Opt Soc Am*, 51:506-508 (1961).

Klee et al., "Purification of cyclic 3',5'-nucleotide phosphodiesterase inhibitory protein by affinity chromatography on activator protein couples to sepharose," *Biochem* 17:120-126 (1978).

Korbel, et al., "Reaction microarrays: A method for rapidly determining the enantiomeric excess of thousands of samples,"*J Am Chem Soc*, 123(2):361-362 (2001).

Kuhlmann, "Drug Research: From the Idea to the Product," Int J Clin Pharmacol Ther, 35(12):541-552 (1997).

Lan et al., "Non-mechanical sub-pixel image shifter for acquiring super-resolution digital images," Optics Express, vol. 17:22992-23002 (2009).

Langone, "Protein A of *Staphylococcus aureus* and related immunoglobulin receptors produced by streptococci and pneumonococci," *Adv Immunol*, 32:157-252 (1982).

Latham et al., "Photobiotin surface chemistry improves label-free interferometric sensing of biochemical interactions," *Angew Chem Int Ed*, 45:955-958 (2006).

Liu, et al., "Optimization of high-speed DNA sequencing on microfabricated capillary electrophoresis channels," *Anal Chem*, 71:566-573 (1999).

Manz, et al., "Micromachining of Monocrystalline Silicon and Glass for Chemical-Analysis Systems—a Look into Next Century Technology or Just a Fashionable Craze?," *Trac-Trends in Anal Chem*, 10(5):144-149 (1991).

Manz, et al., "Miniaturized Total Chemical-Analysis Systems—a Novel Concept for Chemical Sensing," *Sensors and Actuators B:Chemical*, 1:244-248 (1990).

Marcuse et al., "Light scattering from optical fibers with arbitrary refractive-index distributions," *J Opt Soc Am*, 65:367-375 (1975).

Markov, et al., "Breaking the 10-7 Barrier for RI Measurements in Nanoliter Volumes," Anal Chem, 74:5438-5441 (2002).

Markov et al., "A fourier analysis approach for capillary polarimetry," *Electrophoresis*, 23:809-812 (2002).

Markov et al., "Label-Free Molecular Interaction Determinations with Nanoscale Interferometry," *J Am Chem Soc* 126:16659-16664 (2004).

Markov, et al., "Non-Invasive Fluid Flow Measurements in Microfluidic Channels with Backscatter Interferometry," *Electrophoresis*, 25(21-22):3805-3809 (2004).

Martynova, et al., "Fabrication of plastic microfluid channels by imprinting methods," *Anal Chem*, 69:4783-4789 (1997).

May, et al., "Inverting enantioselectivity by directed evolution of hydantoinase for improved production of L-methionine," *Nat Biotech*, 18(3):317-320 (2000).

Maystre, et al., "Enhanced Polarimetric Detection in Hplc Using a Refractive-Index Equalizer," *Anal Chem*, 66:2882-2887 (1994).

Miroshnikova et al., "Percussion hole drilling of metals with a fourth-harmonic Nd:YAG laser studied by defocused laser speckle correlation," Applied Optics, vol. 44:3403 (2005).

Montigiani et al., "Alanine substitutions on calmodulin-binding peptides result in unexpected affinity enhancement," *J Mol Biol* 258:6-13 (1996).

Morrison, et al., "Nanoliter high throughput quantitative PCR," *Nucleic Acid Res*, 34(18):e123 (2004).

Neifeld, "Information, resolution, and space—bandwidth product," Optics Letters, vol. 23:1477-1479 (1998).

Pitter et al., "Focus errors and their correction in microscopic deformation analysis using correlation," Optics Express, vol. 10:1361-1367 (2002).

Quake, et al., "From micro- to nanofabrication with soft materials," *Science*, 290:1536-1540 (2000).

Read, et al., "Aseptic meningitis and encephalitis: the role of PCR in the diagnostic laboratory," *Clin Microbiol*, 35:691-696 (1997).

Reem et al, "Induction and upregulation by interleukin 2 of high-affinity interleukin 2 receptors on thymocytes and T cells," *Proc Natl Acad Sci USA*, 82:8663-8666 (1985).

Reetz, "Combinatorial and evolution-based methods in the creation of enantioselective catalysts," *Angew Chem Int Ed*, 40:284-310 (2001).

Reetz, "New methods for the high-throughput screening of enantioselective catalysts and biocatalysts," *Angew Chem Int Ed*, 41:1335-1338 (2002).

Resetar, et al., "Anticipating Technological Change: Combinatorial Chemistry and the Environment," *EPA*, 2001.

Rich et al., "High-resolution and high-throughput protocols for measuring drug/human serum albumin interactions using BIACORE," *Anal Biochem* 296:197- 207 (2001).

Rother, et al., "An active site homology model of phenylalanine ammonia-lyase from *Petroselinum crispum*," *Eu J Biochem*, 269:3065-3075 (2002).

Rouhi, "Chiral chemistry," *Chem Eng News*, 82(24):47-62 (2004).

Rouhi, "Chiral roundup—As pharmaceutical companies face bleak prospects, their suppliers diligently tend the fertile fields of chiral chemistry in varied ways," *Chem Eng News*, 80(23):43-50 (2002).

Rouhi, "Chiral roundup—Taking a measure of chiral riches—Researchers respond to high demand for ways to measure enantioenrichment quickly," *Chem Eng News*, 80(23):51-57 (2002).

Saha et al., "Comparative study of IgG binding to proteins G and A: Nonequilibrium kinetic and binding constant determination with the acoustic waveguide device," *Anal Chem*, 75:835-842 (2003).

Schonfeld, et al., "Polarimetric assay for the medium-throughput determination of alpha-amino acid racemase activity," *Anal Chem*, 76:1184-1188 (2004).

Schuster, et al., "The Mechanism of Action of Phenylalanine Ammonia-Lyase—the Role of Prosthetic Dehydroalanine,"*Proc Natl Acad Sci USA*, 92(18):8433-8437 (1995).

Sidick et al., "Adaptive cross-correlation algorithm for extended scene Shack—Hartmann wavefront sensing," Optics Letters, vol. 33:213-215 (2008).

Sjodahl, "Accuracy in electronic speckle photography," Applied Optics, vol. 36:2875-2885 (1997).

Sjodahl et al., "Electronic speckle photography: analysis of an algorithm giving the displacement with subpixel accuracy," Applied Optics, vol. 32:2278-2284 (1993).

Sjodahl, "Electronic speckle photography: increased accuracy by nonintegral pixel shifting," Applied Optics, vol. 33:6667-6673 (1994).

Sjodahl et al., "Measurement of shape by using projected random patterns and temporal digital speckle photography," Applied Optics, vol. 38:1990-1997 (1999).

Soumet, et al., "Identification by a multiplex PCR-based assay of *Salmonella typhimurium* and *Salmonella enteritidis* strains from environmental swabs of poultry houses ," *Lett Appl Microbiol*, 29(1) 1-6 (1999).

Speaker, et al., "Characterization of a calmodulin-binding protein that is deficient in trifluoperazine-resistant variants of the macrophage-like cell line J774," *Proc Natl Acad Sci USA*, 80:329-333 (1983).

Svanbro et al., "Complex amplitude correlation for compensation of large in-plane motion in digital speckle pattern interferometry," Applied Optics, vol. 45:8641-8647 (2006).
Swinney, et al., "Capillary-scale polarimetry for flowing streams," Analyst, 126:673-675 (2001).
Swinney, et al., "Chip-scale universal detection based on backscatter interferometry," Anal Chem, 72:2690-2695 (2000).
Swinney, et al., "A chip-scale universal detector for electrophoresis based on backscattering Interferometry," Analyst, 125:1713-1717 (2000).
Swinney, et al., "D-beta-Hydroxybutyrate reaction kinetics studied in nanoliter volumes using a capillary polarimeter," Applied Spectroscopy 54:1485-1489 (2000).
Swinney, et al., "Micro-interferometric backscatter detection using a diode laser," Analytica Chimica Acta, 400:265-280 (1999).
Swinney, et al., "Nanoliter volume polarimetry," Applied Spectroscopy, 56:134-138 (2002).
Swinney, et al., "Noninvasive picoliter volume thermometry based on backscatter Interferometry," Electrophoresis, 22(1):2032-2036 (2001).
Swinney, et al., "Quantification and evaluation of Joule heating in on-chip capillary electrophoresis," Electrophoresis, 23(4):613-620 (2002).
Swinney, et al., "Ultrasmall volume refractive index detection using microinterferometry," Rev Sci Instrum 71:2684-2692 (2000).
Synnergren et al., "Application of digital speckle photography to flash x-ray studies of internal deformation fields in impact experiments," Applied Optics, vol. 36:4030-4036 (1999).
Synnergren et al., "Digital speckle photography: visualization of mesoflow through clustered fiber networks," Applied Optics, vol. 41:1368-1373 (2002).
Synnergren et al. "Optical in-plane strain field sensor," Applied Optics, vol. 41:1323-1329 (2002).
Takushima et al., "Optical reflectometry based on correlation detection and its application to the in-service monitoring of WDM passive optical network," Optics Express, vol. 15:5318-5326 (2007).
Tan, et al., "Rapid fabrication of microfluidic devices in poly(dimethylsiloxane) by photocopying," Lab on a Chip, 1:7-9 (2001).
Tarigan et al., "Capillary-scale refractive index detection by interferometric backscatter," Anal Chem, 68:1762-1770 (1996).
Theze, et al., "Interleukin 2 and its receptors: recent advances and new immunological functions," Immunology Today 17:481-486 (1996).
Török "Calmodulin conformational changes in the activation of protein kinases," Biochem Soc Trans 30:55-61 (2002).
Tsukamoto, et al., "Recent advances in the measurement of enantiomeric excesses," Advanced Synthesis & Catalysis 344:453-463 (2002).
van Delden, et al., "Color indicators of molecular chirality based on doped liquid crystals," Angew Chem Int Ed, 40:3198-3200 (2001).
Viola et al., "Alignment by maximization of mutual information", International Conference on Computer Vision (E. Grimson, S. Shafer, A. Blake and K. Sugihara, eds.), IEEE Computer Society Press, Los Alamitos, CA, pp. 16-23, 1995.
Vogelstein, et al., "Digital PCR," Proc Natl Acad Sci USA, 96(16):9236-9241 (1999).
Wang, et al., "High-speed digital-image correlation method," Optics Letters, vol. 34:1955-1957 (2009).
Wang et al.,"Optical vortex metrology for nanometric speckle displacement measurement," Optics Express, vol. 14:120-127 (2006).
Wang et al., "Pseudophase information from the complex analytic signal of speckle fields and its applications. Part I: Microdisplacement observation based on phase-only correlation in the signal domain," Applied Optics, vol. 44:4909-4915 (2005).
Watkins, "Scattering from side-illuminated clad glass fibers for determination of fiber parameters," J Opt Soc Am, 64:767-772 (1974).
Whitesides et al., "Soft lithography in biology and biochemistry," Annu Rev Biomed Eng, 3:335-373 (2001).
Wu, et al. "Polymer microchips bonded by 0-2-plasma activation," Electrophoresis, 23:782-790 (2002).
Yamaguchi, "Fringe formation in speckle photography," J. Opt. Soc. Am. A, vol. 1:81-86 (1984).
Yanik, et al., Development of a New Laser Based Polarimetric Detector and Its Application to High-performance Liquid Chromatography. PDR-Chiral, 1998.
Yeung, et al., "Electrochemistry-Based Real-Time PCR on a Microchip," Anal Chem, 80:363-368 (2008).
Young, et al., "Novel Recombinant-Antigen Enzyme Immunoassay for Serological Diagnosis of Syphilis," J Clin Microbio, 36(4):913-917 (1998).
Yu et al., "Energy landscape of aptamer/protein complexes studies by single-molecule force spectroscopy," Chem Asian J, 2:284-289 (2007).
Zandonella, "Cell nanotechnology: The tiny toolkit," Nature, 423:10-12 (2003).
Zhihong et al., "A new sandwich-type assay of estrogen using piezoelectric biosensor immobilized with estrogen response element," Anal Commun, 36:281-283 (1999).
PCT/US2005/38168, filed Oct. 22, 2004, Bornhop, International Search Report, Apr. 26, 2006.
PCT/US2008/077145, filed Sep. 20, 2008, Bornhop, Written Opinion, Dec. 8, 2008.
PCT/US2008/077145, filed Sep. 20, 2008, Bornhop, International Search Report, Dec. 8, 2008.
Sorensen, et al., "Absolute refractive index determination by microinterferometric backscatter detection," Anal Chem, 75:1946-1953 (2003).
Rudolph Research Analytical, "Polarimetry," webpage retrieved from www.rudolphresearch.com/polarimetry.htm on Aug. 3, 2009, pp. 1-2.
Swinney, et al., "Laser-Based Capillary Polarimetry," J Capill Electrophor Microchip Technol, 6(3-4):93-96 (1999).
Non-Final Office Action issued on Apr. 28, 2010 for U.S. Appl. No. 12/122,175, filed May 16, 2008 (Inventor—R. Jones; pp. 1-5).
Response after Non-Final Office Action filed on Jun. 29, 2010 for U.S. Appl. No. 12/122,175, filed May 16, 2008 (Inventor—R. Jones; pp. 1-17).
Notice of Allowance issued on Jul. 22, 2010 for U.S. Appl. No. 12/122,175, filed May 16, 2008 (Inventor—R. Jones; pp. 1-7).
International Search Report with Written Opinion issued on Aug. 19, 2008 for Intl. App. No. PCT/US2008/ 063879, filed May 16, 2008 (Inventor—R. Jones; pp. 1-11).
International Preliminary Report on Patentability issued on Nov. 24, 2009 for Intl. App. No. PCT/US2008/ 063879, filed May 16, 2008 (Inventor—R. Jones; pp. 1-10).
International Search Report with Written Opinion issued on Apr. 26, 2006 for Intl. App. No. PCT/US2005/38168, filed Oct. 22, 2004 (Inventor—Bornhop; pp. 1-6).
International Preliminary Report on Patenability issued on Apr. 27, 2007 for Intl. App. No. PCT/US2005/38168, filed Oct. 22, 2004 (Inventor—Bornhop; pp. 1-6).
International Preliminary Report on Patentability issued on Mar. 24, 2010 for Intl. App. No. PCT/US2008/ 077145, filed Sep. 20, 2008 (Inventor—Bornhop; pp. 1-9).
Preliminary Amendment filed on Feb. 22, 2010 for EP Pat. App. No. 08755681.7, national phase of Intl. App. No. PCT/US2008/ 077145, filed Sep. 20, 2008 (Inventor—Bornhop; pp. 1-7).
Sorensen, Henrik Schiøtt, "Self Calibrating Interferometric Sensor," PhD thesis Risø-PhD-19(EN), Risø National Laboratory, Denmark, Jan. 2006, pp. 1-145.

\* cited by examiner

FREE SOLUTION MEASUREMENT OF MOLECULAR INTERACTIONS BY BACKSCATTERING INTERFEROMETRY

CROSS-REFERENCE TO RELATED APPLICATIONS

This application claims the benefit of U.S. Application No. 60/973,829, filed Sep. 20, 2007, which is hereby incorporated herein by reference in its entirety.

ACKNOWLEDGEMENT

This invention was made with government support under Grant No. R01 EB003537-01A2 awarded by National Institutes of Health. The United States government has certain rights in the invention.

BACKGROUND

Capillary-based analysis schemes, biochemical analysis, basic research in the biological sciences such as localized pH determinations in tissues and studies in protein folding, detection and study of microorganisms, and the miniaturization of instrumentation down to the size of a chip all require small volume detection. With the advent of lasers, light sources possessing unique properties including high spatial coherence, monochromaticity and high photon flux, unparalleled sensitivity and selectivity in chemical analysis has become possible; these technologies, however, can be both expensive and difficult to implement. In contrast, refractive index (RI) detection has been successfully applied to several small volume analytical separation schemes. For various reasons, RI detection represents an attractive alternative to fluorescence and absorbance: it is relatively simple, it can be used with a wide range of buffer systems, and it is universal, theoretically allowing detection of any solute, making it particularly applicable to solutes with poor absorption or fluorescence properties.

Conventional methods of probing intermolecular interactions typically require the use of one or more surface immobilized analytes in the interaction as well as the use of chemical labels on one or both analytes. Surface immobilized methods are cumbersome due to the extraordinary effort required to optimize immobilization protocols as well as their inherently high false positive and false negative binding detection rates, due to unwanted forces contributed by the supporting substrate. Moreover, these conventional methods typically fail to achieve detection at low detection limits or with low sample volume requirements.

However, there remains a need in the art for systems and methods for free-solution, label-free detection of intermolecular interactions between analytes, preferably with low detection limits and/or low sample volume requirements.

SUMMARY

As embodied and broadly described herein, the invention, in one aspect, relates to methods comprising detecting molecular interaction between analytes in free-solution wherein at least one of the analytes is label-free and detection is performed by back-scattering interferometry.

In a further aspect, the invention relates to a method comprising detecting molecular interaction between analytes in free-solution, wherein at least one of the analytes is label-free, wherein one of the analytes is present in a concentration of less than about $5.0 \times 10^{-7}$M.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; and detecting positional shifts in the light bands.

In a further aspect, the invention relates to a method for free-solution determination of molecular interactions comprising the steps of providing a substrate having a channel formed therein for reception of a fluid sample to be analyzed, the channel containing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; and detecting positional shifts in the light bands.

In various aspects, detecting positional shifts in the light bands can comprise determining a change in a physical or chemical property of the fluid sample corresponding to the formation of the one or more interaction products of the first analyte with the second analyte. For example, the methods can further comprise the step of determining the formation of the one or more interaction products of the first analyte with the second analyte from the positional shifts of the light bands in the interference patterns.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$ M.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns.

In a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel. In one aspect, the characteristic property is the formation of one or more interaction products of the interaction of the first analyte with the second analyte.

In a further aspect, the invention relates to a detection system comprising a microfluidic channel formed in a substrate; a solution comprising label-free analytes in free solution in the channel; and an interferometer that detects molecular interactions between the analytes in the channel.

In a further aspect, the invention relates to a detection system comprising a solution comprising label-free analytes in free solution, wherein one of the analytes is present in a concentration of less than about $5.0 \times 10^{-7}$ M; and a detector that detects molecular interactions between the analytes in the solution.

In a further aspect, the invention relates to the products of the disclosed methods.

In a further aspect, the invention relates to chemical and biotechnological (e.g., nucleic acid biosensors, enzyme biosensors, cellular biosensors, measurement of end-point values, determination of kinetic parameters, immobilized bait measurements, free solution measurements, label-free molecular interactions, bioassays, and the like) applications employing the disclosed devices, systems, and methods.

Unless otherwise expressly stated, it is in no way intended that any method or aspect set forth herein be construed as requiring that its steps be performed in a specific order. Accordingly, where a disclosed method or system does not specifically state that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
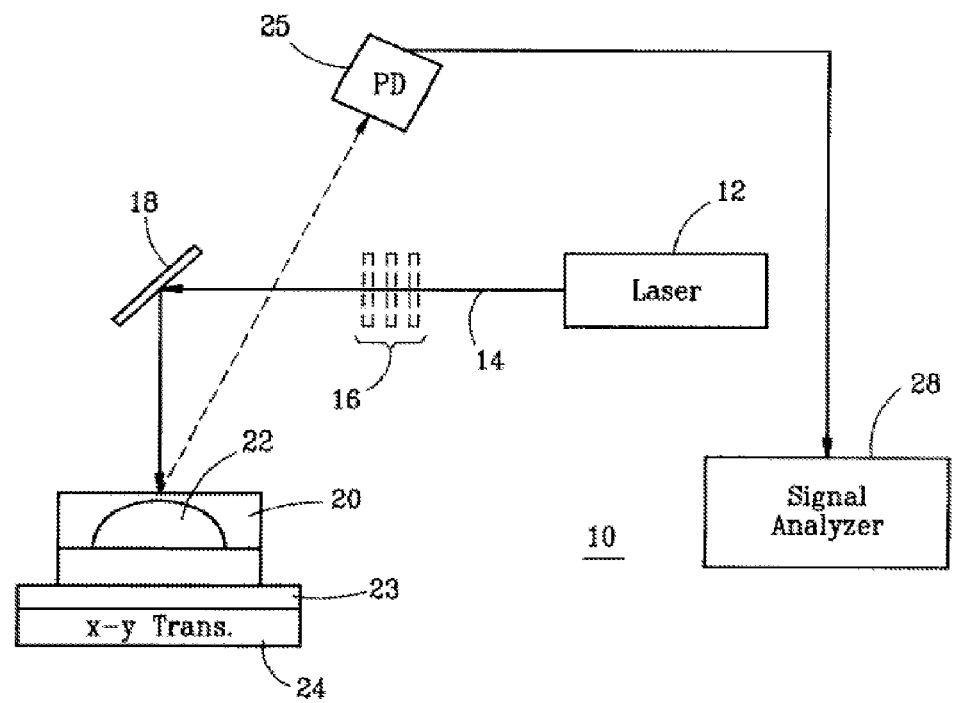
FIG. 1 shows a schematic block diagram of an interferometric detection system that is constructed in accordance with a first preferred aspect of the present invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which may need to be independently confirmed.

A. Definitions

As used in the specification and the appended claims, the singular forms "a," "an" and "the" include plural referents unless the context clearly dictates otherwise. Thus, for example, reference to "a substrate," "a polymer," or "a sample" includes mixtures of two or more such substrates, polymers, or samples, and the like.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance may or may not occur, and that the description includes instances where the event or circumstance occurs and instances where it does not.

As used herein, the term "polymer" refers to a relatively high molecular weight organic compound, natural or synthetic (e.g., polyethylene, rubber, cellulose), whose structure can be represented by a repeated small unit, the monomer (e.g., ethane, isoprene, β-glucose). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer.

As used herein, the term "bioassay" refers to a procedure for determining the concentration, purity, and/or biological activity of a substance.

As used herein, the term "chemical event" refers to a change in a physical or chemical property of an analyte in a sample that can be detected by the disclosed systems and methods. For example, a change in refractive index (RI), solute concentration and/or temperature can be a chemical event. As a further example, a biochemical binding or association (e.g., DNA hybridization) between two chemical or biological species can be a chemical event. That is, a chemical event can be the formation of one or more interaction products of the interaction of a first analyte with a second analyte. As a further example, a disassociation of a complex or molecule can also be detected as an RI change. As a further example, a change in temperature, concentration, and association/dissociation can be observed as a function of time. As a further example, bioassays can be performed and can be used to observe a chemical event.

As used herein, the terms "equilibrium constant" and "Kc" and "Keq" refer to the ratio of concentrations when equilibrium is reached in a reversible reaction. For example, for a general reaction given by the equation:

the equilibrium constant can be expressed by:

$$K_c = \frac{[C]^c[D]^d}{[A]^a[B]^b}.$$

An equilibrium constant can be temperature- and pressure-dependent but has the same value, irrespective of the amounts of A, B, C, and D. A specific type of equilibrium constant that measures the propensity of a larger object to separate (dissociate) reversibly into smaller components is a "dissociation constant" or "Kd." A dissociation constant is the inverse of an "affinity constant."

As used herein, the term "dissociation rate" is a concentration dependent quantity and involves the "dissociation rate constant" or "$K_D$." The dissociation rate constant relates the rate at which molecules dissociate to the concentration of the molecules. A dissociation can be described as AB→A+B, and the rate of dissociation (dissociation rate) is equal to $K_D$[AB]. In general, the larger the value of $K_D$, the faster the inherent rate of dissociation.

As used herein, the term "association rate" is a concentration dependent quantity and involves the "association rate constant" or "$K_A$." The association rate constant relates the rate at which molecules associate to the concentration of the molecules. An association can be described as A+B→AB, and the rate of association (association rate) is equal to $K_A$[A][B]. In general, the larger the value of $K_A$, the faster the inherent rate of association.

As used herein, the term "free-solution" refers to a lack of surface immobilization. The term is not meant to exclude the possibility that one or more molecules or atoms of analyte may associate with a surface. Rather, the term can describe the detection of an analyte without the requirement for surface immobilization during analysis.

As used herein, the term "label-free" describes a detection method wherein the detectability of an analyte is not dependent upon the presence or absence of a detectable label. For example, "label-free" can refer to the lack of a detectable label. It is understood that the ability of a label to be detected can be dependent upon the detection method. That is, an analyte having a moiety capable of serving as a detectable label for a first detection method can be considered "label-free" when a second detection method (wherein the label is not detectable) is employed. In a further aspect, the analytes employed in the disclosed systems and methods can lack detectable labels.

As used herein, the term "detectable label" refers to any moiety that can be selectively detected in a screening assay. Examples include without limitation, radiolabels (e.g., $^3$H, $^{14}$C, $^{35}$S, $^{125}$I, $^{131}$I) affinity tags (e.g. biotin/avidin or streptavidin), binding sites for antibodies, metal binding domains, epitope tags, FLASH binding domains (see U.S. Pat. Nos. 6,451,569; 6,054,271; 6,008,378 and 5,932,474), glutathione or maltose binding domains, photometric absorbing moieties, fluorescent or luminescent moieties (e.g. fluorescein and derivatives, GFP, rhodamine and derivatives, lanthanides etc.), and enzymatic moieties (e.g. horseradish peroxidase, β-galactosidase, β-lactamase, luciferase, alkaline phosphatase). Such detectable labels can be formed in situ, for example, through use of an unlabeled primary antibody which can be detected by a secondary antibody having an attached detectable label. Further examples include imaging agents such as radioconjugate, cytotoxin, cytokine, Gadolinium-DTPA, a quantum dot, iron oxide, and manganese oxide.

Disclosed are the components to be used to prepare the compositions of the invention as well as the compositions themselves to be used within the methods disclosed herein. These and other materials are disclosed herein, and it is understood that when combinations, subsets, interactions, groups, etc., of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific aspect or combination of aspects of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Interferometric Detection

In one aspect, the invention relates to an interferometric detection system and method that can be used, for example, for detection of refractive index changes in picoliter sized volumes for chip-scale analyses. The detection system has numerous applications, including the observation and quantification of molecular interactions, molecular concentrations, bioassays, universal/RI detection for CE (capillary electrophoresis), CEC (capillary electrochromatography) and FIA (flow injection analysis), physiometry, cell sorting/detection by scatter, ultra micro calorimetry, flow rate sensing, and temperature sensing.

Thus, in one aspect, the invention fulfills a need for a new sensing methodology applicable to μ-TAS (micro Total Analysis Systems) through provision of an interferometric detection system and method that circumvent the drawbacks of conventional interferometric methods and the limitations of the forward scatter technique. The system includes a source of coherent light, such as a diode or He—Ne laser, a channel of capillary dimensions that is preferably etched or molded in a substrate for reception of a sample to be analyzed, and a photodetector for detecting backscattered light from the sample at a detection zone.

In one aspect, the laser source generates an easy to align simple optical train comprised of collimated laser beam that is incident on the etched channel (or capillary) for generating the backscattered light. The backscattered light comprises interference fringe patterns that result from the reflective and refractive interaction of the incident laser beam with the channel walls and the sample. These fringe patterns include a plurality of light bands whose positions shift as the refractive index of the sample is varied, either through compositional changes or through temperature changes, for example. The photodetector detects the backscattered light and converts it into intensity signals that vary as the positions of the light bands in the fringe patterns shift, and can thus be employed to determine the refractive index (RI), or an RI related characteristic property, of the sample. A signal analyzer, such as a computer or an electrical circuit, is employed for this purpose to analyze the photodetector signals, and determine the characteristic property of the sample.

In one aspect, the channel has a generally semi-circular cross-sectional shape. A unique multi-pass optical configuration is inherently created by the channel characteristics, and is based on the interaction of the unfocused laser beam and the curved surface of the channel, that allows interferometric measurements in small volumes at high sensitivity. Additionally, if a laser diode is employed as the source, not only does this enable use of wavelength modulation for significant improvements in signal-to-noise ratio, but it also enables integration of the entire detector device directly onto a single microchip.

Alternatively, the channel can have a substantially circular or generally rectangular cross-sectional shape. In one aspect, the substrate and channel together comprise a capillary tube. In a further aspect, the substrate and channel together comprise a microfluidic device, for example, a silica substrate, or a polymeric substrate [e.g., polydimethylsiloxane (PDMS) or polymethyl methacrylate (PMMA)], and an etched channel formed in the substrate for reception of a fluid sample, the channel having a cross sectional shape. It is also contemplated that the substrate can further comprise a reference channel. For example, the detection system can employ a second channel, which can comprise a capillary or an on-chip channel of semi-circular or rectangular cross-section.

The detector can be employed for any application that requires interferometric measurements; however, the detector is particularly attractive for making universal solute quantification, temperature and flow rate measurements. In these applications, the detector provides ultra-high sensitivity due to the multi-pass optical configuration of the channel. In the temperature measuring aspect, the signal analyzer receives the signals generated by the photodetector and analyzes them using the principle that the refractive index of the sample varies proportionally to its temperature. In this manner, the signal analyzer can calculate temperature changes in the sample from positional shifts in the detected interference fringe patterns.

In the flow measuring aspect, the same principle is also employed by the signal analyzer to identify a point in time at which perturbation is detected in a flow stream in the channel. In the case of a thermal perturbation, a flow stream whose flow rate is to be determined, is locally heated at a point that is known distance along the channel from the detection zone. The signal analyzer for this aspect includes a timing means or circuit that notes the time at which the flow stream heating occurs. Then, the signal analyzer determines from the positional shifts of the light bands in the interference fringe patterns, the time at which thermal perturbation in the flow stream arrives at the detection zone. The signal analyzer can then determine the flow rate from the time interval and distance values. Other perturbations to the flow stream, include, but are not limited to, introduction into the stream of small physical objects, such as glass microbeads or nanoparticles. Heating of gold particles in response to a chemical reaction or by the change in absorption of light due to surface-bound solutes or the capture of targets contained within the solution can be used to enhance the temperature induced RI perturbation and thus to interrogate the composition of the sample.

In one aspect, the fluid sample is a liquid, which can be a substantially pure liquid, a solution, or a mixture (e.g., biological fluids, cellular fluids). In a further aspect, the fluid can further comprise one or more analytes.

1. Free-Solution Determination Methods For Molecular Interactions

In contrast to conventional techniques that observe immobilized analytes—which necessarily limit conformational and translational freedom for analytes and are, thus, in vitro measurements—free-solution analysis techniques mimic in vivo measurements, because analytes enjoy unrestricted freedom in all three dimensions during measurement.

In one aspect, the invention relates to a method comprising detecting molecular interaction between analytes in free-solution wherein one or more of the analytes are label-free and detection is performed by back-scattering interferometry. In one aspect, the analytes are present in a sample in a microfluidic channel in a substrate. In a further aspect, back-scattering interferometry comprises directing a coherent light beam onto the substrate such that the light beam is incident on the channel to generate backscattered light through reflective and refractive interaction of the light beam with a substrate channel interface and the sample, the backscattered light comprising interference fringe patterns including a plurality of spaced light bands whose positions shift in response to changes in the refractive index of the fluid sample.

In a further aspect, the invention relates to a method comprising detecting molecular interaction between analytes in free-solution, wherein one or more of the analytes are label-free, wherein one of the analytes is present in a concentration of less than about $5.0\times10^{-7}$M. In one aspect, the analytes are present in a sample in a microfluidic channel in a substrate. In a further aspect, detection is performed by back-scattering interferometry.

It is contemplated that the method can be used to determine one or more of an equilibrium constant, a dissociation constant, a dissociation rate, a dissociation rate constant, an association rate, and/or an association rate constant of the interaction.

Each of the one or more analytes can be introduced into the channel in a sample. Two or more analytes can be present in the same or in different samples. Each of the one or more analytes can independently be present in a suitable concentration, for example, a concentration of less than about $5.0\times10^{-7}$M, of less than about $1.0\times10^{-7}$M, a concentration of less than about $5.0\times10^{-8}$M, of less than about $1.0\times10^{-8}$M, of less than about $5.0\times10^{-9}$M, of less than about $1.0\times10^{-9}$M, of less than about $1.0\times10^{-10}$ M, of less than about $5.0\times10^{-10}$M, of less than about $5.0\times10^{-11}$M, of less than about $1.0\times10^{-11}$M, of less than about $5.0\times10^{-12}$M, or of less than about $1.0\times10^{-12}$M.

In one aspect, the interaction can be a biomolecular interaction. For example, two analytes can associate to provide an interaction product (e.g., adduct, complex, or new compound). In a further aspect, an analyte can dissociate to provide two or more interaction products. In further aspects, more than two analytes can be involved in the interaction.

In one aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns.

The disclosed techniques can determine the interaction between one or more analytes by monitoring, measuring, and/or detecting the formation and/or steady state relative abundance of one or more analyte interaction products from the interaction of the one or more analytes. The determination can be performed qualitatively or quantitatively. Interaction rate information can be derived from various measurements of the interaction.

In a further aspect, the first sample is combined with the second sample prior to introduction. That is, the analytes are combined (and potentially interacting) prior to performing the disclosed methods. In this aspect, the step of introducing the first analyte and the step of introducing the second analyte are performed simultaneously.

In a further aspect, the first sample is combined with the second sample after introduction. That is, the analytes can be combined at a point before the channel, or at a point within the channel, when performing the disclosed methods. In this aspect, the step of introducing the first analyte and the step of introducing the second analyte are performed either simultaneously or sequentially. In a further aspect, the detecting step is performed during the interaction of the first analyte with the second analyte.

In an alternative mode of operation, the method can involve end-point measurement. That is, the method can determine the occurrence and/or completeness of an interaction between two or more analytes that have been mixed prior to analysis. Thus, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns.

A first sample (e.g., a solution including a first non-immobilized analyte to be analyzed) can be introduced into the channel of the substrate. The first sample can be provided having a known concentration of the first analyte.

A baseline interferometric response can then be established by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample.

A second sample (e.g., a solution including a mixture of the first non-immobilized analyte and a second non-immobilized analyte to be analyzed, wherein the first analyte to interacts with the second analyte to form one or more interaction products) can then be introduced into the channel. In various aspects, the second sample can be provided as a pre-mixed sample of the first non-immobilized analyte and the second non-immobilized analyte or provided by adding a sample comprising the second non-immobilized analyte to the first sample. In one aspect, the first sample is a solution of the first analyte, which is displaced in the channel by the introduction of the second sample, which is a solution of both the first analyte and the second analyte. The second sample can be provided having a known concentration of the first analyte, which can be the same as the concentration of the first analyte in the first solution. The second sample can also be provided having a known concentration of the second analyte.

A coherent light beam can then directed onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample.

Positional shifts in the light bands relative to the baseline can then be detected, and the interaction of the first analyte with the second analyte can then be determined from the positional shifts of the light bands in the interference patterns. The rate of interaction between the two analytes can thus be monitored, thereby determining the quantity of one of the binding partners, having a priori knowledge of the abundance of its other binding partner. That is, the system and method provides a signal (i.e, positional shifts in the light bands) that is proportional to abundance of the analyte.

In a further aspect, the first analyte and/or the second analyte is/are unlabeled. While the disclosed methods can be used in connection with unlabeled analytes, it is contemplated that the analytes can be optionally labeled. Such labeling can be convenient for preceding, subsequent, or simultaneous analysis by other analytical methods.

In a further aspect, the interaction is the formation of one or more covalent bonds, electrostatic bonds, hydrogen bonds, or hydrophobic interactions. In a further aspect, the interaction creates a conformational change in at least one of the analytes. In a further aspect, the interaction is a binding event between one or more of antibody-antigen, protein-protein, small molecule-small molecule; small molecule-protein, drug-receptor; antibody-cell; protein-cell; oligonucleotide-cell; carbohydrate-cell; cell-cell; enzyme-substrate; protein-DNA; protein-aptamer; DNA-DNA; RNA-RNA; DNA-RNA; protein-RNA; small molecule-nucleic acid; biomolecule-molecular imprint; biomolecule-protein mimetic; biomolecule-antibody derivatives; lectin-carbohydrate; biomolecule-carbohydrate; small molecule-micelle; small molecule-cell membrane; and enzyme-substrate.

In a further aspect, a fluid sample can comprise at least one of a liquid or a gas. In particular aspects, a fluid sample comprises a solution of one or more analytes and one or more liquid solvents. A solution can be provided in an organic solvent or in water. In certain aspects, the solution can comprise man-made preparations or naturally occurring substances. In certain aspects, the solution can comprise a body fluid (e.g., peripheral blood, urine, cerebrospinal fluid, pulmonary lavage, gastric lavage, bile, vaginal secretions, seminal fluid, aqueous humor, and vitreous humor) from a human, a mammal, another animal, or a plant.

Generally, the substrate and channel can comprise any material suitable for containing and providing a sample for analysis and capable of being interrogated by the coherent light beam to generate backscattered light through reflective and refractive interaction of the light beam with a substrate/channel interface and the sample. In one aspect, the substrate and channel together comprise a capillary tube. In a further aspect, wherein the substrate and channel together comprise a microfluidic device.

In a further aspect, the microfluidic device comprises a polymeric substrate and an etched channel formed in the substrate for reception of a fluid sample, the channel having a cross sectional shape. In a further aspect, the polymeric substrate can be selected from rigid and transparent plastics. In various further aspects, the polymeric substrate comprises one or more polymers selected from polycarbonate, polydimethylsiloxane, fluorosilicone, polytetrafluoroethylene, poly (methyl methacrylate), polyhexamethyldisilazane, polypropylene, starch-based polymers, epoxy, and acrylics.

In a further aspect, the microfluidic device comprises a silica substrate and an etched channel formed in the substrate for reception of a fluid sample, the channel having a cross sectional shape, which can be substantially circular, substantially semi-circular, or substantially rectangular, as disclosed herein.

It is contemplated the substrate can comprise one or more than one channel. In a further aspect, the substrate further comprises a reference channel.

The disclosed methods can provide real-time, free-solution detection of molecular interactions with very low detection limits. That is, in one aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$M. In various further embodiments, the concentration can be less than about $1.0 \times 10^{-5}$M, for example, less than about $5.0 \times 10^{-6}$M, less than about $1.0 \times 10^{-6}$M, less than about $5.0 \times 10^{-7}$M, less than about $1.0 \times 10^{-7}$M, less than about $5.0 \times 10^{-8}$M, less than about $1.0 \times 10^{-8}$M, less than about $5.0 \times 10^{-9}$M, or less than about $1.0 \times 10^{-9}$M. In a further aspect, the concentration can be less than about $5.0 \times 10^{-10}$M, for example, less than about $1.0 \times 10^{-10}$M, less than about $5.0 \times 10^{-11}$M, less than about $1.0 \times 10^{-11}$M, less than about $5.0 \times 10^{-12}$M, or less than about $1.0 \times 10^{-12}$M.

The disclosed methods can provide real-time, free-solution detection of molecular interactions with very low sample volume requirements. That is, in one aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL. In various further embodiments, the sample volume can be less than about 250 nL, for example, less than about 100 nL, less than about 10 nL, less than about 1 nL, less than about 500 pL, less than about 250 pL, or less than about 100 pL.

In an even further aspect, the disclosed methods further comprise the step of performing a chromatographic separation and/or an electrophoretic separation on the sample before, during, or after the determining the characteristic property step.

2. Interferometric Detection Systems for Free-Solution Determination of Molecular Interactions In one aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel.

In one aspect, the invention relates to a detection system comprising a microfluidic channel formed in a substrate; a solution comprising label-free analytes in free solution in the channel; and an interferometer that detects molecular interactions between the analytes in the channel. In a further aspect, the invention relates to a detection system comprising a solution comprising label-free analytes in free solution, wherein one of the analytes is present in a concentration of less than about $5.0 \times 10^{-7}$M; and a detector that detects molecular interactions between the analytes in the solution. The detector can be, for example, an interferometer. Likewise, detection can be, for example, by means of back-scattering interferometry. The channel can be formed by, for example, etching, by molding, by micromachining, or by photolithography. It is contemplated that the system can be used to determine one or more of an equilibrium constant, a dissociation constant, a dissociation rate, a dissociation rate constant, an association rate, and/or an association rate constant of an interaction.

In various aspects, a means for introducing a sample can be any apparatus, system, or construct capable of conveying a sample into the system and/or directing a sample into or through the channel such that the light beam incident on the channel encounters at least a portion of the sample, thereby generating backscattered light through reflective and refractive interaction of the light beam with a substrate/channel interface and the sample. Examples of means for introducing a sample include an opening in a capillary tube, an injection port, a second capillary tube in fluid communication with the substrate and channel, a microfluidic channel in fluid communication with the substrate and channel, a syringe, a pipette, a chromatographic separation apparatus in fluid communication with the substrate and channel, and/or an electrophoretic separation apparatus in fluid communication with the substrate and channel.

It is understood that the means for introducing a first sample and the means for introducing a second sample can comprise the same or a different means. It is also understood that the means for introducing a first sample and the means for introducing a second sample can comprise the same type (e.g., both are injection ports) or a different type (e.g., one is a capillary tube and the other is a syringe) of means.

In various aspects, a means for mixing can be any means for apparatus, system, or construct capable of combining two samples such that the samples are in intimate contact and capable of interacting physically and/or chemically. Examples of means for mixing include a blender, a sonication apparatus, a microfluidic serpentine mixer, and a microfluidic restriction.

In a further aspect, the coherent light source is a laser, for example a He/Ne laser, a VCSEL laser, or a diode laser.

In a further aspect, the system can further comprise a reference channel. In a further aspect, the substrate and channel together comprise a capillary tube. In a further aspect, the substrate and channel together comprise a microfluidic device. In a further aspect, the microfluidic device comprises a silica substrate and an etched channel formed in the substrate for reception of a fluid sample, the channel having a cross sectional shape. In a further aspect, the microfluidic device comprises a glass substrate and an etched channel formed in the substrate for reception of a fluid sample, the channel having a cross sectional shape. In a further aspect, the cross sectional shape is substantially rectangular, substantially circular, or generally semi-circular. In a still further aspect, the microfluidic device comprises a polymeric substrate and an etched channel formed in the substrate for reception of a fluid sample, the channel having a cross sectional shape. In a further aspect, the polymeric substrate can be selected from rigid and transparent plastics. In various further aspects, the polymeric substrate comprises one or more polymers selected from polycarbonate, polydimethylsiloxane, fluorosilicone, polytetrafluoroethylene, poly(methyl methacrylate), polyhexamethyldisilazane, polypropylene, starch-based polymers, epoxy, and acrylics.

Thus, in various aspects, the channel is formed by etching, by molding, by micromachining, or by photolithography.

With reference now to one aspect of the invention, an interferometric detection system 10 is illustrated in FIG. 1 which makes use of a technique that employs backscattered light to determine the RI or RI related characteristic properties of a sample. The backscatter detection technique is generally disclosed in U.S. Pat. No. 5,325,170 to Bornhop, which is hereby incorporated by reference. More recently, the technique is referred to as Back-Scatter Interferometry or BSI.

The interferometric detection system 10 includes a laser or other source of coherent light 12, which is preferably a low power (3-15 mW) laser (He/Ne or Diode), and generates a laser beam 14. As with any interferometric technique for micro-chemical analysis, BSI benefits from many of advantages lasers provide, including high spatial coherence, monochromaticity, and high photon flux. The intensity of the laser beam 14 can be reduced as needed with a series of optional neutral density filters 16 (e.g., optical density of 0.5, 1.0, 0.3 respectively). Upon reduction of the intensity, the beam 14 is directed to an optional mirror 18 that is angled at approximately 45° with respect to the plane of propagation of the laser beam 14. The mirror 18 re-directs the beam 14 onto a substrate chip 20 having a channel 22 formed therein, preferably by etching, for reception of a sample volume to be analyzed. It will be understood that the mirror 18 can be deleted, and the laser 12 can be repositioned to aim the laser beam 14 directly at the etched channel 22 if desired.

The chip 20 is preferably formed of silica or glass, but can be any other suitable optically transmissive material, such as plastic (i.e., polymeric material). One requirement, however, is that the material from which the chip 20 is made, must have a different index of refraction than that of a sample volume to be tested. In the exemplary aspect of FIG. 1, the chip 20 is shown mounted on a peltier temperature controlled A1 support block 23, which in turn is affixed to an X-Y translation stage 24 that allows adjustment of the chip 20 relative to the laser beam 14. More particularly, the chip 20 is preferably tilted slightly (e.g., approximately 7°) so that the (nearly direct) backscattered light from the channel 22 can be directed onto a photodetector 25. The purpose of the temperature controlled support block 23 is to insure that the sample in the channel 22 is maintained at a constant temperature since the RI of a sample is known to vary linearly with its temperature. Alternatively, this characteristic also allows the detection system 10 to be utilized for making very accurate temperature measurements.

Figure 4:
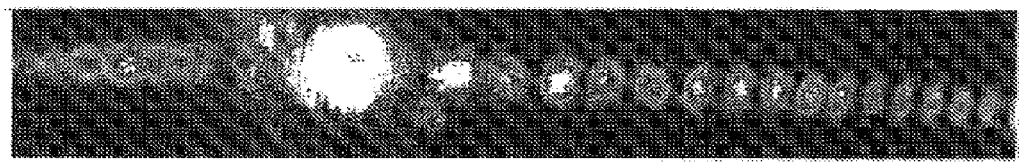
FIG. 4 is an illustration of an interference fringe pattern that is produced by the system of FIG. 1.

The photodetector 25 can be one of any number of image sensing devices, including a bi-cell position sensor, a linear or area array CCD or CMOS camera and laser beam analyzer assembly, a slit-photodetector assembly, an avalanche photodiode, or any other suitable photodetection device. The backscattered light comprises interference fringe patterns that result from the reflective and refractive interaction of the incident laser beam 14 with the walls of the channel 22 and the sample. These fringe patterns include a plurality of light bands (see FIG. 4) whose positions shift as the refractive index of the sample is varied, either through compositional changes or through temperature changes, for example. The photodetector 25 detects the backscattered light and converts it into one or more intensity signals that vary as the positions of the light bands in the fringe patterns shift. For fringe profiling, the photodetector 25 is preferably mounted above the chip 20 at an approximately 45° angle thereto.

The intensity signals from the photodetector 25 are fed into a signal analyzer 28 for fringe pattern analysis, and determination therefrom of the RI or an RI related characteristic property of a sample in the channel 22. The signal analyzer 28 can be a computer (e.g., a PC) or a dedicated electrical circuit, for example. Preferably, the signal analyzer 28 includes the programming or circuitry necessary to determine from the intensity signals, the RI or other characteristic properties of the sample to be determined, such as temperature or flow rate, for example.

Figure 2:
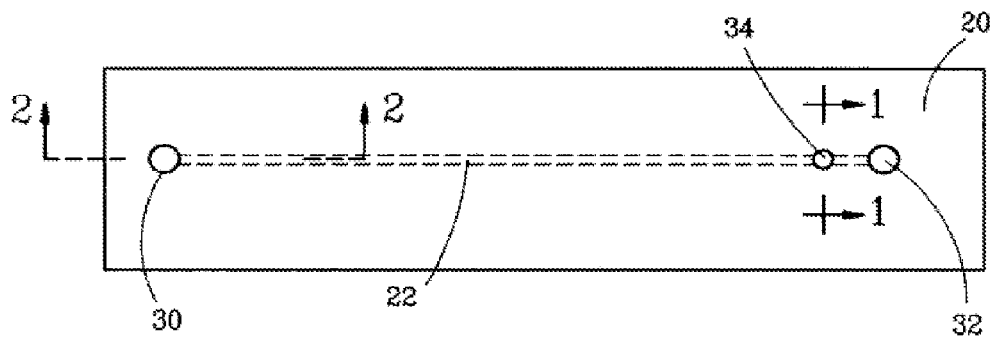
FIG. 2 shows a diagrammatic illustration of a silica or other material chip having a channel therein that forms a part of the system of FIG. 1, and is employed for receiving a sample whose refractive index or refractive index related characteristic properties are to be determined.

FIG. 2 shows a top view of the chip 20 showing the channel 22. An injection port 30 and an exit port 32 are laser drilled at opposite ends of the channel 22 to allow for introduction and removal of a fluid sample to be analyzed. The laser beam 14 is directed to impinge upon the channel 22 at a point 34 that is a short distance (e.g., about 2 mm) from the exit port 32 and is graphically shown by the circle, labeled "detection zone," in FIG. 2.

Figure 3A:
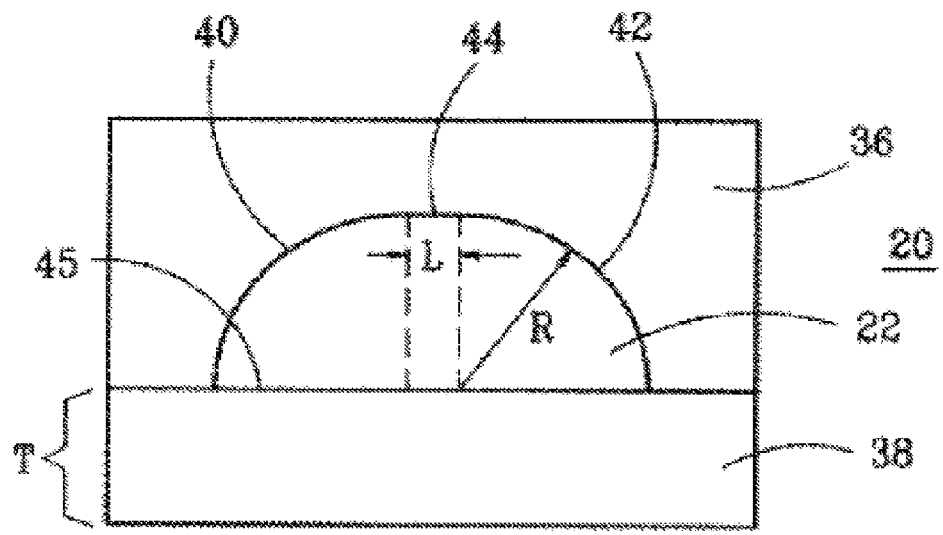
FIGS. 3A and 3B show sectional views of the chip of FIG. 2 showing the shape of the channel, with FIG. 3A being taken along line 1-1 of FIG. 2, and FIG. 3B being taken along line 2-2 of FIG. 2.
Figure 3B:
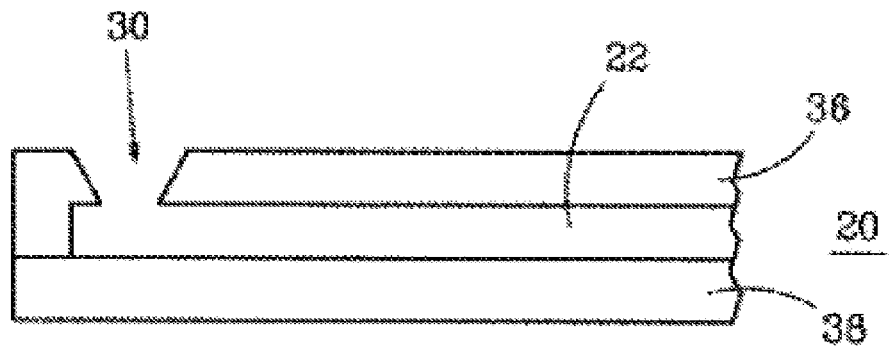

As illustrated in FIGS. 3A and 3B, the chip 20 preferably consists of first and second substrate pieces 36 and 38 that are fused together, with the channel 22 being formed in the first, top substrate piece 36, and having a generally semicircular cross-sectional shape. The semicircle has a radius R of between 5 and 150 microns, and most preferably between 10 and 50 microns. Although it is preferred that the channel 22 be truly semicircular in shape, to accommodate conventional etching techniques, the channel 22 is formed by first etching a first 90 degree arc 40 in the top substrate piece 36, and then etching a second 90 degree arc 42. This etching process inherently results in the formation of a short, flat portion or segment 44 between the first and second arcs 40 and 42. The length L of the flat portion 44 should be as short as possible, preferably 5-25 microns. When the length of the flat portion 44 does not exceed the length of the channel radius R, there is no adverse effect on the interference fringes that are generated by the channel 22. The second, bottom substrate piece 38 forms a floor 45 of the channel 22, and has a thickness T that is approximately one third to one times the radius R of the arcs 40 and 42.

Even though the channel 22 can be of the general shape of a semi-circle (half circle), including the flat portion 44, relatively high contrast interference fringes (much like those seen with full capillaries) have been observed in experiments on a prototype of the invention. The inherent characteristics of the channel 22 result in a multi pass optical configuration in which multipath reflections occur, and increase the sensitivity of the detector system 10. A typical interference pattern produced by an unmodified chip filled with distilled/deionized water is shown in the false color intensity profile (black no photons and white is the intensity for detector saturation) shown in FIG. 4. These observations can be important because, 1) the features (arcs 40 and 42) on the chip 20 that produce the interference fringes are quite common and easy to manufacture, 2) no additional optics are needed, and 3) the fringes have very high contrast allowing sensitive detection of optical path length changes. It is noteworthy that all of the measurements are obtained using a very simple optical train with no additional focusing or collection optics and using a chip that has no reflective coatings. In short, the chip-scale RI detector configuration can use unaltered chips.

Numerous experiments have been conducted to verify the operation of the on-chip detection system 10, and determine which components provide the best sensitivity. A first experiment using varying concentrations of a glycerol solution was performed to evaluate the detection system 10 using the CCD camera for recording and measuring fringe movement. The fringe movement varies linearly with concentration (change in RI) over 2 decades. The limit of detection calculated at 3$\delta$ was 31.47 mM of solute and was limited mainly by the LBA (Laser Beam Analyzer from Spiricon, Inc. Logan, Utah) software used at that time to read the camera.

In a further experiment, to improve the sensitivity of the on-chip RI measurement, the neutral density filters 16 were removed and a slit/photodetector assembly was used instead of the CCD camera/laser beam analyzer system. In this experiment, the slit/photodetector assembly was located on the order of 28 cm from the front surface of the chip 20. The photodetector 25 consisted of a pin photodiode integrated with a 632.8 nm interference filter (Coherent-Ealing) wired with a simple current to voltage circuit. A 50-micron precision air slit (Melles Griot) was mounted vertically in the center of the active surface area of the photodiode. The voltage output from the photodiode was then amplified (Gain=100) by a low-noise preamplifier (Stanford Research Systems) using a 30 Hz low pass filter (12 dB/octave). The analog signal from the preamplifier was then digitized with an external DAQ board (PPIO-AIO8, CyberResearch, Branford, Conn.) and displayed on the PC computer 28 running a digital strip-chart recorder (Labtech for Windows).

The slit-photodetector assembly was aligned on the edge of a fringe in order to monitor fringe movement. The position of the assembly corresponds to the edge of the sloping intensity gradient of the working fringe and is located at $I=1/e^2$ of the intensity distribution. Since the intensity of a backscattered fringe is essentially Gaussian, a change in refractive index of the solution in the probe volume produces a change in the light intensity striking the active surface of the photodetector 25. As the fringe shifts, a small voltage output from the photodetector 25 is observed, which is linearly proportional to a change in refractive index ($\Delta n$).

A calibration curve was generated with the slit/photodetector using the exact same procedure and glycerol solutions of the same concentrations as with the CCD/LBA configuration. The 3δ detection limit for the backscatter detector using a slit/photodetector assembly was found to be 18.33 mM, substantially better than the 31.47 mM limit achieved with the CCD/LBA experimental set up. The lower detection limits are achievable with a slit/photodetector assembly since small positional shifts of the backscattered fringes result in large intensity changes due to their pseudo-Gaussian intensity profile. The CCD/laser beam analyzer system measures only positional shifts, which are considerably less sensitive than the intensity changes seen by the slit/photodetector assembly.

In a further experiment, to improve the signal-to-noise ratio of the measurement still further, the photodetector 25 was a small area avalanche photodiode (e.g., such as those available from Texas Optoelectronics, Inc.). The avalanche photodiode (APD) was operated near the breakdown voltage and driven with a reverse bias. The APD was aligned on the edge of the fringe as described for the slit/photodetector assembly, and fringe movement was denoted by changes in intensity. The signal from the APD was digitized with an external DAQ board (PPIO-AIO8, CyberResearch, Branford, Conn.) and displayed on the PC computer 28 running a digital stripchart recorder (Labtech for Windows).

Running tests on a series of glycerol solutions revealed that the 3δ detection limit for glycerol is just 4.1 mM. By using the APD (even at a wavelength, 632.8 nm, where the device has poor quantum efficiency) a 4.4 fold S/N gain is realized.

Still further increases in sensitivity have been realized in subsequent experiments using a bi-cell position photodetector, and a diode laser with special optics to produce a pseudo-Gaussian beam of approximately 75 μm, at a distance of 50 cm and over a relatively long focal length. In this study the detection volume was 188 picoliters and a 2δ concentration detection limit for glycerol of 494 μM ($139 \times 10^{-15}$ moles or 12.8 picograms of solute) was attained, without active thermal control. Thus, a reduction in the volume and an increase in sensitivity were realized as a consequence of several technical modifications to the system.

The detection limits achieved in the foregoing experiments represent the lowest RI detection limits that have been achieved to date with a system that is compatible with chip-scale sensing (low nanoliter detection volumes). For reference, BSI is already an order of magnitude more sensitive than the holographic forward scatter technique.

It is noteworthy that these detection limits were accomplished without any active thermal control of the chip (resulting in increased noise due to thermal perturbations in the dc mode (i.e., no wavelength modulation)) and using minimal active electronic filtering. In measurements of refractive index (n), the primary source of noise is thermal sensitivity. For most cases involving fluids, n has a relatively high thermal coefficient (dn/dT), requiring very precise temperature stabilization of the system. As an example, dn/dT for $H_2O$ is on the order of $8 \times 10^{-4\circ}$ $C.^{-1}$, so at an analytically useful detection limit for Δn of one part in $10^6$, the temperature-induced signal corresponds to a change in T of $1 \times 10^{-2\circ}$ C. Therefore, thermal stability of the system must be maintained at the millidegree centigrade label, to determine n to one part in $10^8$. This level of temperature control can be achieved using a thermostated flow cell with active control using a Peltier thermoelectric cooling chip (e.g., such as is available from Melcore, Trenton, N.J.) controlled by a power supply (e.g., ILX Lightwave, Bozeman, Mont.) wired in feedback from a calibrated thermocouple.

Conversely, as discussed previously, thermal "noise" in RI measurements can be used to the advantage of the analyst. For example, thermal sensitivity can be used to determine minute temperature changes in small-volume following streams, non-invasive process stream monitoring, and even protein folding. The relationship between do and dT is linear. Therefore, BSI can be used to measure thermal changes at a microdegree centigrade level and to determine dn/dT for fluids.

To demonstrate use of the system 10 of FIG. 1 for detecting temperature changes, another experiment was conducted. In this experiment, thermometry was performed in a probe volume of just $3.14 \times 10^{-9}$ L as defined by the diameter of the laser beam 14 and the radius (in this case, 50 microns) of the etched channel 22. Distilled/deionized water was hydrodynamically injected into the channel 22 and allowed to temperature- and pressure-stabilize. Next the temperature of the channel 22 was manually changed in approximately 0.3° C. increments, the sample was allowed to temperature stabilize, and a relative change in refractive index measurement was obtained. Upon graphing the results of relative change in RI versus temperature for water, a detection limit of 0.011° C. (11 millidegree C.) was determined based on the 3 sigma statistics. These results confirm that the signal analyzer 28 can be programmed to determine the temperature of the sample from an analysis of the fringe pattern signals with a high degree of sensitivity.

Figure 5:
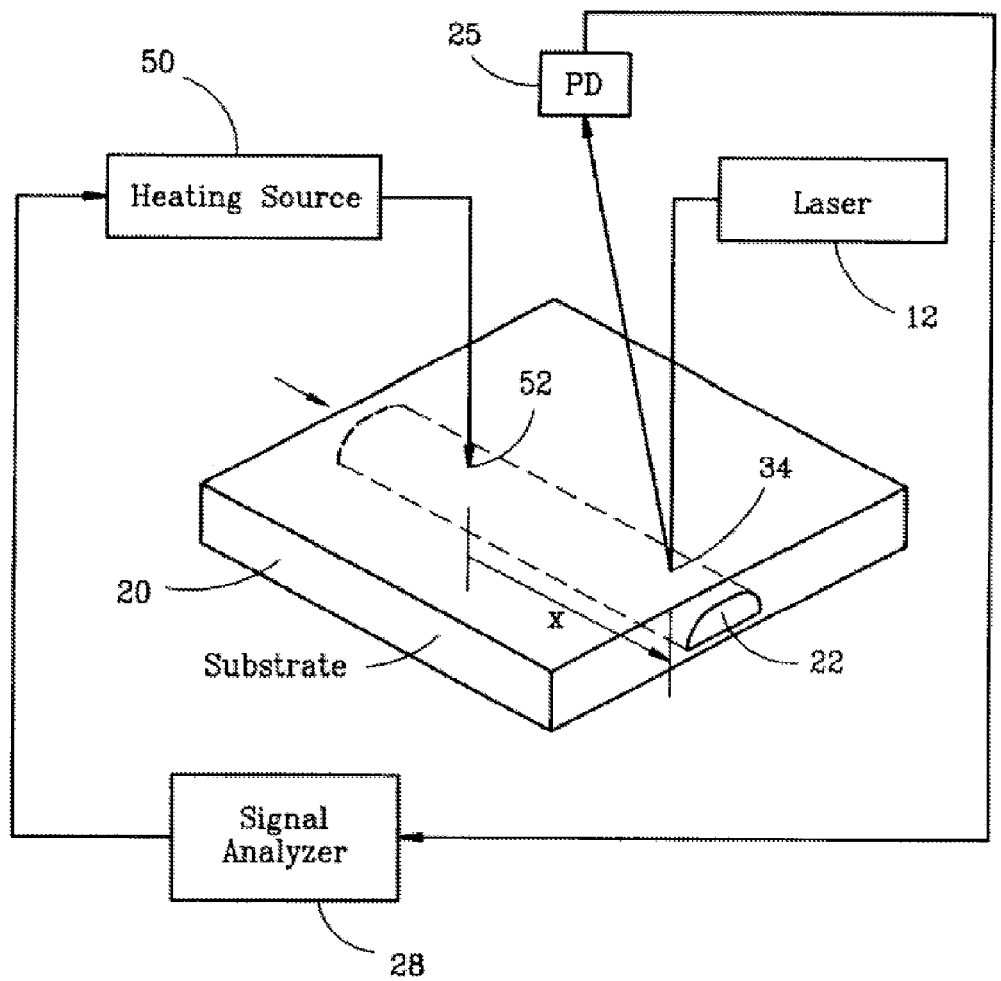
FIG. 5 is a schematic illustration of a second preferred aspect of the present invention that is employed for measuring the flow rate of a flow stream.

A further aspect of the present invention is illustrated in FIG. 5. This aspect is designed for measuring the flow rate of a flow stream flowing through the channel 22. The signal analyzer 28 in this aspect contains timing circuitry or programming, and controls operation of a heating source 50 that provides localized heating of a point 52 along the channel 22 that is spaced a known distance x from the detection zone 34. Preferably, the heating source is an infrared laser that can provide rapid localized heating of a sample flow stream in the channel 22.

In the operation of this aspect, the heating source 50 is triggered at a first instant in time to provide the localized heating of a portion of the flow stream. This creates a temperature perturbation in the flow stream that moves toward the detection zone 34. The signal analyzer 28 then monitors the intensity signals generated by the photodetector 25, and detects therefrom, the instant in time when the temperature perturbation arrives at the detection zone 34. The time interval between when the flow stream was heated and when the temperature perturbation is detected is then employed with the value of x to determine the flow rate of the flow stream.

Figure 6:
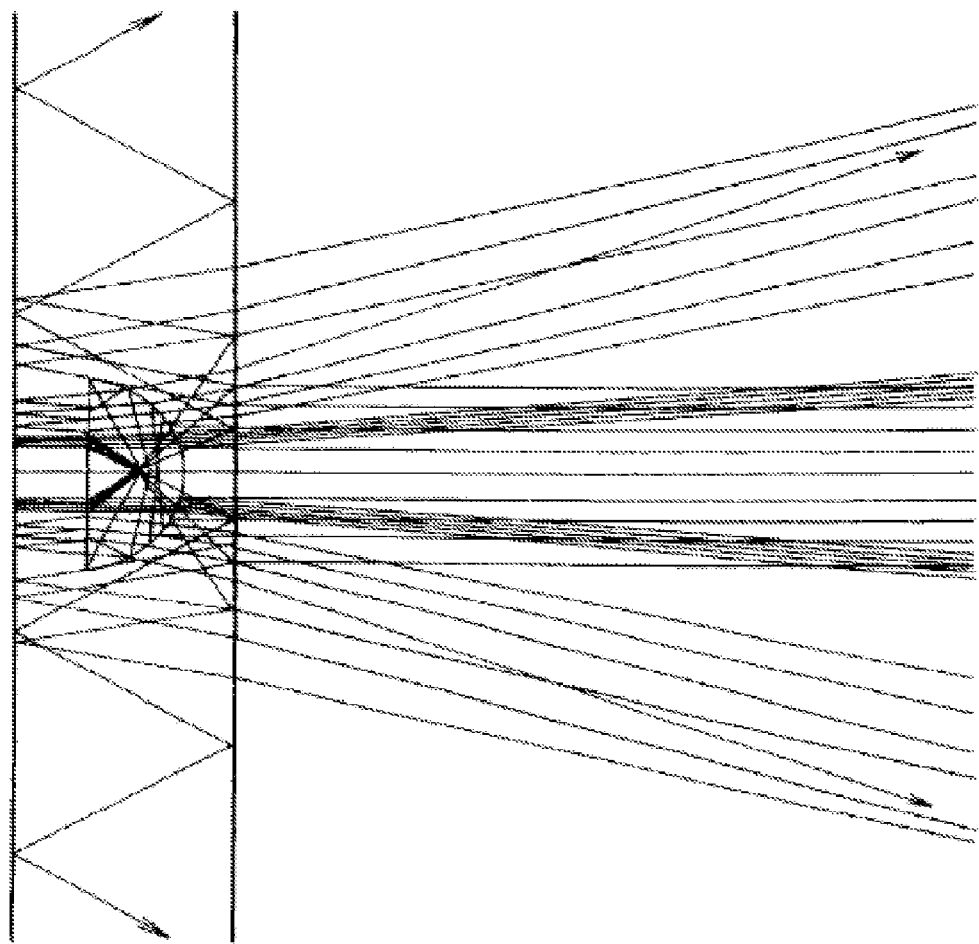
FIG. 6 is a schematic illustration of the interaction of an incident laser beam on the curved channel of the system of FIG. 1.

Using ASAP (an optical modeling program from Breault Research, Tuscon Ariz.) a few preliminary modeling experiments were performed to demonstrate the multi pass optical configuration provided by the channel 22, and the path length insensitivity that results. In the first investigation illumination impinges onto the etched side of the chip 20, so that the light impinges on the curved surface just after entering the substrate. FIG. 6 illustrates the results of this simulation, and clearly shows the multipath reflections that increase the system's sensitivity, or leads to an inherent insensitivity of performance on the size of the channel 22. Put another way, the multi pass configuration eliminates optical path length constraints, thus allowing for smaller and smaller detection volumes. In FIG. 6, nine initial rays are traced through a chip with an etched channel with a diameter of 100 μm. The laser source is located at some distance in +Z direction. Splits (the number of rays that will continue at interfaces) are set to 3. The middle plane simulates the lid that covers the channel. Since the index refraction on both sides of that plane is the same its presence does not affect the rays intersecting that plane. Since the rays that continue to travel in the −Z direction, after they passed through the chip, do not contribute to the formation of the backscattered fringe pattern, they can be ignored and dropped out of simulation.

Even lower detection limits for BSI can be achieved. First, simply increasing the distance of the photodetector 25 from the front surface of the etched channel 22 can produce larger "apparent" fringe movement because angular displacement grows as the detector to channel distance increases. In general, this geometric relationship dictates sensitivity to angular displacement and indicates that every two-fold increase in distance can produce at least a two-fold sensitivity improvement. Second, lower detection limits can be achieved by using either a longer wavelength laser or an APD whose sensitivity is maximized at the wavelength of the laser used. For example, at the He/Ne wavelength of 632.8 nm, the radiant responsivity of the current detector is approximately 10 A/W, but at the wavelength of 700 nm, the radiant responsivity of the device increases by a factor of three to 30 A/W. As a result, detection limits are predicted to improve by at least threefold. Third, the detection volume for BSI on a chip can be further reduced by using a smaller diameter laser beam (e.g., lasers generating 10 μm diameter beams are available), or a fiber couple diode laser combined with a smaller radius channel.

With respect to the detector system 10, while HeNe lasers have excellent optical properties, they can be limited in applications that demand miniaturization by their bulky size. As a result, VCSELs and diode lasers are replacing HeNe lasers in many industrial, medical, and analytical applications. VCSELs and diode lasers, in general, are solid state, low-cost compact, light sources that possess many of the properties of gas lasers (HeNe's). Among them are good beam quality ($TEM_{00}$), low divergence, and some polarization purity. Furthermore, they have characteristic long lifetimes (in excess of 50,000 hours), and provide reasonable coherent lengths (as great as 1 meter). VCSELs and diode lasers can differ, however, from HeNe lasers in several ways, particularly when using them as interferometry sources. First, wavelength stability of most VCSELs and diode lasers is generally poor due to the device's structure (small cavity size), resulting in a dependency on and sensitivity to current and temperature changes. Second, while emitting light that is inherently linearly polarized, the polarity purity of a VCSEL's or diode laser's beam is relatively low (100:1). Nevertheless, if proper care is taken, VCSELs and diode lasers are low cost, coherent light sources that are adequate for interferometric detection schemes such as BSI for both RI and polarimetric detection.

Figure 7:
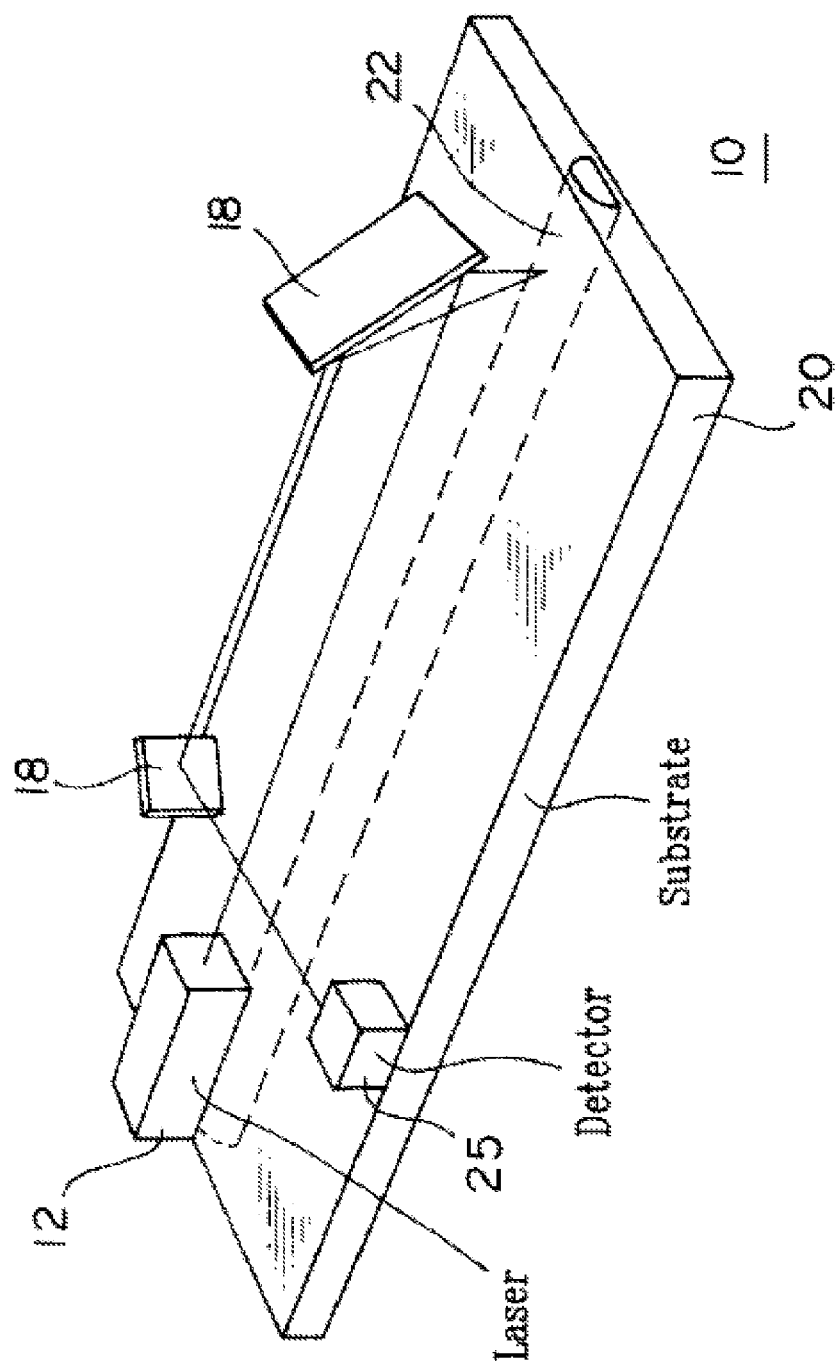
FIG. 7 is a schematic block diagram of another aspect of the invention in which all of the system elements are formed on a single microchip.

One advantage of VCSELs and diode lasers is that they can facilitate reduction in size of the RI detector system 10 to the point of being incorporated directly onto the chip 20. FIG. 7 illustrates such an aspect in which both the laser 12 and the photodetector 25 are formed integrally with the chip 20.

Another advantage of using VCSELs or laser diodes in interferometry is that their optical output (wavelength) can be easily modulated through the supply current. Wavelength modulation opens a path to potential alternative detection schemes in on-chip RI detection using micro-interferometry as a method of decreasing thermal sensitivity of the measurement and lowering the limit of detection of the technique. Thus, the system 10 can be configured so that detection is performed in the AC regime (source wavelength modulation).

When wavelength modulation techniques are used with VCSELs and diode lasers, it is possible to make exceeding sensitive optical absorbance measurements. In fact the sensitivity possible approaches the shot noise limit, i.e. $10^{-7}$ AU in a 1 Hz bandwidth. Furthermore, with the advent of rapidly tunable (over a wide wavelength range), single mode, circular beam VCSELS, these devices are suitable sources for the on-chip interferometric detection technique. In short, by using such an approach for on-chip RI detection based on micro-interferometry, a significant (as much as 500-fold) improvement in S/N can be achievable for the instrument.

Using on-chip RI detection based on micro-interferometry, the disclosed invention performs interference detection in channels with ultra-small volumes and with a simple optical configuration that requires no additional optics. The on-chip RI detector is an effective universal detection system that expands the ability to sense or quantitatively detect otherwise invisible solutes, particularly those important to clinical diagnostics, proteomic, genomic and metabolomic analysis and high throughput molecular drug screening The detector's S/N ratio is not hindered by volume reduction, its probe volume and detection volume are the same, it is a non-invasive method, and is universal in nature. Thus, the detector can play an important role in integrated-omics technology, drug discovery and development and diagnostic medicine. It can also allow protein folding and biochemical bonding measurements previously not possible. Reaction kinetics can be followed in nanoliter volumes, and millidegree temperature changes can be quantified. Finally, the invention allows the further development of μ-TAS and other techniques for cellular level analysis and bioassays and clinical diagnostic testing.

C. Back-Scattering Interferometry

Rapid monitoring and quantitative detection of ultra small volume samples is in great demand. One analytical approach, Back-Scattering Interferometry (BSI), derives from the observation that coherent light impinging on a cylindrically shaped capillary produces a highly modulated interference pattern. Typically, BSI analyses reflections from a capillary tube filled with a liquid of which one wants to measure the refractive index. First used and described by Bornhop et al. [Bornhop, D. J. Appl. Opt., 1995, 34, 3234 3239; Bornhop, D. J. U.S. Pat. No. 5,325,170, 1994; Swinney, K; Markov, D; Bornhop, D. J., Review of Scientific instruments, 2000, 71, 2684 2692.], the technique has been shown capable of measuring changes in refractive index of liquids on the order of $10^{-7}$. The BSI technique is a simple and universal method of detecting refractive index changes in small volumes of liquid and can be applied to monitor changes in concentrations of solutes, flow rates and temperature, all conducted in nanoliter volumes.

The BSI technique is based on interference of laser light after it is reflected from different regions in a capillary or like sample container. Suitable methods and apparatus are described in U.S. Pat. No. 5,325,170 and WO-A-01/14858, which are hereby incorporated by reference. The reflected or back scattered light is viewed across a range of angles with respect to the laser light path. The reflections generate an interference pattern that moves in relation to such angles upon changing refractive index of the sample. The small angle interference pattern traditionally considered has a repetition frequency in the refractive index space that limits the ability to measure refractive index to refractive index changes causing one such repetition. Such refractive index changes are typically on the order of three decades.

Accordingly, the disclosed invention provides a method for performing a measurement of refractive index comprising directing a coherent light beam along a light path to impinge on a first light transmissive material and pass there through, to pass through a sample which is to be the subject of the measurement, and to impinge on a further light transmissive material, the sample being located between the first and further materials, detecting reflected light over a range of angles with respect to the light path, the reflected light including reflections from interfaces between different substances including interfaces between the first material and the sample and between the sample and the further material which interfere to produce an interference pattern comprising alternating lighter and darker fringes spatially separated according to their angular position with respect to the light path, and conducting an analysis of the interference pattern to determine there from the refractive index, wherein the analysis comprises observation of a parameter of the interference pattern which is quantitatively related to sample refractive index dependent variations in the intensity of reflections of light which has passed through the sample.

In accordance with preferred variants of this procedure, the analysis comprises one or both of: (a) the observation of the angle with respect to the light path at which there is an abrupt change in the intensity of the lighter fringes, or (b) the observation of the position of these fringes of a low frequency component of the variation of intensity between the lighter and darker fringes. The first of these (a), relies upon the dependency of the angle at which total internal reflection occurs at an interface between the sample and the further material on the refractive index of the sample. The second (b), relies upon the dependency of the intensity of reflections from that interface on the refractive index as given by the Fresnel coefficients. The rectangular chips also have a single competent from diffraction at the corners.

The first material and the further material are usually composed of the same substance and may be opposite side walls of a container within which the sample is held or conducted. For instance, the sample may be contained in, e.g. flowed through, a capillary dimensioned flow channel such as a capillary tube. The side wall of the capillary tube nearer the light source is then the "first material" and the opposite side wall is the "further material." The cross-sectional depth of the channel is limited only by the coherence length of the light and its breadth is limited only by the width of the light beam. Preferably, the depth of the channel is from 1 to 10 um, but it may be from 1 to 20 um or up to 50 um or more, e.g. up to 1 mm or more. However, sizes of up to 5 mm or 10 mm or more are possible. Suitably, the breadth of the channel is from 0.5 to 2 times its depth, e.g., equal to its depth.

In one aspect, at least one the interface involving the sample at which light is reflected is curved in a plane containing the light path, the curved interface being convex in the direction facing the incoming light if it is the interface between the first material and the sample and being concave in the direction facing the incoming light if it is the interface between the sample and the further material. Preferably, the sample is in a channel of substantially circular, generally semi-circular, or rectangular cross-section.

The sample is typically a liquid, and can be flowing or stationary. However, the sample can also be a solid or a gas in various aspects of the present invention. The first and/or further materials will normally be solid but in principle can be liquid, e.g., can be formed by a sheathing flow of guidance liquid(s) in a microfluidic device, with the sample being sheathed flow of liquid between such guidance flows. The sample may also be contained in a flow channel of appropriate dimensions in substrate such as a microfluidic chip. The method may therefore be employed to obtain a read out of the result of a reaction conducted on a "lab on a chip" type of device.

In contrast to conventional, the invention can, in one aspect, make use of observations of the interference pattern at large angles with respect to the light path, e.g., the range of angles can include angles up to at least 10°, at least 15°, at least 20°, at least 25°, or at least 30° or can include angles of at least 35°, at least 40°, at least 45°, at least 50°, at least 55°, or at least 60°.

The invention includes apparatus for use in performing a method as described, which apparatus comprises a source of spatially coherent light, a sample holder for receiving a sample upon which to perform the method positioned in a light path from the light source, a detector for detecting light reflected from the sample over a range of angles with respect to the light path, and data processing means for receiving measurements of light intensity from the detector and for conducting an analysis thereon, wherein the analysis comprised determining a parameter of an interference pattern produced by the reflected light which parameter is quantitatively related to sample refractive index dependent variations in the intensity of reflections of light which has passed through the sample.

The data processing means can be adapted to perform an analysis which comprises one or both of: (a) the determination of the angle with respect to the light path at which there is an abrupt change in the intensity of the lighter fringes, or (b) the determination of the position of fringes of a low frequency component of the variation of intensity between the lighter and darker fringes. In a further aspect, the data processing means further comprises a processor programmed to determine a characteristic property of the fluid sample in the channel by performing a method comprising the steps of: computing an overlapping product of signal A and signal B generated from the detector, and assigning values to elements of a list R based on the overlapping product; summing a set of elements from R to produce a value q; multiplying a set of elements from R by an odd function; summing one or more products from the multiplying step to produce a value p; and calculating the shift between signal A and signal B as a function of p divided by q.

The apparatus can comprise means for controlling the temperature of the sample, e.g., a heater and/or a Peltier cooler and a temperature measuring device. As would be readily understood by one of skill, the term "back-scatter" is generally used to describe the origin of the light rays that form the interference pattern. On the basis of theoretical analysis of the origin of the interference pattern presented herein, the term "reflection" is more strictly accurate, but the phenomenon referred to by these terms is in each case the same.

In one aspect, the source of coherent light is a laser, suitably a He—Ne laser or a diode laser or VCSEL. The laser light may be coupled to the site of measurement by known waveguiding techniques or may be conventionally directed to the measurement site by free space transmission.

The measured refractive index can be indicative of a number of properties of the sample including the presence or concentration of a solute substance, e.g. a reaction product, pressure, temperature or flow rate (e.g., by determining when a thermal perturbation in a liquid flow reaches a detector).

In one aspect, the detector is a CCD array of suitable resolution.

The invention includes apparatus as described herein, wherein the sample holder is configured to allow a sample to flow there through and wherein the sample holder is connected to receive a separated sample from a sample separation device in which components of a mixed sample are separated, e.g., by capillary electrophoresis, capillary electrochromatography or HPLC. Accordingly, viewed from another perspective, the invention provides chromatography apparatus having a refractive index measuring unit as described herein as a detector.

More generally, the sample holder of the apparatus described above can be a flow through passage so that the contents of the channel may be continuously monitored to observe changes in the content thereof. These changes may include the temporary presence of cells and the out flow from the sample holder may be diverted to a selected one of two or more outlet channels according to the measurements of RI observed in the sample holder, e.g., to achieve sorting of cells in response to such measurements. The sample holder can contain a stationary analytical reagent (e.g., a coating of an antibody, oligonucleotide or other selective binding agent) and changes in the refractive index caused by the binding of a binding partner to the reagent may be observed. In view of the small sample size which it is possible to observe, the sample holder can contain a biological cell and metabolic changes therein may be observed as changes in the refractive index of the cell.

In one aspect, the invention relates to a method for performing a measurement of refractive index comprising directing a coherent light beam along a light path to impinge on a first light transmissive material and pass there through, to pass through a sample which is to be the subject of the measurement, and to impinge on a further light transmissive material, the sample being located between the first and further materials, detecting reflected light over a range of angles with respect to the light path, the reflected light including reflections from interfaces between different substances including interfaces between the first material and the sample and between the sample and the further material which interfere to produce an interference pattern comprising alternating lighter and darker fringes spatially separated according to their angular position with respect to the light path, and conducting an analysis of the interference pattern to determine there from the refractive index, wherein the analysis comprises observation of a parameter of the interference pattern which is quantitatively related to sample refractive index dependent variations in the intensity of reflections of light which has passed through the sample. The first material and the further material can comprise the same substance or different substances. The sample can be contained in a flow channel having a cross-sectional depth of, for example, up to 1 mm in the direction of the light path. For example, the sample can be contained in a capillary tube.

In a yet further aspect, the analysis comprises one or both of: (a) the observation of the angle with respect to the light path at which there is an abrupt change in the intensity of the lighter fringes, or (b) the observation of the position of these fringes of a low frequency component of the variation of intensity between the lighter and darker fringes. In a still further aspect, at least one the interface involving the sample at which light is reflected is curved in a plane containing the light path, the curved interface being convex in the direction facing the incoming light if it is the interface between the first material and the sample and being concave in the direction facing the incoming light if it is the interface between the sample and the further material.

In one aspect, the invention relates to an apparatus for use in performing a measurement of refractive index, which apparatus comprises a source of coherent light, a sample holder for receiving a sample upon which to perform the method positioned in a light path from the light source, the sample holder providing a first interface between the sample holder and a sample receiving space in the sample holder and a second interface between the sample receiving space and the sample holder, the first and second interfaces being spaced along the light path, a detector for detecting light reflected in use from a the sample over a range of angles with respect to the light path, the reflected light including reflections from the first and second interfaces which interfere to produce and interference pattern comprising alternating lighter and darker fringes spatially separated according to their angular position with respect to the light path, and data processing means for receiving measurements of light intensity from the detector and for conducting an analysis thereon, wherein the analysis comprises determining a parameter of the interference pattern produced by the reflected light which parameter is quantitatively related to sample refractive index dependent variations in the intensity of reflections of light which has passed through the sample.

In a further aspect, the data processing means is adapted to perform an analysis which comprises: the determination of the position of the fringes of a low frequency component of the variation of intensity between the lighter and darker fringes.

In a further aspect, the data processing means is adapted to perform an analysis which comprises the determination of the angle with respect to the light path at which there is an abrupt change in the intensity of the lighter fringes.

In a further aspect, the data processing means is adapted to perform an analysis which comprises the determination of the angle with respect to the light path at which there is an abrupt change in the intensity of the lighter fringes and comprises the determination of the position of the fringes of a low frequency component of the variation of intensity between the lighter and darker fringes.

In a further aspect, the data processing means is adapted to perform an analysis which comprises one or both of: (a) the determination of the angle with respect to the light path at which there is an abrupt change in the intensity of the lighter fringes, or (b) the determination of the position of these fringes of a low frequency component of the variation of intensity between the lighter and darker fringes, and wherein the sample holder locates the sample between a first material defining the first interface with the sample and a further material defining the second interface with the sample, which first and second materials are composed of the same substance.

In a further aspect, the sample holder is so constructed that at least one of the first and the second interfaces is curved in a plane containing the light path, the curved interface being convex in the direction facing the incoming light if it is the interface nearer the light source in the light path and being concave in the direction facing the incoming light if it is the interface more distant from the light source in the light path.

Figure 8:
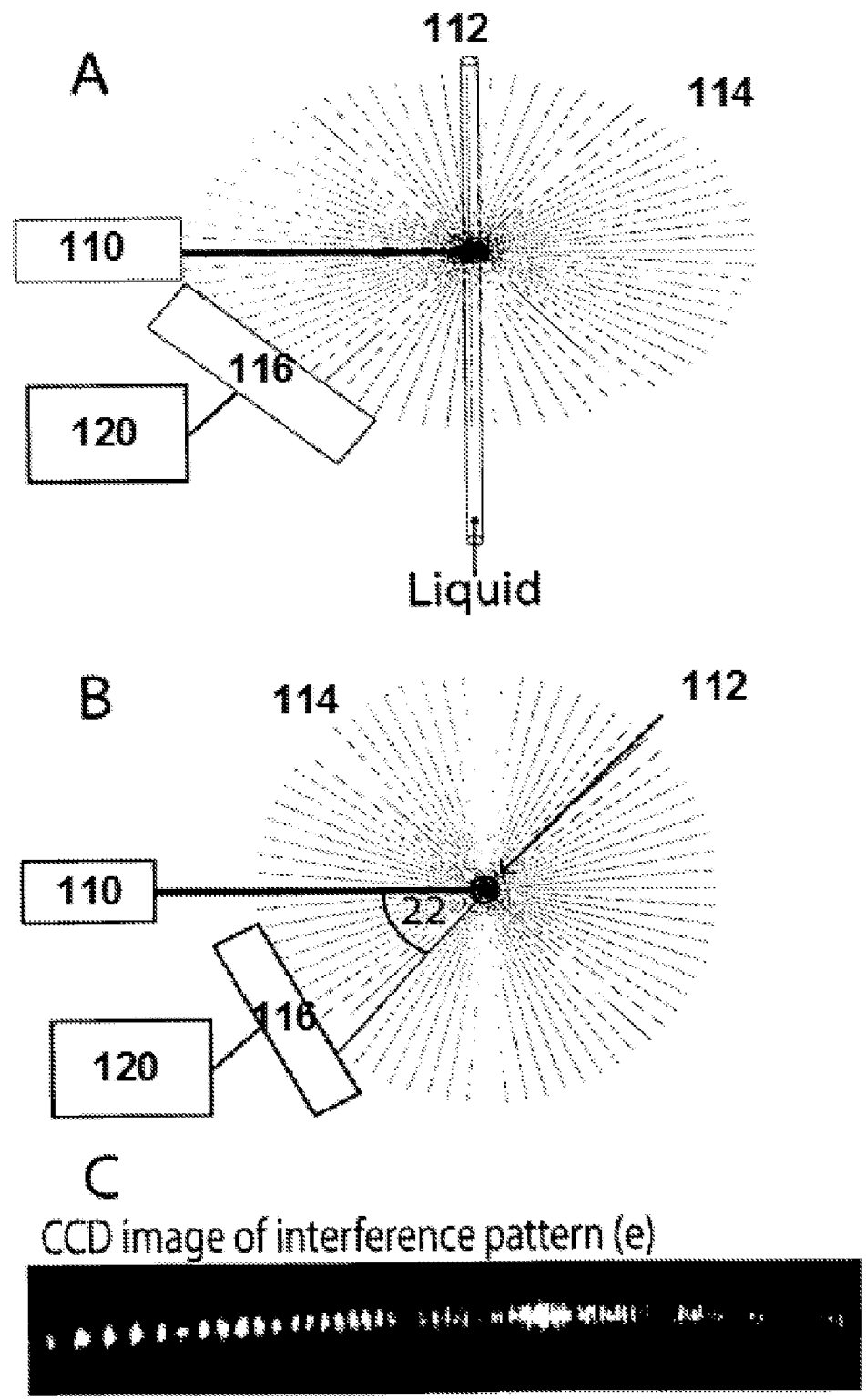
FIG. 8 shows a schematic view of a suitable Back-Scattering Interferometry (BSI) experimental setup seen in isometric view (A) and in plan view from the top (B) with a typical interference pattern shown at (C).

A typical BSI scheme as previously known is shown in FIG. 8. The system consists of a laser 110 that impinges its beam on a capillary tube 112 filled with a liquid of which one wants to measure refractive index, thereby creating an interference pattern 114. This interference pattern, which changes with changes in the liquid's refractive index, is then measured using a CCD detector 116. A typically observed interference pattern in the reflection direction is seen in C. This is analyzed by data processing means 120.

The demonstrated sensitivity of $10^{-7}$ is reached by following the displacement of the individual light fringes of the interference pattern within 0.3 angular degrees [Swinney, K; Markov, D; Bornhop, D. J; Review of Scientific instruments, 2000, 71, 2684 2692.] from the directly back reflected direction, as one changes the refractive index of the liquid. The fringe pattern is periodic in refractive index space with a period of the order of $10^{-3}$. This limits the dynamic measurement range to the order of $10^{-3}$, which for many purposes requires additional knowledge about the absolute value of the refractive index.

As the measurement monitors a displacement of the fringe pattern, it is inherently a differential measurement, employing calibration both for the absolute level of the refractive index as well as for the differential factor. This factor describes the fringe movement corresponding to a given change in the refractive index.

The dynamic range of the BSI system may be increased by taking into account other variations of the interference pattern with changing refractive index than those previously considered. The dynamic range is increased without compromising the high differential sensitivity previously reported [Swinney, K; Markov, D; Bornhop, D. J; Review of Scientific instruments, 2000, 71, 2684 2692.]. Theoretical description of the BSI scheme has been improved to include an extended optical ray tracing model that matches the range in angular and refractive index space of the experiments, thus providing new information about the structure of the reflected light interference pattern. In contrast to the previously proposed model [Tarigan, H. J; Neill, P. Kenmore, C. K; Bornhop, D. J. Anal. Chem., 1996, 68, 1762 1770.], this model is capable of explaining all frequency components that appear in the interference pattern. Furthermore, the model has been used to predict an abrupt change in the intensity of the reflected light interference fringes, which depends uniquely on the absolute value of the refractive index of the probed sample. Moreover, this feature has been experimentally confirmed. The improved understanding of the BSI system provides two preferred approaches to an absolute measurement of the refractive index of samples, which are preferably liquids in the refractive index range between water (1.33) and glass (1.50). The first approach is based on the measurement of the depth of modulation of the interference pattern caused by variations in the Fresnel coefficients. The second approach is based on the measurement of the total internal reflection angle within the capillary or other sample container.

Previously systems of similar geometry to the BSI scheme have been modeled by obtaining solutions to Maxwell's equations governing light propagation [Pedrotti, F. L; Pedrotti, L. S. Introduction to optics, 2nd ed.; Prentice-Hall New Jersey, 1996; Chapter 27.]or by optical ray tracing. Kerker and Matijevic [Kerker, M; Matijevic, E. J. Opt. Soc. Am., 1961, 51, 506-508.] made the first complete model based on solutions to Maxwell's equations describing two concentric cylinders. Watkins confirmed these results experimentally [Watkins, L. S; J. Opt. Soc. Am., 1974, 64, 767-772.]. However Watkins considered optical glass fibers with thick claddings and therefore obtained results significantly different to those observed in BSI, as the interference pattern is described not to be dependent on the refractive index of the core in the back-scatter angle regime. Marcuse and Presby [Marcuse. D; Presby, H. M. J. Opt. Soc. Am., 1975, 65, 367 375.] extended this model to also take into account the case of a thin cladding of the fibers. From their results, an abrupt change in the back-scattered light intensity pattern is observed. However, it was not realized that this abrupt change could be utilized to obtain the absolute refractive index with high precision, since they were attempting to determine the outer radius of the glass fiber, and they were not concerned with the core index. The position of the abrupt change depends on the core index. Horton and Williamson [Horton. R; Williamson, W. J. J. Opt. Soc. Am., 1973, 63, 1204 1210.] made a ray tracing model of an optical fiber obtaining information about the ratio between inner and outer radii of the fiber. The approach they used is a back calculation assuming a planar wave front of the output. The rays considered in their model are not the same as in the present model, as they consider fibers with a thick cladding, and make use of multiple reflections inside the cladding. This is due to the fact that they use significantly different refractive indices of the core than those considered in BSI. The BSI system has been modeled using a ray-tracing model by H. Tarigan et al. [Tarigan, H. J; Neill, P. Kenmore, C. K; Bornhop, D. J. Anal. Chem., 1996, 68, 1762-1770.]. However, their model is limited by considering only small angle back-scattered light (0.3 degrees).

The present model has been extended to include reflection angles up to 90 (side reflections). This is done in the geometric optics regime by using Snell's law:

$$n_i \times \sin(\theta_i) = n_j \times \sin(\theta_j) \tag{1}$$

where $n_i$ and $n_j$ are the refractive indices of the media and $\theta_i$ and $\theta_j$ are the angles of light propagation in the respective media. Furthermore the law of reflection, $|\theta_{in}|=|\theta_{out}|$, is used. For angles beyond a few degrees it is not possible to use the assumption ($\sin \theta \approx \theta$) done by Tarigan et al. This implies that a simple analytical equation cannot be obtained. The present model traces six beams, see FIG. 9, through the system and calculates their interference in a detection plane placed in the far field region. For each type of beam a number of rays (typically 1000) are traced. The information carried along with each ray is its position, angle, intensity and phase. At the detection plane the interference is calculated based on the information packages of all rays. The six beams considered in the model interfere by:

$$I_{ij} = 2\sqrt{(I_i \times I_j)} \times \cos(\rho_i - \rho_j) \tag{2}$$

where I is the intensity and $\rho$ is the phase of each individual ray, and i and j are indices for each ray, respectively. The model is developed to also take into account the polymer coating on the capillary, thus requiring six beams. The model assumes circular geometry of the capillary and that the laser can be described by plane waves.

The model assumption of circular geometry of the capillary is justified by the observation that no significant change in the pattern was observed during rotation of the capillary (TSP100170, Polymicro Technologies) along the capillary axis. The tilt of the wave front from the laser (05-LHR-HeNe, Melles Griot) was analyzed using a beam analyzer (CLAS-2D, Wave Front Sciences) and was observed to be less than 0.01 micro radians, thus justifying the assumption of a planar wave front. The smallest spacing of refractive index changes is the thickness of the coating of 12 micrometer.

Therefore the assumption of geometrical optics being adequate is justified since the wavelength used (632.8 nm) is much smaller than the distances otherwise present in the system.

In what follows, modeling and experimental work is based on the use of apparatus as shown in FIG. 8. The BSI experiments were done by mounting the capillary on a translation stage and making a He—Ne laser beam impinge perpendicularly on the capillary. The reflected or backscattered light was collected using a screen and a CCD camera (C4742-95, Hamamatsu). Requirements for the laser include a coherence length of at least about twice the diameter of the capillary and a wavelength at which the capillary is substantially transparent. Requirements for the detector include high one-dimensional spatial resolution and an adequate intensity resolution, depending on the application. Passive temperature control consisting of a large thermal reservoir (an aluminum block) thermally connected to the capillary was used to stabilize temperature. Temperature fluctuations affect the refractive index of the liquid substantially. Active temperature control is only needed if the detection of changes in refractive index of less than $10^{-5}$ is required. In this work, passive temperature stabilization is adequate, as the refractive index fluctuations in the system caused by temperature fluctuations in a controlled environment are on the $10^{-5}$ scale, corresponding to 0.1° C. temperature fluctuations for water.

Figure 10:
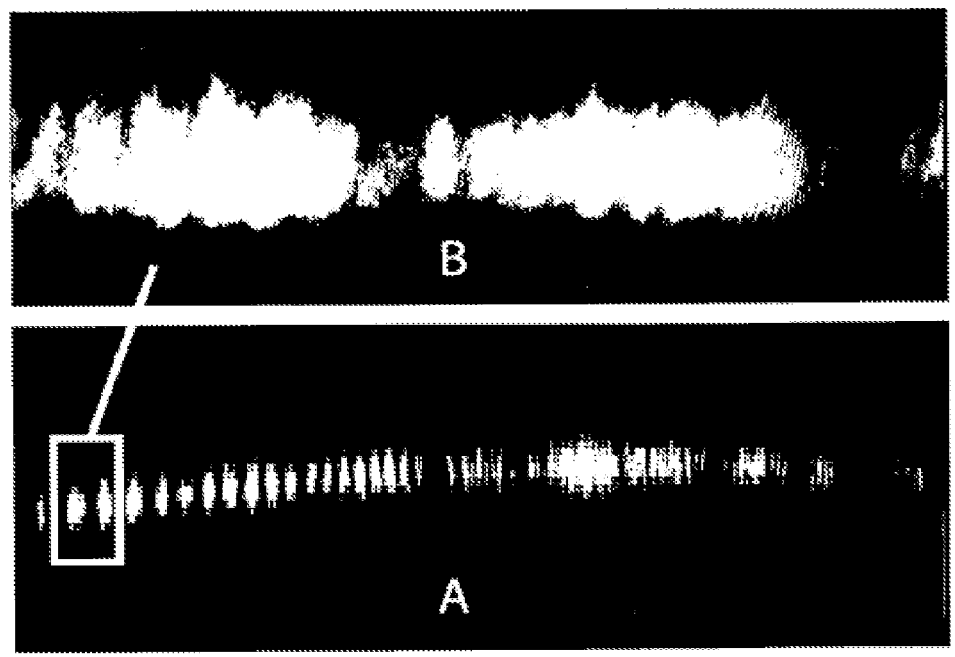
FIG. 10 shows CCD camera images of a typical BSI interference pattern (A, B).
Figure 11:
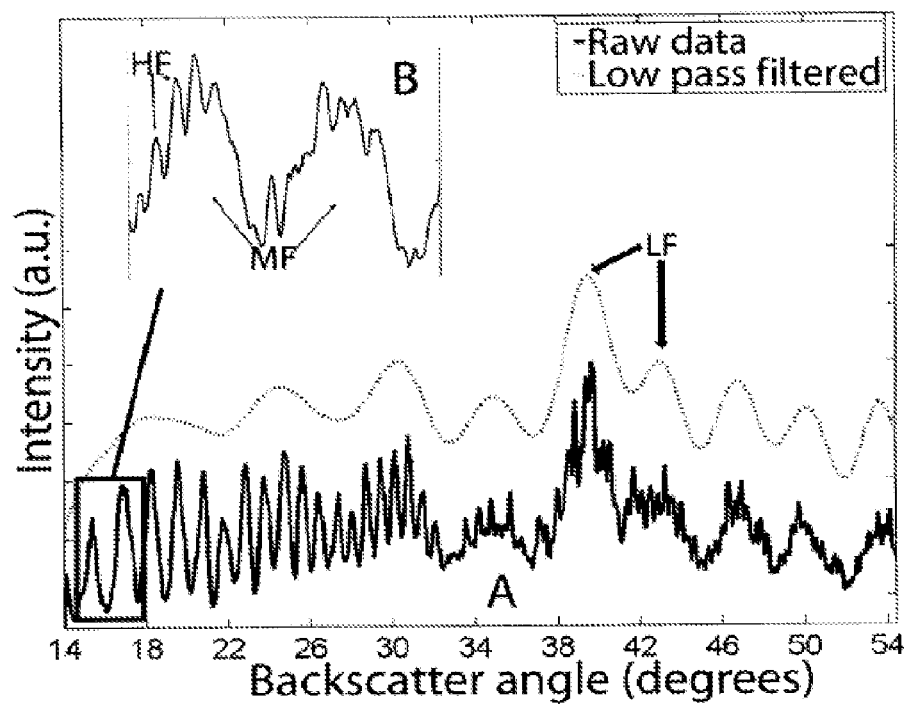
FIG. 11 shows line profiles (A, B) corresponding to interference patterns A, B respectively of FIG. 10.
Figure 14:
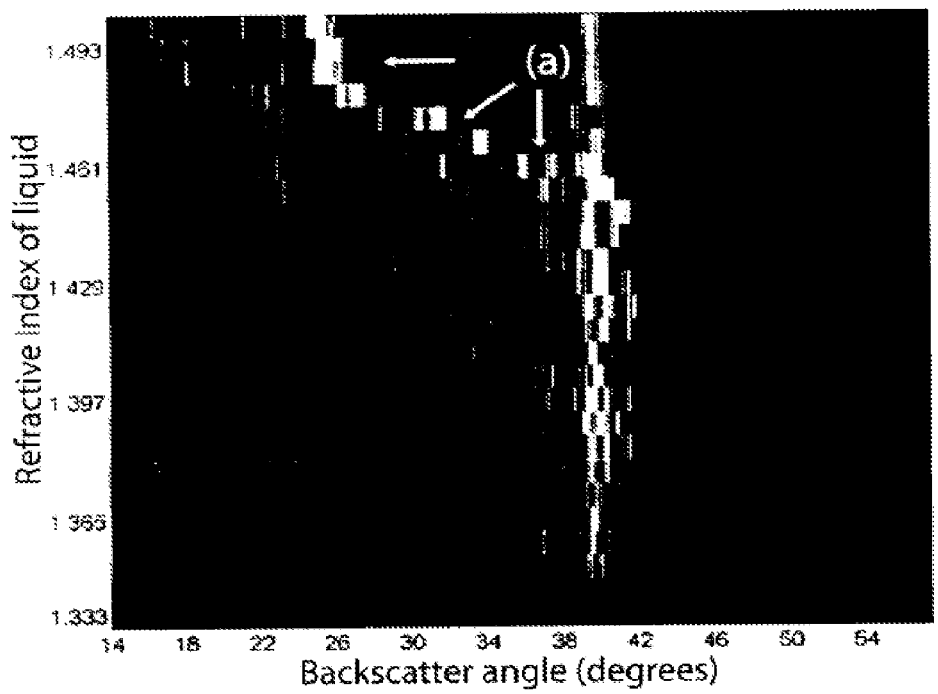
FIG. 14 shows experimentally obtained data from a 100 μm ID/165 μm OD/12 μm coating capillary showing the low frequency variations of the interference pattern as the refractive index is varied.

The capillaries used in the experiments were purchased from Polymicro Technologies (AZ, US). Two sizes of capillaries have been used. The dimensions of the capillaries are 100 μm inner diameter (ID), 165 μm outer diameter (OD) with a 12 μm thick polyimid coating (TSP100170) and 542 μm ID, 673 μm OD with a 24 μm thick polyimid coating (TSP530660), respectively. In the experiments, the refractive index was changed from 1.33 to 1.5 by using both sucrose (Sigma Chemicals Company) and NaSCN (Merck) aqueous solutions. The RI of the solutions was measured in a refractometer (R L3, Polskie Zaklady Optyczne, Warsaw) immediately after the sample had been injected into the capillary. A typical interference pattern thus obtained is shown in FIG. 10A, with corresponding line profile of the intensity shown in FIG. 11A. In FIG. 10B two of the fringes in 3A are enlarged, showing a finer structure. A line profile of the intensity from 3B is seen in 4B. The visual appearance is enhanced by low pass filtering, a Fourier filter, of the raw data. The raw data and the low pass filtered data have been offset for clarity. It is seen that the intensity pattern contains multiple frequency components. The period of the fringe pattern corresponding to medium frequency (MF) components is shown in FIG. 11B. Similarly, the period of the fringe pattern corresponding to low frequency (LF) components is shown in FIG. 11A. In the following, frequency components are referred to as frequencies. Under certain circumstances, one is able to observe a more closely spaced component, or ripple, of the intensity profile, here denoted high frequency (HF) variations. As one increases the refractive index of the liquid in the capillary, the intensity profile shifts towards lower reflection angles, see FIG. 14. However, the high frequency variation component is spatially fixed and does not move as one changes the refractive index, in accordance with previous observations [Markov, D; Swinney, K; Norville, K; Lu, D; Bornhop, D. J. Electrophoresis, 2002, 23, 809 812.].

By investigating the experimentally observed frequencies of the fringe pattern, it may be shown by geometrical considerations that the distance between the origin points of the interfering rays (points a through f in FIG. 9) on the capillary are approximately five to ten times larger in the high frequency case than in the medium frequency case. By using geometrical considerations, it is possible to calculate the distance between origins of the interfering rays for all frequency components. It was found that the distance required to produce the high frequency variations is on the order of the capillary diameter. This indicates that the rays responsible for this high frequency variation are scattered from the edges of the capillary, thereby not being affected by the liquid within the capillary. This fits the observed behavior well, since the high frequency component is not observed to be displaced as one changes the refractive index of the liquid in the capillary.

Figure 9:
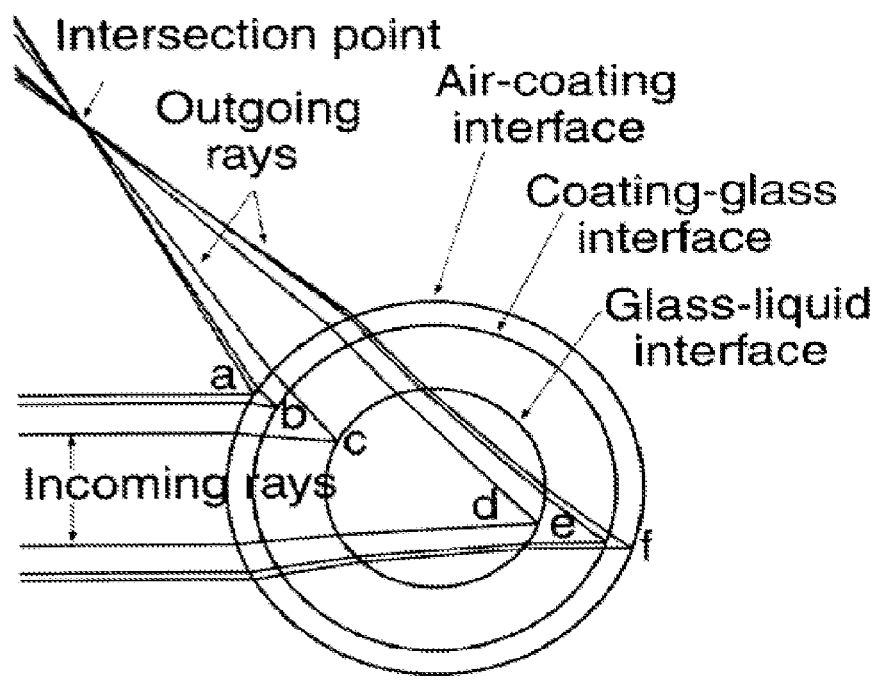
FIG. 9 is a view of the cross-section of the capillary of FIG. 8 showing the ray paths through the capillary system.

The low frequency component is spatially stationary as well, since this component is caused by the common interference between the three rays reflected from the front of the capillary (points a through c in FIG. 9), as well as the common interference between the three rays reflected from the back of the capillary (points d through f in FIG. 9). The displacement of this component is zero for the part originating from the front, since these rays do not traverse the liquid and thus experience the same optical path length by different refractive indices of the liquid. For the second part the displacement is small, because all three rays experience almost the same change in optical path length traversed relative to each other.

In contrast to the high and low frequency components, respectively, the medium frequency component originates from the interference between rays reflected at the front (points a c in FIG. 9), and at the back of the capillary (points d through f in FIG. 9). These rays experience a large relative change in optical path length traversed, as the rays from the front do not experience a change in optical path length whereas the rays reflected from the back do. It is this relative change in the optical path length between different paths that causes the movement of the medium frequency component of the interference pattern as refractive index changes, yielding the ultra-high sensitivity previously described.

Figure 12:
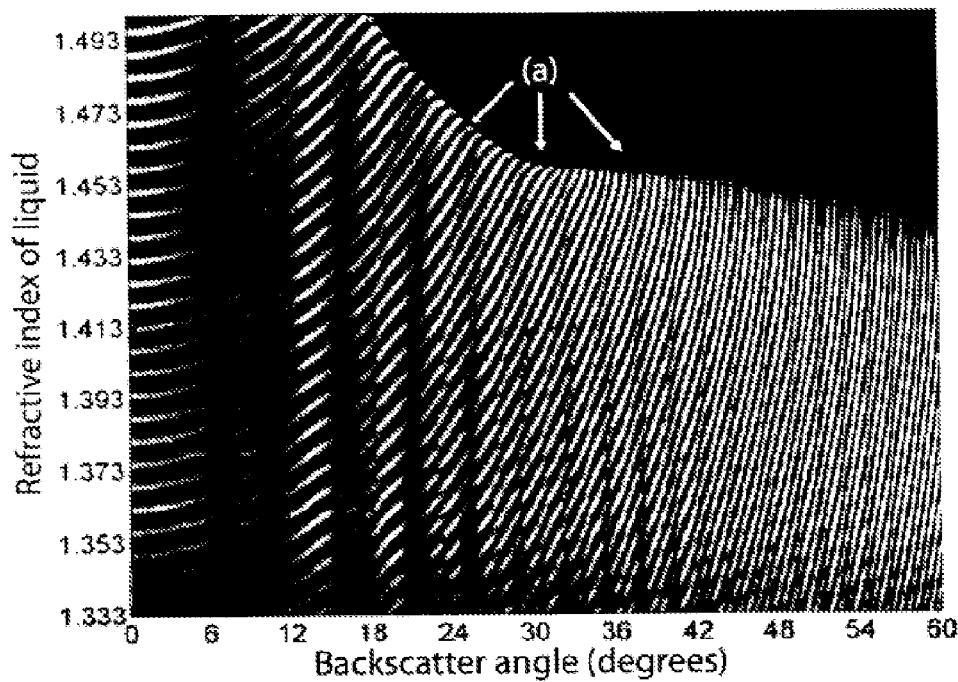
FIG. 12 shows model predictions of the angle dependent variations in the reflected light intensity in the plane perpendicular to the capillary tube of FIG. 8.
Figure 13:
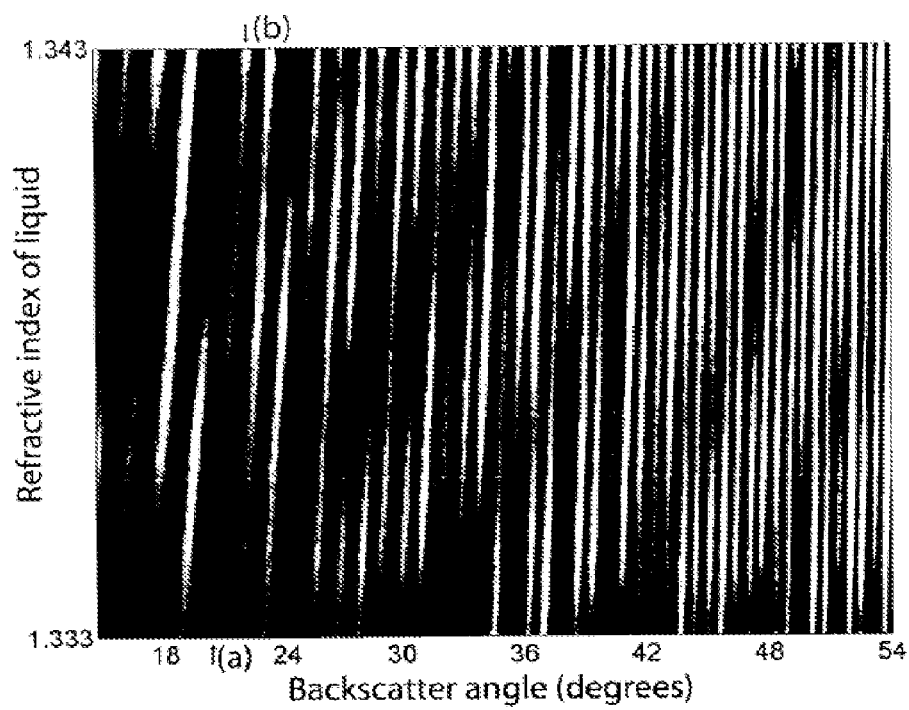
FIG. 13 shows a calculated pattern for a smaller refractive index range from a 100 μm ID/165 μm OD/12 μm coating capillary.

The results from the model are plotted in FIG. 12 and FIG. 13 as function of reflection angle and refractive index of the liquid for a 100 μm ID/165 μm OD/12 um coating capillary. The results have been compiled in this plot by stacking such line plots for closely spaced liquid refractive indices into a two-dimensional overview of the reflection behavior. This plot corresponds to 1643 injections of liquid with different refractive indices. Bands of light (fringes) move towards larger reflection angles as the refractive index is increased. Overlaying vertical band structures of higher and lower light intensity are seen. These structures do not move as the refractive index is changed. An abrupt change in the intensity level (a) is seen moving towards lower back-scattering angles for refractive indices of the liquid above 1.45. The grayscale represents the intensity of the pattern in the given reflection angle for the given refractive index of the liquid in arbitrary units. In FIG. 13 the movement of the fringes at a reflection angle of 20° is measured to be approximately 2.1° per 0.01 refractive index change, measuring from (a) to (b).

Figure 15:
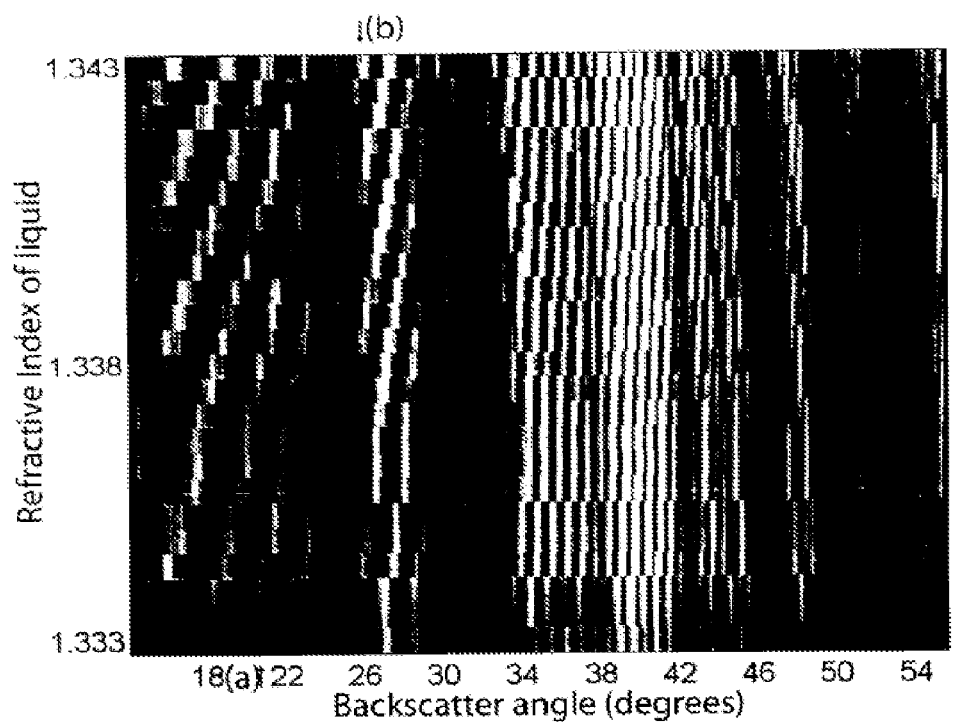
FIG. 15 shows experimentally obtained data for dilute sucrose solutions in a 100 μm ID/165 μm OD/12 μm coating capillary.

Experimentally obtained data are plotted the same way as the model and the results are shown in FIGS. 7 and 8. Here 25 measurements of the interference pattern have been made, each at different refractive index. At each refractive index level a line profile of the interference pattern has been obtained. These measurements have been stacked vertically into one figure. In FIG. 15, the refractive index interval between measurements is less than the change required to move a fringe one fringe-width, thus allowing one to monitor the medium frequency fringes as continuous bands. The movement of these fringes varies with reflection angle. For a reflection angle of 20 this movement is measured to be 4.0 per 0.01 refractive index change, measuring from (a) to (b). Low frequency variations are seen as vertical light bands.

These fringes do not appear to form continuous bands in the vertical refractive index dependent direction due to the large change in refractive index between measurements. An abrupt change in the intensity (a) is seen for high refractive indices (above 1.43), which moves towards lower reflection angles for increasing refractive index.

At each refractive index a line profile of the intensity of the interference pattern has been made. Each line profile has been extended vertically. The extended line profiles have been stacked into a single plot. These figures are used to directly compare the model and the experiment. In the BSI experiments two sets of fringes are always present. The fringes moving outwards (medium frequency) with increasing refractive index are measured to move 4.0° when the refractive index is changed by 0.01 at a reflection angle of 20° (a, b in FIG. 15). The model predicts a movement of 2.1° (a, b in FIG. 13). These are the fringes traditionally used for measuring refractive index using the BSI technique. This model predicts both low frequency and medium frequency variations of the pattern. These frequencies will be discussed below. The low frequency fringes are not moving significantly with changing refractive index. The model predicts no movement of these fringes. The number of these fringes in the model is 13 and in the experiment 10 fringes are observed within a range of reflection angles from 14 to 54°. Both model and experiment shows an abrupt change in intensity at large reflection angles. This abrupt change in intensity is somewhat displaced in the modeled results compared to the experimental results, but it is within experimental error. The movement of this abrupt change in intensity in experiments qualitatively agrees with modeling of the BSI system—the model predicts the behavior of the BSI system qualitatively. The predictions of the model have been used to select the proper capillary dimensions for applications of the BSI technique.

A first preferred aspect of the invention performs absolute measurement of refractive index based on Fresnel coefficients. Even though the low frequency variations remain stationary in terms of reflection detection angles, their intensity changes as the refractive index of the liquid changes. As the intensity of the rays are in part determined by the Fresnel coefficients of the surface of reflection, the system can be configured in such a way that the intensity of the low frequency component can be used as a measure for the refractive index on a coarser scale. This may be done by either index matching the coating and the glass tubing, thereby eliminating the reflection from the coating-glass surface (points b and e in FIG. 9) or by stripping the coating off the capillary. The low frequency component is then caused by interference between two rays; the ray reflected by the air-coating (points a and f in FIG. 9); or air-glass interface (points b and e if the coating is removed) and the ray reflected from the glass-liquid interface (points c and d in FIG. 9). Since the intensity of this last ray is determined by the Fresnel coefficients of this surface consisting of glass with constant refractive index and the liquid to be probed, the absolute value of the refractive index of the liquid may be calculated from the relative intensity of the two rays, which is given by the depth of modulation of the low frequency component. This is possible if the refractive index of the air, glass, and coating is known. If one wants to measure depth of modulation to a certain degree, one needs at least this degree of intensity resolution in the detection system. Since the CCD camera used in these examples has 255 intensity levels, more refractive index resolution than the difference in refractive index between air and glass divided by the number of detectable intensity levels, which corresponds to $5 \times 10^{-3}$, cannot be acquired without the disclosed improved methods. A camera with a larger number of intensity levels can alternately be used.

Figure 19:
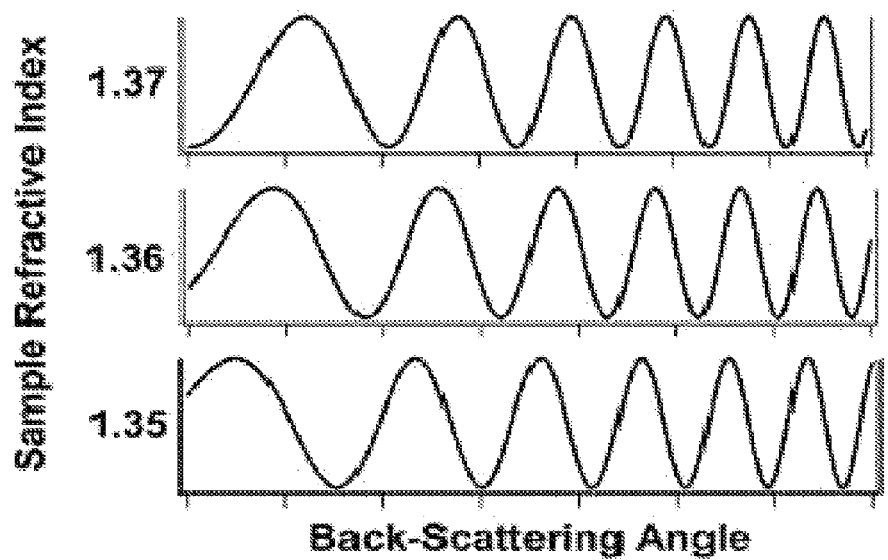
FIG. 19 shows model low frequency component plots for three different refractive index samples.

However, FIG. 19 shows model LF plots (similar to that marked in FIG. 10) calculated for liquids of three different refractive indices. It can be seen that the lateral position of the fringes are dependent on the refractive index, but that the amplitude does not change based on refractive index.

A second preferred aspect relies on the dependence on refractive index of the critical angle at which total internal reflection occurs. The model predicts an abrupt change in intensity moving towards lower reflection angles as the refractive index of the liquid approaches the one of the glass tubing, see line marked by (a) in FIG. 12. This feature of the interference pattern is also observed experimentally (see (a) in FIG. 14) and agrees with the predicted feature in position-refractive index space within experimental error. A feature similar to this has been reported for optical glass fibers [Horton R.; Williamson, W. J.; J. Opt. Soc. Am., 1973, 63, 1204 1210.]. However these fibers have a different optical configuration, and the mechanisms responsible are different. In the case of optical glass fibers the mechanism responsible is grazing of a certain ray on the core of the fiber being dependent of the inner radius of the glass fiber. Without wishing to be bound by theory, it is believed that the mechanism giving rise to the phenomenon in BSI is total internal reflection in the wall of the capillary, being dependent on the refractive index of the liquid in the capillary. The main source of error is the dimensions of the capillary, which have an uncertainty of 6 µm for the 100 µm ID/165 µm OD/12 um coating capillary according to the manufacturer. The way of determining the absolute value of refractive index on a coarser scale is to look at this feature of the pattern. Both the model and the experiment show an abrupt change in light intensity at higher reflection angles, and the position of this change varies with refractive index. However, using a 100 µm ID/165 pm OD capillary this change takes place at refractive indices 1.40 to 1.50, which is not the measurement range typically of interest for bio analytical applications. Most dilute aqueous solutions of biological relevance have refractive indices in the range from 1.33 to 1.40. By using this model, one is able to calculate the dimensions of the capillary required to make the abrupt intensity change occur in position/refractive index space at refractive indices above 1.33 and at reflection angles inside our measurement range. The mechanism responsible for this abrupt change in intensity is, according to the model, total internal reflection of the rays reflected from the back of the capillary, preventing these rays from being scattered to larger reflection angles, thereby causing a sudden decrease in the intensity of the light at a given limiting angle. This angle varies uniformly with the refractive index and can therefore be used as a measure for the refractive index of the liquid.

Figure 16:
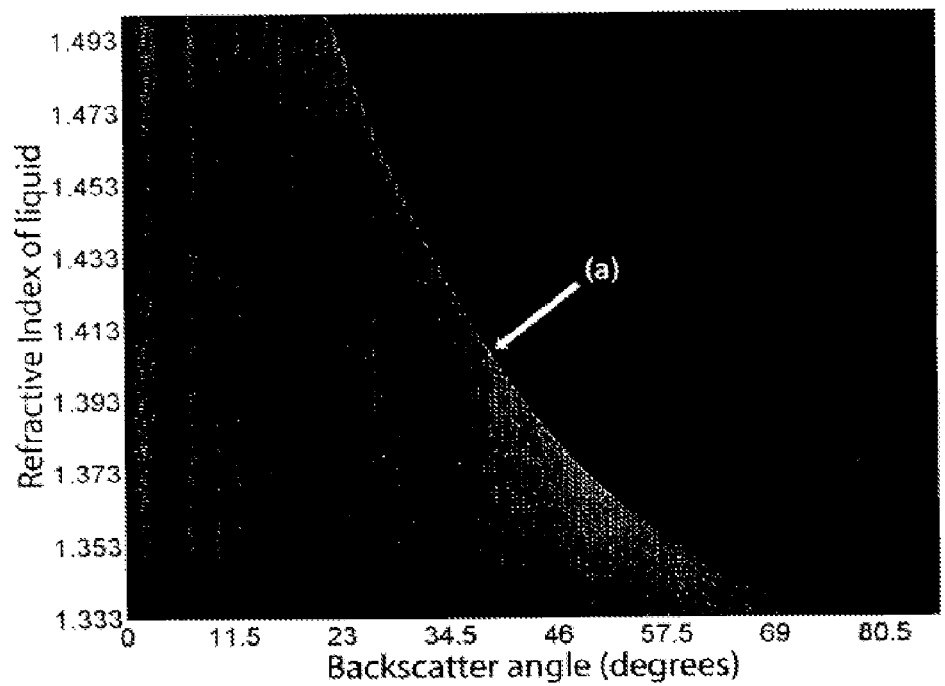
FIG. 16 shows a calculated pattern for a 542 μm ID/673 μm OD/24 μm coating capillary as function of reflection angle and refractive index of the liquid.
Figure 17:
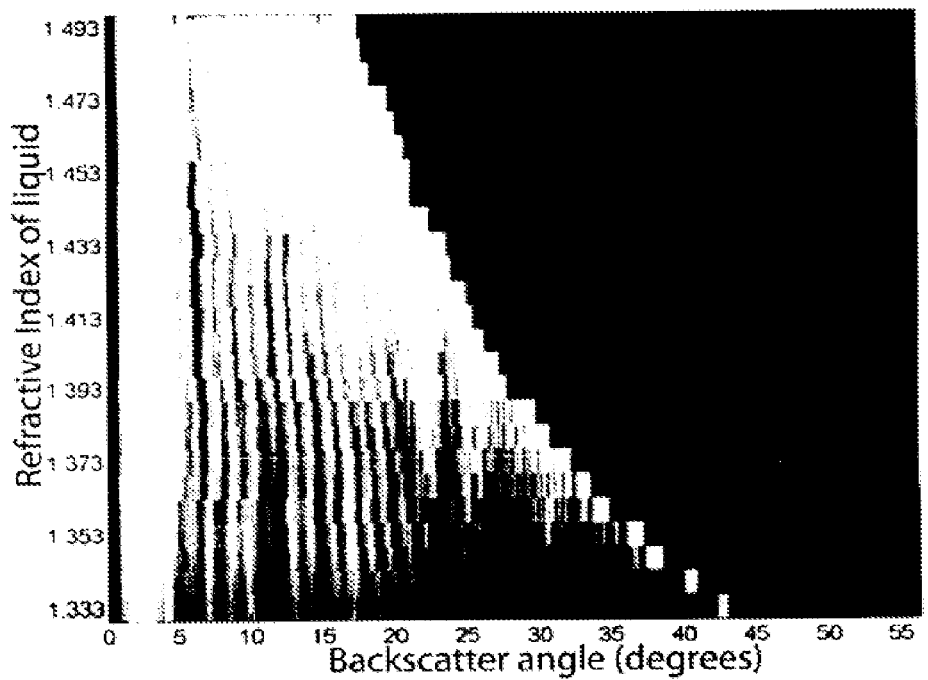
FIG. 17 shows an experimentally obtained pattern for a 542 μm ID/673 μm OD/24 μm coating capillary.
Figure 18:
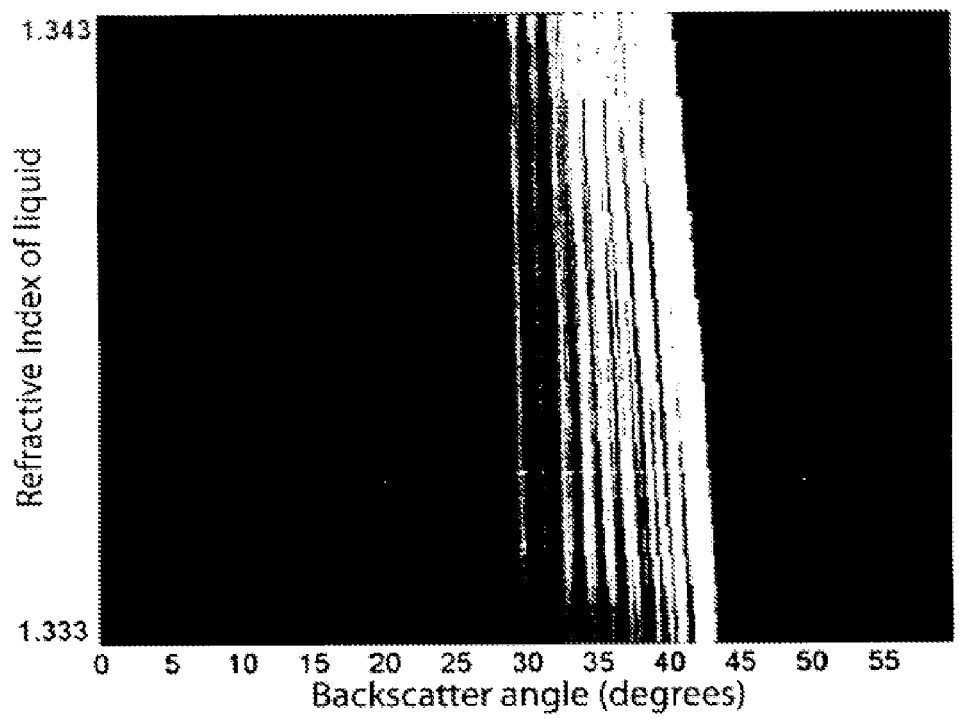
FIG. 18 shows experimentally obtained data from a 542 μm ID/673 μm OD/24 μm coating capillary.

The modeled interference pattern as function of refractive index for a 542 µm ID/673 µm OD/24 um coating capillary is shown in FIG. 16. FIG. 17 shows the experimental results from using a 542 µm ID/673 µm OD/24 um coating capillary. It is seen by comparison to FIG. 16 that the position of the abrupt change in intensity differs from the model, although the behavior is quantitatively the same. Both low and medium frequency variations as well as the abrupt change in intensity level at high reflection angles are seen. The abrupt change in intensity for this capillary occurs in a more relevant interval for dilute aqueous solutions, than it does for the 100 µm ID/165 µm OD/12 µm coating capillary, as indicated by (a).

The experimental and the modeled results show good agreement. The abrupt change in interference pattern is already detectable at the refractive index of water and is experimentally accessible well beyond refractive indices normally considered for aqueous solutions; see point (a) in FIG. 16. The discrepancy between the predicted and the measured angles of the abrupt intensity change may be attributed to material parameter tolerances of the experimental set up as follows: The uncertainty of the dimensions of this capillary is 12 µm and 25 gm for the inner and outer diameter, respectively. This gives an uncertainty of 6.9° in the angle predicted by the model. The uncertainty in refractive index of the polyimide coating (n=1.5 to 1.8) can cause a further uncertainty in the predicted angle of 3.3°. In FIG. 17, the position of the abrupt change in intensity is monitored as function of refractive index of sucrose solutions. The detection limit for refractive index changes achieved by following the position of this change in position is $2.5 \times 10^{-4}$. From the experiments resulting in FIG. 17, the precision is found to be $2.5 \times 10^{-4}$. Hence an absolute refractive index measurement with accuracy on this level on a nanoliter volume can be performed. The main limitations for accuracy such as temperature control and detector resolution are the same as conventional BSI. Theoretical limit using this approach is therefore similar to the limit achievable by conventional BSI.

There are at least two possible ways of making absolute measurements of the refractive index of liquid in nanoliter probe volumes in a simple optical setup. The improved model based on ray tracing has been used to reveal and explain novel features of the interference pattern: An abrupt change in intensity at large reflection angle is clearly present in the modeled system and in the experimental results. It is shown that this approach enables an absolute determination of the refractive index in the range from 1.33 to 1.5 by using capillary tubes of appropriate dimensions. It has been proven that the model based on ray tracing may be used for describing the BSI phenomenon. The improved ray tracing model is capable of explaining all the significant features of the BSI pattern except the stationary high frequency fringes. However, these fringes have been shown to originate from reflections from the edges of the capillary and thereby not being relevant for measuring the refractive index of the liquid within. These improvements of the BSI scheme can contribute significantly to enhance future applicability of the methodology for analysis of minute volumes of aqueous solutions.

D. Detection of Chemical Events

The disclosed systems and methods can be used in connection with the detection and determination of a wide variety of characteristic properties of a sample. For example, the invention can be used to determine absolute or relative refractive index (RI) of a sample, for example a fluid either flowing or static. The disclosed systems and methods can also be used in connection with detection and determination of chemical events, for example label-free analysis of hybridization reactions such as DNA-DNA binding reactions. The disclosed systems and methods can also be used in bioassays, monitoring enzymatic activity, drug screening, and clinical diagnostics.

In one aspect, the disclosed methods can be performed wherein the characteristic to be determined is whether first and second biochemical functional species (i.e., first and second analytes) bind with one another, and the step of introducing a sample to be analyzed into the first rectangular channel comprise introducing the first biochemical functional species into the channel and then introducing the second biochemical functional species into the channel to facilitate a binding reaction between the first and second biochemical species. For example, the first and second biochemical functional species can be selected from the group comprising complimentary strands of DNA, complimentary proteins, enzyme-substrate pairs, and antibody antigen pairs. That is, in a further aspect, the characteristic to be determined can be a label-free analysis of a hybridization reaction in the channel. In a yet further aspect, the positional shifts in the light bands can correspond to a chemical event occurring in the sample.

Examples of chemical events that can be detected and bioassays conducted with the disclosed systems and methods include a binding event between one or more of antibody-antigen, protein-protein, small molecule-small molecule; small molecule-protein, drug-receptor; antibody-cell; protein-cell; oligonucleotide-cell; carbohydrate-cell; cell-cell; enzyme-substrate; protein-DNA; protein-aptamer; DNA-DNA; RNA-RNA; DNA-RNA; protein-RNA; small molecule-nucleic acid; biomolecule-molecular imprint (MIP); biomolecule-protein mimetic; biomolecule-antibody derivatives (SCFV, Fab, FC, etc.); lectin-carbohydrate; and biomolecule-carbohydrate.

In one aspect, the disclosed systems and methods can be used in connection with a step of performing a chromatographic separation or an electrophoretic separation on the sample prior to the determining the characteristic property step.

1. Analytical Detection Events

The invention also finds use as a detector for other chip-scale analytical schemes including electrophoresis, μ-HPLC separations and FIA. It is possible to detect molecules important to cellular function, high throughput analysis, and pharmaceutical screening. The interferometer can also be used in biochemical assays and to quantify environmental analytes. It is also possible to perform micro-thermometry, the device has the capability of measuring small temperature changes (in the $10^{-3\circ}$ C. range) allowing for cellular respiration, protein folding, calorimetry, and fundamental chemical binding studies to be performed in picoliter volumes. Furthermore, when using special surface chemistry to selectively bind solutes, such as DNA oligomers, proteins, or antibodies, without sacrificing specificity/sensitivity. Use of the device to perform flow sensing, pressure sensing, time resolved enthalpies and perform detection for products eluted from focusing techniques such as flow cytometry is also viable, as well as ability to monitor label-free reactions and to quantify the interference brought on by fluorescent markers normally attached to biomolecules.

2. Determination of Kinetic Parameters

Figure 22:
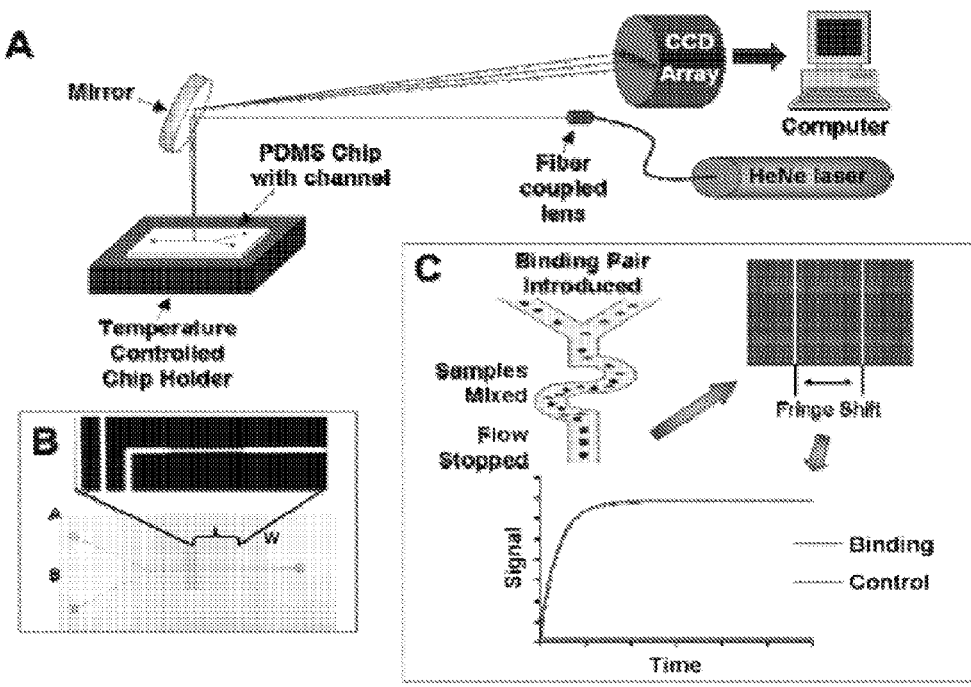
FIG. 22 shows A) Experimental setup for BSI, B) Microfluidic chip with serpentine mixer and restriction, C) Photograph of representative fringe patterns showing a RI induced position shift of the fringes, a cartoon representation of a binding event and observed signal for a control and reactive pair binding event.

In one aspect, a modified "stop-flow" methodology [B. J. Burke, F. E. Regnier, Analytical Chemistry 75, 1786-1791 (Apr. 15, 2003).] was adopted, enabled by a PDMS microfluidic chip which is configured with two sample reservoirs, both connected to equal length channels that converge into a single channel with a serpentine mixer made from a series of connected C shapes followed by a restriction (see FIG. 22). This simple microfluidic network, which allows for sample introduction and rapid mixing of the two interacting species, was fabricated using standard photolithography and replica molding techniques [D. C. Duffy, J. C. McDonald, O. J. A. Schueller, G. M. Whitesides, Analytical Chemistry 70, 4974-4984 (Dec. 1, 1998); G. M. Whitesides, E. Ostuni, S. Takayama, X. Y. Jiang, D. E. Ingber, Annual Review of Biomedical Engineering 3, 335-373 (2001).]. After the PDMS was cured and peeled from the mold, it was oxidized in $O_2$ plasma for 10 seconds and then placed on a 1-mm thick microscope glass slide creating an irreversible bond between the glass and PDMS. The glass slide was used to seal the microfluidic channels and allowed for the entire chip assembly to be handled and securely mounted onto a thermoelectrically temperature-controlled x-y translation stage. A shorter top piece of glass was also used as a faceplate, offering structural stability to minimize any possible microfluidic channel deformations during the sample introduction step. Nanoliter volumes of samples of each of the two binding pairs were aliquoted in the reservoirs at the top of the "Y", then a slight negative pressure was then applied to the chip exit well, drawing the two interacting species through the mixer and into the detection zone. In "stop-flow" experiments, the sample introduction pressure was selected to optimize the flow rate or linear velocity for the solutes. The need for rapid, complete mixing to produce a homogeneous solution of the binding pair was balanced with the requirement that the reaction has not proceeded appreciably before flow is stopped and analysis begins. These parameters can change slightly for each binding pair, with flow rates found to be in the range of 75-120 μL/min.

Figure 23:
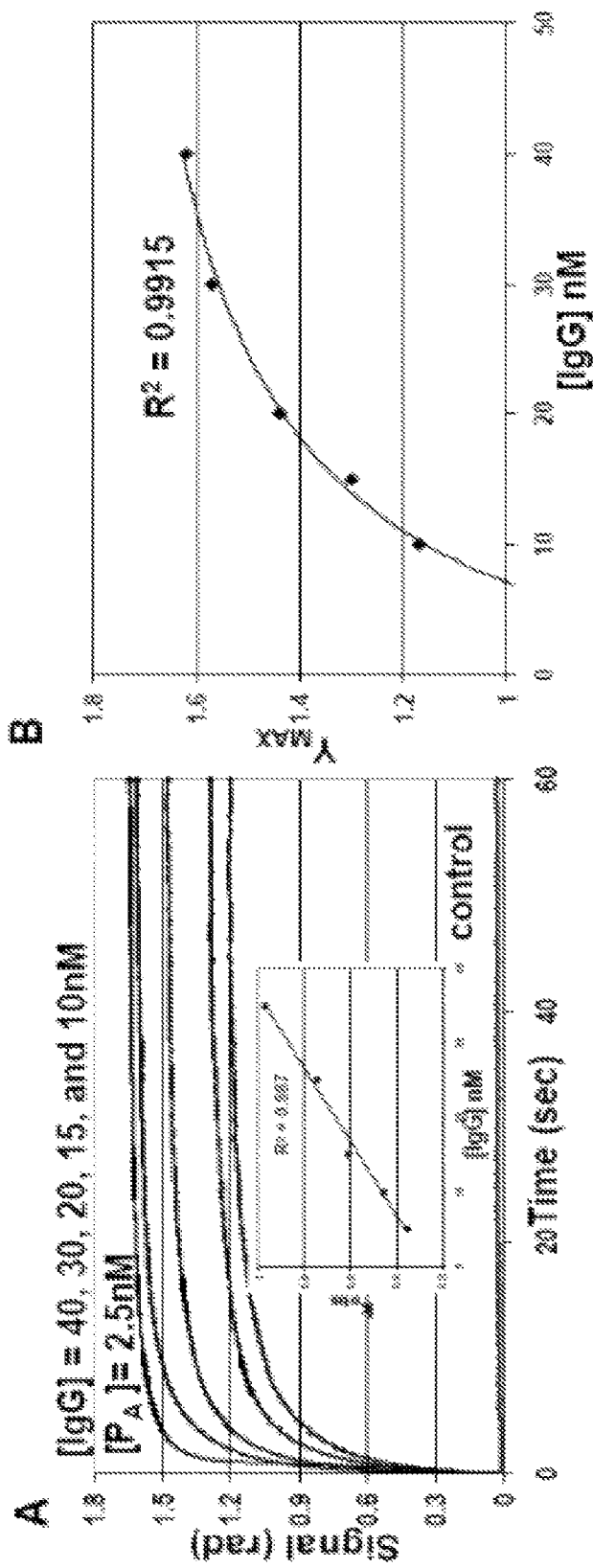
FIG. 23 shows A) Real-time association plots are shown for PA binding IgG at various nanomolar concentrations. Extracted rates are plotted versus [IgG] in the inset. B) Steady-state values are plotted as a function of IgG concentration and analyzed by Prism software.

Protein A (PA) binds the FC region of several IgG species, including human and rabbit, with high affinity (KD=5 nM–34.5 nM) [J. J. Langone, Advances in Immunology 32, 157-252 (1982); K. Saha, F. Bender, E. Gizeli, Analytical Chemistry 75, 835-842 (Feb. 15, 2003).] and provides an excellent model system to show molecular interactions can be studied using back-scattering interferometry. FIG. 23A shows the results from the stop-flow interaction experiment with this well-studied pair, in which the time-dependent intrinsic property changes (RI) were measured by BSI to determine affinity. In this case, a fixed concentration of Protein A of 2.5 nM was used and sequential experiments with increasingly larger concentrations of the FC region from IgG (i.e., from 10 to 40 nM) were performed. Conditions were such that PA was buffered at a pH=7.2 with 15 mM Na2HPO4, 50 mM NaCl, 0.1 mM EGTA, and 0.02% sodium azide. All IgG solutions were made using the same buffer as PA. The temperature of the solutions and micro-fluidic chip were held constant at 25° C. throughout the entire experiment. The association reaction was detected in real-time over a span of ~60 seconds. The shape of the binding curves changes with concentration of the antibody (IgG) at fixed concentration of the substrate, receptor or antibody, more rapidly reaching the equilibrium point.

The apparent binding affinity can be extracted from the data using a simple model that assumes first order kinetics or single mode binding, and plotting the observed rate ($k_{obs}$) versus the concentration of IgG. Least squares analysis of the line generated by this method using the kinetics obtained from backscattering interferometry yields a Kd for PA-IgG of 7.91 nM (±1.21). Alternatively a plot of the end-point values of phase as determined by BSI for the reaction between PA and IgG as a function of the concentration of IgG can be used as a second method to evaluate binding affinity of the complex. This plot (FIG. 23B) exhibits the hyperbolic shape often seen in enzyme kinetic studies and described by the law of mass action. Analysis of the steady-state data by Prism™ software yields a Kd value of 6.27 nM (±0.47), which correlates well with the results obtained from the kinetic analysis and with values reported in the literature [K. Saha, F. Bender, E. Gizeli, Analytical Chemistry 75, 835-842 (Feb. 15, 2003).]. The nominal leveling off observed at higher concentrations of the ligand in the end point assay can be attributed to a bulk RI signal which becomes increasing significant at higher concentrations of the ligand, IgG. This background signal contribution is typically small compared to that of the binding event.

As a control, the 2.5 nM solution of PA and a 40 nM solution of the FAB fragment of IgG were introduced into the microfluidic chip and the reaction progress was monitored. FIG. 23A demonstrates that combining a high concentration of the non-complementary strand with the target results in a nominal response by BSI. In fact the control shows <1.6% of the signal observed at equivalent PA and IgG FC concentrations, while exhibiting decidedly different kinetics. Even though a bulk property change is expected and observed, the magnitude of this contribution is small.

Interaction assays by BSI also yield the benefits inherently afforded by microfluidics. It was possible to perform the entire Protein A—IgG homogeneous, label-free binding assay in inexpensive, easy to manufacture PDMS chips with a mere $105 \times 10^{-9}$ g (2.5 pmoles) of Protein A and just $287 \times 10^{-9}$ g (5.75 picomoles) of the FC fragment of IgG. Under the best case scenario, a comparable determination by ITC would typically require 300 to a 1.000-fold more mass (ca. 300 µg) of each of the reactants.

Calmodulin (CaM), the ubiquitous, calcium-binding protein that can bind to and regulate a multitude of different protein targets, was chosen to further demonstrate the utility of BSI for homogeneous, label-free molecular interaction studies. CaM is found in the cytoplasm, within organelles, or associated with the plasma or organelle membranes and affects many different functions including inflammation, metabolism, apoptosis, muscle contraction, intracellular movement, short-term and long-term memory, nerve growth, and the immune response (REFS). Upon binding to $Ca^{2+}$, CaM undergoes a conformational change thought to induce activity. Once activated by $Ca^{2+}$, CaM binds, among other things, the protein calcineurin, a skeletal muscle myosin peptide, and small inhibitor molecules. Ligands ranging in molecular weight from just 40.04 g/mole for an ion to 77 kDa for a protein, and spanning three decades in Kd (from a few micromolar to tens of nanomolar) provide an array of ligand-substrate interactions to demonstrate the utility of BSI.

Figure 24:
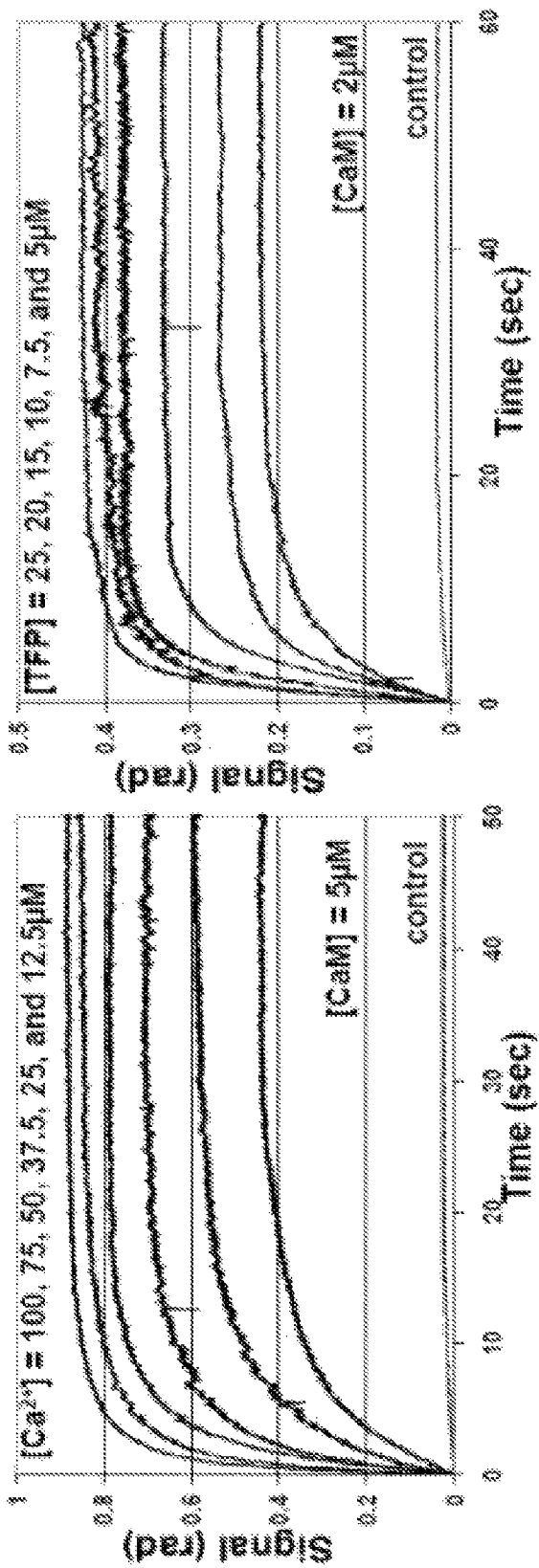
FIG. 24 shows association curves of CaM with A) $Ca^{2+}$, B) TFP, C) Calcineurin, and D) M13.
Figure 24:
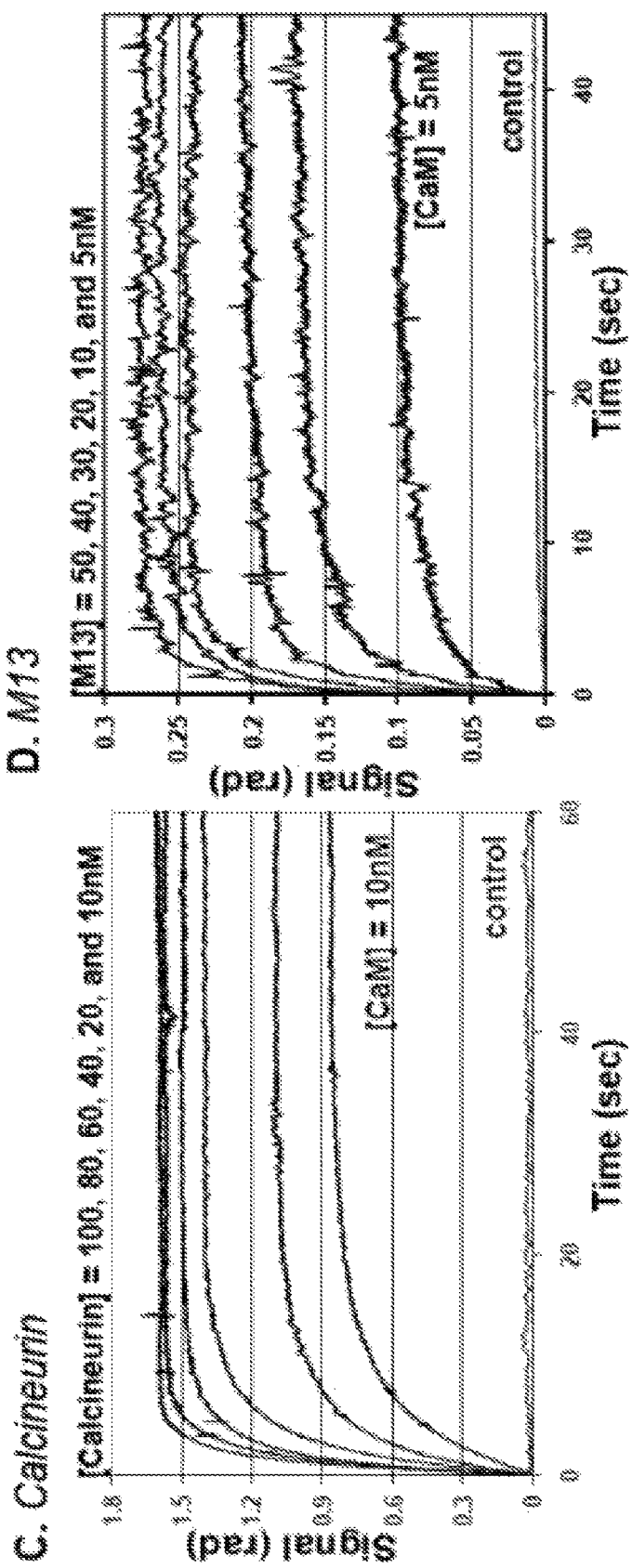

FIG. 24 shows that a single methodology, label-free homogeneous assays by BSI, can be used to quantify: a) CaM-$Ca^{2+}$ interactions, b) interactions between CaM and the small molecule inhibitor, trifluoperazinc dihydrochloride (TFP), c) CaM and Calcincurin binding, and d) reaction of CaM with M13, a peptide from the sequence of skeletal muscle myosin light chain kinase (skMLCK), a known target of the $Ca^{2+}$ activated CaM complex.

Calmodulin-calcium ion interaction has been studied previously with published Kd values ranging from 1-10 µM. Homogeneous, label-free CaM-$Ca^{2+}$ interactions are quantified with BSI by real-time monitoring the sequential reactions of a constant concentration of 5 µM CaM with $Ca^{2+}$ solutions increasing in concentrations from 12.5-100 µM (FIG. 24A). Here CaM was buffered at pH=7.5 with 0.1M HEPES and 0.1M KCl, with its concentration held constant at 5 µM. In this aspect, the CaM solution contained a small amount of EGTA to chelate any free $Ca^{2+}$. The reactions were carried out in the same microfluidic chip molded in PDMS with the temperature fixed at 25° C. A 5 µM CaM solution and a 100 µM $Ca^{2+}$ solution both consisting of excess EGTA (i.e., 400 µM), served as the control. As shown in FIG. 24A, when evaluated by stop-flow the control generated a nominal response in BSI, showing <3% change in signal above that observed in the absence of excess EGTA at equivalent CaM and $Ca^{2+}$ concentrations.

Kinetic analysis using a single exponential gives rise to a plot of observed rates versus $Ca^{2+}$ concentration that is linear. A least squares analysis of the linear plot yields the slope, intercept, and their respective errors. From this analysis, Kd was determined to be 3.36 µM (±5.75), which agrees well with the published range of 1-10 µM. Analysis of the plot of the steady-state values monitored by BSI versus the concentration of $Ca^{2+}$ using Prism™ software yields a Kd value of 17.77 µM (±1.55). Without wishing to be bound by theory, it is believed that the disparity in these two values was due likely to a less than optimal approach to fitting the kinetic data and the RI background present from unreacted ligand, particularly at high concentrations.

Investigations into the interaction between CaM and the small molecule inhibitor, trifluoperazine dihydrochloride (TFP) have been previously examined using affinity chromatography (42), a lengthy and substrate consuming technique 30 µg pr sample, each sample is 300 µL. In these chromatography studies, dissociation constants or affinities ranged from 4.5-5.8 µM. Here, BSI was used to quantify the CaM-TFP interaction readily, rapidly and with only micrograms of sample.

CaM was buffered at pH=7.5 with 0.1M HEPES and 0.1M KCl, its concentration was held constant at 2 µM and to ensure CaM was in its active conformational state, the solution contained 0.2 mM CaCl2. TFP solutions were made using the same buffer and held at the same pH as CaM. Throughout the experiment, the temperature was kept constant at 25° C., and the same PDMS microfluidic chip was used. The interaction of CaM with TFP was monitored by BSI in real-time within a probe volume on the order of picoliters (FIG. 24B). A 2 µM solution of CaM and a 25 µM solution of TFP, both in the absence of $Ca^{2+}$, were mixed to serve as a control. In this case the control showed <4% of the signal observed at equivalent CaM and TFP concentrations when $Ca^{2+}$ was present.

Kinetic analysis produces a linear relationship between the observed rates over the concentration range of TFP used, and from the least squares analysis, KD was determined to be 4.73 µM (±1.07) for the CaM-TFP complex. This value is in excellent agreement with value obtained by affinity chromatography. A plot of the BSI signal values at steady-state versus TFP concentration was constructed and fitted using Prism™ software giving a Kd of 7.640 µM (±0.85).

Calcineurin is a protein phosphatase and the major CaM binding protein in the brain. The pair has been studied previously using both affinity chromatography and radioligand binding, with dissociation constants being reported between 4 nM and 16 nM. The study of this pair illustrates the importance of BSI for chemical interaction studies; no labeling is required, inherently short analysis times are possible, and again microfluidics facilitate assays with small amounts of reactants. In this case CaM was buffered at pH=7.5 with 0.1M HEPES and 0.1M KCl and 0.2 mM CaCl2, with the CaM concentration held constant throughout the experiment at 10 nM. FIG. 24C shows that the time-dependent reaction of CaM with various concentrations of Calcineurin can be recorded with BSI. A 10 nM solution of CaM and a 100 nM solution of Calcineurin both in the absence of $Ca^{2+}$ were mixed to serve as a control. The control showed <1.5% of the signal observed at the equivalent CaM and Calcineurin concentrations in the presence of $Ca^{2+}$.

Kinetic analysis yields a linear relationship between the observed rates and Calcineurin concentration. The slope and intercept from a least squares analysis yields a Kd of 15.67 nM (±5.12). The determination falls within the results published earlier using affinity chromatography and radioligand binding [C. B. Klee, M. H. Krinks, Biochemistry 17, 120-126 (1978); M. G. of Sciences of the Speaker, S. J. Orlow, T. W. Sturgi II, O. M. Rosen, Proceedings of the National Academy United States of America-Biological Sciences 80, 329-333 (1983); M. J. Hubbard, C. B. Klee, Journal of Biological Chemistry 262, 15062-15070 (Nov. 5, 1987).]. Steady-state or end-point analysis yields a hyperbolic relationship that when analyzed produces a Kd value of 11.57 nM (±0.79).

M13, a peptide from the sequence of skeletal muscle myosin light chain kinase (sk-MLCK), is also a known target of the $Ca^{2+}$ activated CaM complex and has been shown by Surface Plasmon Resonance (SPR) to bind with high affinity (KD=1.9 nM 5.5 nM)(46). While SPR has been used in conjunction with microfluidics and can be employed for small volumes at low concentrations, it relies on immobilization chemistries for attachment of one reactant onto a metal (typically Au) surface. Surface immobilization chemistry can be costly, time consuming, incompatible with some materials, and often exhibit decreased activity over time [R. L. Rich, Y. S, N. Day, T. A. Morton, D. G. Myszka, Analytical Biochemistry 296, 197-207 (Sep. 15, 2001).]. Immobilization of the reactant to the surface can perturb the species possibly skewing kinetic and thermodynamic results. Furthermore the SPR signal falls off rapidly with the distance from the surface limiting the size of the target and negating the potential to gain information about bulk solution binding properties.

For free-solution BSI studies of the interaction between CaM and M13, CaM buffered at pH=7.5 with 0.1M HEPES, 0.1M KCl, and 0.2 mM CaCl2. The concentration of CaM was kept constant throughout the experiment at 5 nM. A buffer-matched range of concentrations of M13 were reacted with CaM sequentially and time-dependent association events were detected by interferometry (FIG. 24D). A 5 nM solution of CaM and a 50 nM solution of M13, both devoid of $Ca^{2+}$, were mixed to serve as a control. The control showed <2.6% of the signal observed at equivalent CaM and M13 concentrations when $Ca^{2+}$ was present. Similar to other CaM binding events studied, a linear relationship between the observed rates and the ligand concentration (M13) enabled the calculation of KD. For the CaM-M13 pair this value was determined to be 2.72 nM (±0.4 1) and compares well with results published using SPR [S. Montigiani, G. Neri, P. Neri, D. Neri, Journal of Molecular Biology 258, 6-13 (Apr. 26, 1996).]. Analysis using the end-point CaM-M13 signal values versus concentration and Prism™ software yields a KD value of 11.13 nM (±1.21). The increased noise observed in this determination and the larger RI changes at higher concentration of ligand are the likely causes for the disparity between the end-point and kinetic affinity values.

Kinetic parameters can also be derived from BSI. For example the interaction of Calmodulin with M13, the peptide sequence from the Calmodulin-binding domain of myosin light chain kinase (MLCK) show remarkable consistency with stopped-flow kinetics performed previously (48). The association rate determined by BSI was $3.1 \times 10^7$ $M^{-1}s^{-1}$ compared to $39 \times 10^7$ $M^{-1}s^{-1}$ as determined by Török [K. Török, Biochemical Society Transactions 30, 55-61 (April, 2002).].

Figure 25:
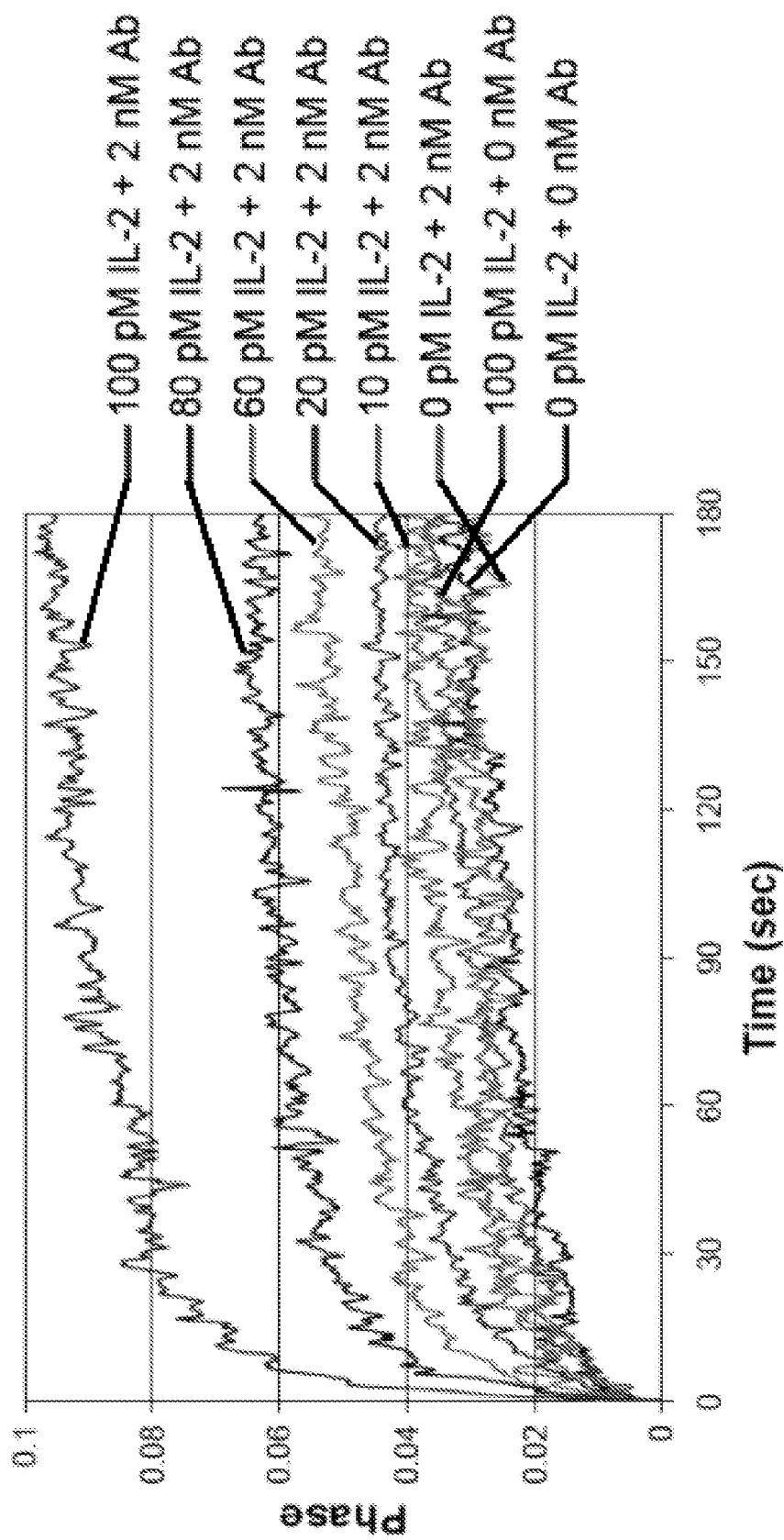
FIG. 25 shows IL-2—Ab binding curves with interaction assay performed in cell free media.

Homogeneous assays based on calorimetry are typically problematic for very low and very high binding affinities. To effectively evaluate the interaction between pairs with picomolar binding affinities, it is desirable to perform the determination at sub-nanomolar concentrations, which is often not possible with ITC. Due to the sensitivity resulting from a multi-pass interferometric optical train, such measurements are possible with BSI. To demonstrate this unique feature, the interaction between IL-2 and a monoclonal antibody was measured in buffer and in cell-free media (FIG. 25). Interleukin-2 (IL-2) is a well-studied protein [J. Theze, P. M. Alzari, J. Bertoglio, Immunology Today 17, 48 1-486 (October, 1996); A. K. Abbas, A. H. Lichtman, Cellular and Molecular Immunology (Saunders, Philadelphia, ed. Fifth, 2003).] that is secreted by activated T-cells and is involved in the regulation of the immune response. IL-2 is responsible for the proliferation of antigen-specific cells as well as promoting the proliferation and differentiation of other immune cells. IL-2 also aids in regulating the apoptotic pathway of antigen-activated T-cells. The interaction between IL-2 and its antibody (IL-Ab) have previously been shown to bind with high affinity, with reported Kd values ranging from 10 pM to 60 pM [G. H. Reem, N. H. Yeh, D. L. Urdal, P. L. Kilian, J. J. Farrar, Proceedings of the National Academy of Sciences of the United States of America 82, 8663-8666 (DEC, 1985).].

BSI was used to examine this system in cell media label-free in a homogeneous format allowing interactions of IL-Ab (2 nM) with IL-2 (10-100 pM) to be monitored in real-time. Both the IL-2 and IL-Ab solutions were made utilizing RPMI 1640 cell media with 1% fetal bovine serum (FBS) and 10 µg/mL Cipro. A blank (0 M of both IL-2 and IL-Ab) as well as two controls (0 M IL-2 reacted with $2 \cdot 10^{-9}$ M IL-Ab; $1 \cdot 10^{-11}$ M IL-2 mixed on chip with 0 M IL-Ab) were evaluated. A slight RI change was seen in all the blanks, but the change was consistent for all three, indicating that this was an effect of the mixing/media bulk RI changes. The kinetic analysis, as described above for the CaM and PA-IgG pairs, was performed on the data and yields a linear plot. From the analysis, a Kd of 51.8 pM (±10.5 pM) was determined and falls within the published range of 10 pM to 60 pM [G. H. Reem, N. H. Yeh, D. L. Urdal, P. L. Kilian, J. J. Farrar, Proceedings of the National Academy of Sciences of the United States of America 82, 8663-8666 (DEC, 1985).].

E. Molecular Interactions and Biosensor Applications

Molecular interaction analysis is an active area of biomedical research as scientists look for understanding of which molecules bind to other molecules. This information can be critical on any number of levels, especially as it pertains to an understanding of the mechanism of action of pharmaceutical small molecules or biological macromolecules. The study of interactions can also elucidate possible mechanisms of toxicity and can help identify how best to modify molecules to become more effective therapeutics. A thorough understanding of which molecules bind which molecules can also lead to a more comprehensive understanding of the molecular pathways involved in gene function which can help identify new points of intervention in disease states such as cancer or diabetes, or new points of intervention in the pathways that contribute to aging. Molecular interactions can also provide a rapid diagnostic tool for the presence or absence of molecules that are correlated with disease or with the presence of pathogens in the environment.

Historically, scientists have used semi-quantitative methods such as genetic, biochemical, and structure-function methods that have produced qualitative or semiquantitative interaction data. Beginning in 1990, Biacore introduced the first commercial machine to use surface plasmon resonance (SPR) to study the real time kinetics of biomolecular interactions. Systems biology approaches will require these types of data to better model the huge number of interactions forming specific molecular networks.

Biosensors have been defined as any type of device that contains a bioreceptor and a transducer. The bioreceptor can be a biological molecular species such as a nucleic acid, a protein, enzyme, antibody or even a living biological system such as cells or whole organisms that would bind the target species. The transducer would then convert this binding event into a measurement that could be recorded or displayed. Several types of transducers have been developed, including optical measurements (including fluorescence, luminescence, absorption, phosphorescence, Raman, SERS, surface Plasmon resonance, and back-scattering interferometry), electrochemical, and mass-sensitive (including surface acoustic wave and microbalance).

1. Antibody Biosensors

In conventional antibody biosensors, the antibody bioreceptors bind the target of interest and then are visualized by binding a secondary antibody labeled with radioisotopes or conjugated to an enzyme such as horseradish peroxidase that catalyzes a chemiluminescence reaction that can be visualized with photographic film or appropriate photometric sensor. In one aspect, the invention relates to an antibody biosensor because BSI in the absence of a secondary antibody can detect the primary antibody binding the target due to a change in the refractive index due to the binding event, for example due to a change in polarizability of the target.

Accordingly, in a further aspect, the invention relates to a method for method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns, wherein the method is employed to detect a target of interest in the absence of a second antibody.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$M, wherein the method is employed to detect a target of interest in the absence of a second antibody.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL, wherein the method is employed to detect a target of interest in the absence of a second antibody.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein the method is employed to detect a target of interest in the absence of a second antibody.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, wherein the system is employed as an antibody biosensor.

2. Nucleic Acid Biosensors

In conventional nucleic acid biosensors, the specific sequence of bases that define a segment of DNA can be used as a probe to bind other DNA sequences, and these DNA sequences can be labeled with radioactive or other labels. In one aspect, the invention relates to a DNA biosensor because BSI in the absence of a labeled secondary DNA probe can detect the primary DNA binding the target DNA due to a change in the refractive index due to the binding event.

Accordingly, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns, wherein the method is employed to detect a DNA sequence of interest in the absence of a labeled secondary DNA probe.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$ M, wherein the method is employed to detect a DNA sequence of interest in the absence of a labeled secondary DNA probe.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL, wherein the method is employed to detect a DNA sequence of interest in the absence of a labeled secondary DNA probe.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein the method is employed to detect a DNA sequence of interest in the absence of a labeled secondary DNA probe.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, employed as nucleic acid biosensor.

3. Enzyme Biosensors

In conventional enzyme biosensors, the presence or absence of substrate molecules can be determined by measuring the production of the enzymatic reaction end products. In one aspect, the invention relates to an enzyme biosensor because BSI can be used to measure the amount of the initial substrate or the enzymatic reaction end products as long as they are binding a molecular species where the binding can be detected by a change in the refractive index of the solution. One example can be when glucose is determined to be present by its binding to a glucose binding protein (GBP), an $E.$ $coli$ periplasmic binding protein, wherein the conformation of the GBP changes upon binding the glucose molecule. In contrast, conventional glucose biosensors, such as the one sold by SenseOmics Inc., utilize a recombinant GBP that has been specifically modified to include a cysteine residue to which a fluorescent probe is then attached, and upon binding glucose the conformational change leads to a decrease in fluorescence intensity.

Accordingly, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns, wherein the method is employed to measure the production of the enzymatic reaction end products in the absence of specifically modified recombinant GBP including a fluorescent probe.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$M, wherein the method is employed to measure the production of the enzymatic reaction end products in the absence of specifically modified recombinant GBP including a fluorescent probe.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL, wherein the method is employed to measure the production of the enzymatic reaction end products in the absence of specifically modified recombinant GBP including a fluorescent probe.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein the method is employed to measure the production of the enzymatic reaction end products in the absence of specifically modified recombinant GBP including a fluorescent probe.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, wherein the system is employed as an enzyme biosensor.

4. Cellular Biosensors

In conventional cellular biosensors, the presence or absence of substrate molecules can be measured by measuring cellular metabolism, cell respiration, or bacterial bioluminescence. In one aspect, the invention relates to a cellular biosensor because BST can be used to measure the amount of the initial substrate as long as it is binding a molecular species where the binding can be detected by a change in the refractive index of the solution. One example can be when heavy metals such as mercury are determined to be present by their binding to the MerR (metalloregulatory) proteins, wherein the conformation of the MerR proteins changes upon binding the mercury metal ion. In contrast, conventional heavy metal biosensors utilize a recombinant bacterial strain that has been genetically modified to include a lux reporter gene, and then toxicity as a result of the presence of heavy metals can be indirectly assessed by the diminution of the light signal.

Accordingly, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns, wherein the method is employed to directly assay an analyte of interest in the absence of genetically engineered bacteria.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$ M, wherein the method is employed to directly assay an analyte of interest in the absence of genetically engineered bacteria.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL, wherein the method is employed to directly assay an analyte of interest in the absence of genetically engineered bacteria.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein the method is employed to directly assay an analyte of interest in the absence of genetically engineered bacteria.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, wherein the system is employed as a cellular biosensor.

5. Measurement of End-Point Values

In one aspect, BSI can measure end-point values of phase for the reaction between molecule A and molecule B as a function of the concentration of molecule B to determine the binding affinity of the complex and/or to quantitatively determine the concentration of the A-B product at reaction equilibrium. End-point concentration bioassays can be used in both research and clinical diagnostic applications.

In one aspect, the disclosed methods and systems can be used to perform semi-quantitative end-point measurements. A calibration curve for a first analyte (e.g., antibody) at a known concentration can be generated by measuring the response to interaction between the first analyte and a second analyte (e.g., antigen) at systematically varied known concentrations. Comparison of a subsequent response measured when an unknown concentration of the second analyte is allowed to interact (e.g., antibody-antigen binding) with a known concentration of the first analyte to the calibration curve yields the concentration of the second analyte in the sample analyzed. Amount of the second analyte in the sample can then be determined as a function of sample volume.

Thus, in one aspect, the end point of the interaction between a first non-immobilized analyte and a second non-immobilized analyte can be determined by a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns.

In one aspect, the end point of the interaction between a first non-immobilized analyte and a second non-immobilized analyte can be determined by a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$ M.

In one aspect, the end point of the interaction between a first non-immobilized analyte and a second non-immobilized analyte can be determined by a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein at least one of the analytes is present during the determination in a solution with a volume in the detection zone of less than about 500 nL.

In one aspect, the end point of the interaction between a first non-immobilized analyte and a second non-immobilized analyte can be determined using an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel.

In a further aspect, the first and second analytes can be combined prior to introduction. That is, the analytes can be combined (and thus can potentially interact) prior to performing the disclosed methods. In this aspect, the step of introducing the first analyte and the step of introducing the second analyte are performed simultaneously.

Alternatively, in a further aspect, the first and second analytes are combined after introduction. That is, the analytes can be combined at a point before the channel, or at a point within the channel, when performing the disclosed methods. In this aspect, the step of introducing the first analyte and the step of introducing the second analyte are performed either simultaneously or sequentially. In a further aspect, the detecting step is performed during the interaction of the first analyte with the second analyte.

6. Determination of Kinetic Parameters

In a further aspect, BSI can determine kinetic parameters. That is, the back-scattering interferometry (BSI) technique described herein can be used to monitor various kinetic parameters, such as, for example, binding affinities, of a chemical and/or biochemical analyte species. The use of BSI for the determination of a kinetic parameter can provide one or more advantages over traditional techniques, for example, free-solution measurements of label-free species, high throughput, small sample volume, high sensitivity, and broad dynamic range. A BSI technique can be performed on a free-solution species, a surface immobilized species, or a combination thereof. In one aspect, the species of interest is a free-solution species, wherein at least a portion of the species of interest is not bound or otherwise immobilized. In another aspect, at least a portion of the species of interest is surface immobilized.

In one aspect, a BSI technique can be used to analyze and/or quantify one or more molecular interactions, such as, for example, a dissociation constant for one or more binding pair species. Such a binding pair species can be, in various aspects, a protein-protein, peptide-protein, small molecule-protein, ion-protein, or an antibody-antigen pair. Other reactions and/or molecular interactions can be likewise analyzed via BSI and the present invention is not intended to be limited to the specific binding pairs and/or reactions recited herein.

The sensitivity of a BSI technique can allow analysis and/or determination of at least one kinetic parameter to be performed on a small volume sample. The volume of a sample comprising at least one species of interest can, in various aspects, be less than about 1 nL, for example, about 900, 850, 800, 700, 600, 500, 400, 350, 300, 250, or 200 pL; less than about 600 pL, for example, about 580, 550, 500, 450, 400, 350, 300, 250, or 200 pL; or less than about 400 pL, for example, about 390, 380, 370, 360, 350, 340, 330, 320, 310, 300, 280, 250, 230, or 200 pL. In one aspect, the sample volume is about 500 pL. In another aspect, the sample volume is about 350 pL. The sample volume can also be greater than or less than the volumes described above, depending on the concentration of a species of interest and the design of a particular BSI apparatus. A species that can be analyzed via BSI can be present in neat form, in diluted form, such as, for example, in a dilute solution, or any other form suitable for analysis by a BSI technique. The concentration of a species of interest can likewise vary depending upon, for example, the design of a particular BSI apparatus, the volume of sample in the optical path, the intensity of a response of a specific species to the radiation used in the experiment. In various aspects, the species can be present at a concentration of from about 1 pM to greater than 100 mM.

Analysis of a kinetic parameter via a BSI technique can be performed on a static sample, a flowing sample, for example, 75-120 µL/min, or a combination thereof. In one aspect, an analysis can be a stop-flow determination that can allow an estimation of the dissociation constant ($K_D$) of one or more binding pairs of species. The speed at which one or more samples can be analyzed can be dependent upon, inter alia, the data acquisition and/or processing speed of the detector element and/or processing electronics. Methods for adjusting the throughput speed of a BSI apparatus, such as signal multiplexing, can be utilized and are considered to be included in various aspects of the present invention.

An apparatus for analyzing a kinetic parameter using a BSI technique can comprise an optical system and a sample comprising the one or more species of interest. The optical system can comprise, a laser, such as, for example, a He—Ne laser, and a detector, such as, for example, a CCD array detector, such as a high resolution linear CCD. In one aspect, the detector is a CCD bar code scanner. The sample can be positioned in or on a channel, such as, for example, a microfluidic channel on a poly(dimethylsiloxane) chip. A microfluidic channel, if present, can comprise a pattern, such as, for example, a serpentine flow pattern, and/or a mixing zone, such as, for example, a squeeze. In a specific aspect, the sample can be positioned in a rectangular channel approximately 50 μm by 70 μm. In such a specific aspect, the sample can be irradiated with a 100 μm diameter He—Ne laser beam to yield an optical sample volume of approximately 350 pL. In other various aspects, a microfluidic channel, if present, can be semicircular or cylindrical, such as, for example, a fused silica capillary, and the present invention is not intended to be limited to any particular microfluidic channel geometry.

A microfluidic channel, if present, can comprise one or multiple channels that can hold and/or transport the same or varying samples, and a mixing zone. The design of a mixing zone can allow at least initial mixing of, for example, one or more binding pair species. The at least initially mixed sample can then be subjected to a stop-flow analysis, provided that the reaction and/or interaction between the binding pair species continues or is not complete at the time of analysis. The specific design of a microfluidic channel, mixing zone, and the conditions of mixing can vary, depending on such factors as, for example, the concentration, response, and volume of a sample and/or species.

The concentration of one or more analyte species in a sample can be determined with a BSI technique by, for example, monitoring the refractive index of a sample solution comprising an analyte species. A property, such as, for example, refractive index, can be measured in real-time and the kinetics of an interaction between analyte species determined therefrom. Other experimental conditions, such as, for example, temperature and pH, can optionally be controlled during analysis. The number of real-time data points acquired for determination of a kinetic parameter can vary based on, for example, the acquisition rate and the desired precision of a resulting kinetic parameter. The length of time of a specific experiment should be sufficient to allow acquisition of at least the minimal number of data points to calculate and/or determine a kinetic parameter. In one aspect, an experiment can be performed in about 60 seconds.

An apparent binding affinity between binding pair species can subsequently be extracted from the acquired data using conventional kinetics models and/or calculations. In one aspect, a model assumes first order kinetics (a single mode binding) and the observed rate ($k_{obs}$) can be plotted versus the concentration of one of the species. A desired kinetic parameter, such as, for example, $K_D$, can be determined by, for example, a least squares analysis of the relationship plotted above. A suitable fitting model can be selected based on the particular experimental condition such that a rate approximation can be determined at the end of the analysis. One of skill in the art can readily select an appropriate model or calculation to determine a particular kinetic parameter from data obtained via BSI analysis.

7. Immobilized Bait Measurements

In a further aspect, BSI can measure immobilized bait measurements. One example of a measurement of an immobilized bait using BSI is where biotin was determined to bind surface-immobilized streptavidin (2004 JACS Markov et al. 126:16659-64). The bait can be one of two interacting species, and, in conventional immobilized bait measurements, the bait is immobilized at a surface of the analysis system, wherein the interaction and analysis occur.

In contrast, the disclosed methods and systems can involve free-solution measurements. The disclosed methods and systems, however, can be used to interrogate analytes that are non-immobilized, yet bound. That is, the analyte can be selectively bound to another species that, too, is not immobilized at a surface of the analysis system. More specifically, the bait can be bound upon a substrate that is introduced as a free solution with respect to the detection zone. For example, the bait could be immobilized in a micelle, upon a nanoparticle, or within a cell membrane fragment. As further examples, the disclosed systems and methods can be applied to molecules embedded in micelles, cell membrane segments, intact cells, and/or nanoparticles with derivatized surfaces.

Analogously, one binding partner can be bound upon a nano- or microsupport that can then be analyzed within the disclosed systems under free solution conditions by using the disclosed methods.

As a further example, an analyte can be bound to a magnetic particle and delivered (or held) by magnetic fields at a desired detection zone within a larger system (e.g., a biological system such as an organism).

In a further example, one or more of the interacting analytes can be bound by "tether" to a surface of the system within the detection zone. Another, free-solution analyte can the be allowed to interact with the bound analyte, thereby forming one or more interaction products, which can remain bound via the tether or can be released into free solution. The tether can be, for example, attachment via covalent bond or other strong interaction. The attachment directly to the surface, attachment via a relatively short tether (e.g., functionalized alkyl chain, oligomer, or self-assembled monolayer) or via a long tether (e.g., functionalized alkyl chain or polymer—potentially hundreds or thousands of nanometers in length).

In conventional techniques, a first analyte is attached to a surface (e.g., via tether attachment). The attachment is typically followed by a wash step to remove remaining unattached first analyte from the sample or detection zone; this wash can be necessary to eliminate or minimize any interaction due to non-immobilized first analyte. The wash step is followed by the addition of a second analyte, which interacts with the immobilized first analyte to form one or more immobilized interaction products. In conventional techniques, this step is followed by a second wash step to remove remaining non-interacted second analyte from the sample or detection zone; this wash can be necessary to eliminate or minimize any interaction due to non-interacted second analyte. In contrast, in the disclosed methods and systems—at least in part due to the sensitivity of BSI when observing interaction products from interacting analytes—the second wash step can be unnecessary, as the signal observed in response to the formation and presence of the one or more interaction products is strong relative to any response due unreacted analytes. Thus, the disclosed methods can be performed for the analysis of interaction between an immobilized or tethered analyte and a non-immobilized analyte while omitting the second wash step.

Accordingly, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns, wherein the method is employed to investigate non-immobilized, yet bound analytes.

Accordingly, in a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$M, wherein the method is employed to investigate non-immobilized, yet bound analytes.

Accordingly, in a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL, wherein the method is employed to investigate non-immobilized, yet bound analytes.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein the method is employed to investigate non-immobilized, yet bound analytes.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, wherein the method is employed to investigate non-immobilized, yet bound analytes.

8. Free Solution Measurements

In a further aspect, BSI can measure free solution measurements. One example of a free solution measurement in life science applications can be when the BSI instrument is used to interrogate the binding of two biological macromolecules, such as IL-2 and a monoclonal antibody for IL-2, in solution by examining a change in the interference pattern produced from the reflection and refraction of the solution upon mixing the two biological macromolecules. In contrast, conventional methods require measuring the amount of IL-2 bound with monoclonal antibody for 11-2 by for example Western blotting that requires tethering the IL-2 to a solid support, binding the antibody, and then binding a secondary antibody that has a label attached to it for visualization. In contrast, the BSI method does not require that the protein being examined be bound to a solid support, as the measurement could be made in free solution.

Other surface-bound biosensor techniques can be supplanted by the disclosed free-solution methods and systems. For example, the objective of surface plasmon resonance (SPR), optical wave-guide techniques, grating coupled optical waveguide techniques, micro-cantilever techniques, atomic force microscopy, acoustic techniques, as well as labeled techniques (including chemiluminescence, ELISA, fluorescence detection, and solid or liquid scintillation) can be achieved with the disclosed systems and methods.

Accordingly, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$ M.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, wherein the method is employed to measure one or more characteristic properties and/or chemical events in free solution (i.e., non-immobilized analytes).

9. Label-Free Molecular Interactions

In a further aspect, BSI can measure label-free molecular interactions. One example of a label-free measurement in life science applications can be when the BSI instrument is used to interrogate the binding of two biological macromolecules, such as a DNA binding protein and the fragment of DNA that contains the sequence that the protein binds by examining a change in the interference pattern produced from the reflection and refraction of the solution upon mixing the two biological macromolecules. In contrast, conventional methods require DNA oligonucleotides to be immobilized prior to measuring the binding of a single-stranded DNA binding protein which was visualized using surface plasmon resonance (1999 JACS Brockman et al., 121:8044-51). In contrast, the BSI method does not require that the protein being examined be labeled or be bound to a solid support, as the measurement could be made in free solution In a further aspect, BSI can measure classes of biomolecular interaction studies as described herein. As used herein, proteins includes glycoproteins, lectins, peptides, antibodies, protein antibody mimetic and any antibody subclasses including SCFV, Fab, Fc, or molecular imprints (MIP). In a further aspect of the invention, the biomolecular interaction is an interaction of a protein with a protein. In a further of the invention, the biomolecular interaction is an interaction of an antibody with an antigen. In a further aspect of the invention, the biomolecular interaction is an interaction of an enzyme and a substrate. In a further aspect of the invention, the biomolecular interaction is an interaction of a protein and a virus. As used herein, virus includes phage. In a further aspect of the invention, the biomolecular interaction is an interaction of a receptor and a ligand. In a further aspect of the invention, the biomolecular interaction is an interaction of a protein and a carbohydrate. In a further aspect of the invention, the biomolecular interaction is an interaction of a protein and a nucleic acid. As used herein, nucleic acid includes DNA, RNA, and aptamers. In a further aspect of the invention, the biomolecular interaction is an interaction of a receptor and a ligand. In a further aspect of the invention, the biomolecular interaction is an interaction of a nucleic acid with a nucleic acid. In a further aspect of the invention, the biomolecular interaction is an interaction of a small molecule with a protein. In a further aspect of the invention, the biomolecular interaction is an interaction of a small molecule with a nucleic acid. In a further aspect of the invention, the biomolecular interaction is an interaction of a small molecule with a receptor. In a further aspect of the invention, the biomolecular interaction is an interaction of a small molecule and a carbohydrate. In a further aspect of the invention, the biomolecular interaction is an interaction of a small molecule and a virus. In a further aspect of the invention, the biomolecular interaction is an interaction of a small molecule with a small molecule. In a further aspect of the invention, the biomolecular interaction is an interaction of a cell with a protein. In a further aspect of the invention, the biomolecular interaction is an interaction of a cell with a carbohydrate. In a further aspect of the invention, the biomolecular interaction is an interaction of a cell with a cell. In a further aspect of the invention, the biomolecular interaction is an interaction of a cell with a small molecule. In a further aspect of the invention, the biomolecular interaction is an interaction of a cell with a nucleic acid. In a further aspect of the invention, the biomolecular interaction is an interaction of a cell with a virus.

Accordingly, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns, wherein the method is employed to measure one or more characteristic properties and/or chemical events of unlabelled (i.e., substantially label-free) analytes.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0 \times 10^{-5}$ M, wherein the method is employed to measure one or more characteristic properties and/or chemical events of unlabelled (i.e., substantially label-free) analytes.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL, wherein the method is employed to measure one or more characteristic properties and/or chemical events of unlabelled (i.e., substantially label-free) analytes.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein the method is employed to measure one or more characteristic properties and/or chemical events of unlabelled (i.e., substantially label-free) analytes.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, wherein the system is employed to measure one or more characteristic properties and/or chemical events of unlabelled (i.e., substantially label-free) analytes.

For the detection of biomolecular interactions, the following types of detectors can be replaced or can be able to be used in combination with BSI, including optical techniques including Surface enhanced Raman spectroscopy, and Surface Plasmon Resonance (SPR), SPR is an optical phenomenon used for measuring molecular interactions but requires that one molecular species be immobilized. The SPR signal arises in thin metal films and the signal depends on the refractive index of solutions in contact with the metal surface. A challenging aspect of using SPR is direct immobilization of one of the molecular species without disrupting its binding activity. In contrast to SPR, BSI can be used to measure the binding of macromolecules without either macromolecule being fixed to a surface. For example, using SPR, it was recently shown that soluble monomeric beta-amyloid peptides can bind anti-beta-amyloid monoclonal antibodies (J Phys Chem B 2007; 111: 1238-43). In contrast, BSI can also be used to measure soluble monomeric beta-amyloid peptides binding an anti-beta-amyloid monoclonal antibodies in free solution.

A further type of detector that can be replaced or used in combination with BSI is one that utilizes grating based approaches such as optical waveguide lightmode spectroscopy (OWLS). OWLS measures the surface immobilization of biomolecules in an aqueous solution. The technique is based on the incoupling of a laser into a waveguide by an optical grating. The incoupling only occurs at two defined angles that are sensitive to a change in the refractive index above the surface in the evanescent field. The OWLS method uses the change in the refractive index to measure the adsorbed mass. A challenging aspect of using OWLS is direct immobilization of one of the molecular species. In contrast to OWLS, BSI can be used to measure the binding of macromolecules without either macromolecule being fixed to a surface. For example, using OWLS, the interaction between mycotoxins and anti-mycotoxin monoclonal antibodies was measured (Biosens Bioelectron 2007 22:797-802). In contrast, BSI can also be used to measure the binding of soluble mycotoxins binding anti-mycotoxin monoclonal antibodies in free solution.

A further type of detector that can be replaced or used in combination with BSI is one that utilizes mass-sensitive measurements such as surface acoustic wave (SAW). In SAW, small mass changes can be measured that result from molecules binding the receptor molecules coupled to the active sensor surface. Small mass changes at the sensor surface affects the propagation velocity of acoustic shear waves traveling through a guiding layer at the sensor surface. A challenging aspect of using SAW is direct immobilization of one of the molecular species. In contrast to SAW, BSI can be used to measure the binding of macromolecules without either macromolecule being fixed to a surface. For example, using SAW, the interaction between bovine immunoglobulin G and Protein A was recently measured (International Conference on Solid State Sensors and Actuators Jun. 16-19 1997 1:187-190). In contrast, BSI can also be used to measure the binding of bovine immunoglobulin G and Protein A in free solution.

A further type of detector that can be replaced or used in combination with BSI is one that utilizes mass-sensitive measurements utilizing a piezoelectric crystal. For example, small mass changes can be measured that result from molecules binding the receptor molecules coupled to the active sensor surface due to a change in the oscillation frequency of a piezoelectric crystal. Piezoelectric crystals oscillate as a function of both the electrical frequency applied to the crystal and the crystal's mass. Small mass changes can therefore be measured electrically. In contrast to a microbalance, BST can be used to measure the binding of macromolecules without either macromolecule being fixed to a surface. For example, using a piezoelectric crystal, the interaction between Staphylococcal Enterotoxin B (SEB) and anti-SEB polyclonal antibodies was measured (Biosens Bioelectron 1997 12:661-7). In contrast, BSI can also be used to measure the binding of Staphylococcal Enterotoxin B and anti-SEB polyclonal antibodies in free solution.

10. Electrochemical Measurements

A further type of detector that can be replaced or used in combination with BSI is one that utilizes electrochemical measurements. For example, one electrochemical biosensor can detect L-phenylalanine via activity of three immobilized enzymes. The three enzymes are immobilized on an electrode wherein first L-phenylalanine dehydrogenase binds and reacts with L-phenylalanine producing NADH. Then salicylate hydroxylase uses oxygen and NADH to convert salicylate to catechol. Then tyrosinase oxidizes catechol to o-quinone which is reduced back to catechol with an electrode potential of −50 mV (Anal Commun 1999 36:281). In contrast to the electrochemical biosensor, BSI can be used to directly measure the presence of L-phenylalanine by its binding to another macromolecule in free solution.

Accordingly, in a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; introducing a second sample comprising a second non-immobilized analyte to be analyzed into the channel; allowing the first analyte to interact with the second analyte to form one or more interaction products; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; detecting positional shifts in the light bands; and determining the formation of the one or more interaction products of the first analyte with the second analyte from the positional shifts of the light bands in the interference patterns, wherein the method is employed to directly assay an analyte of interest in the absence of one or more specially modified enzymes, or an enzyme cascade.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination at a concentration of less than about $5.0\times10^{-5}$ M, wherein the method is employed to directly assay an analyte of interest in the absence of one or more specially modified enzymes, or an enzyme cascade.

In a further aspect, the invention relates to a method for real-time, free-solution determination of molecular interactions comprising the step of detecting the formation of one or more interaction products of two unlabeled, non-immobilized analytes, wherein at least one of the analytes is present during the determination in a solution with a volume in the detection zone of less than about 500 nL, wherein the method is employed to directly assay an analyte of interest in the absence of one or more specially modified enzymes, or an enzyme cascade.

In a further aspect, the invention relates to a method for free-solution determination of molecular interactions comprising the steps of providing a substrate having a channel formed therein for reception of a fluid sample to be analyzed; introducing a first sample comprising a first non-immobilized analyte to be analyzed into the channel; establishing a baseline interferometric response by directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the first sample; introducing a second sample comprising a mixture of the first non-immobilized analyte and a second non-immobilized analyte to be analyzed, wherein the first analyte to interacts with the second analyte to form one or more interaction products, into the channel; directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the second sample; detecting positional shifts in the light bands relative to the baseline; and determining the formation of the one or more interaction products of the first analyte with the second analyte from the positional shifts of the light bands in the interference patterns, wherein the method is employed to directly assay an analyte of interest in the absence of one or more specially modified enzymes, or an enzyme cascade.

Moreover, in a further aspect, the invention relates to an interferometric detection system comprising a substrate; a channel formed in the substrate for reception of a fluid sample to be analyzed; means for introducing a first sample comprising a first analyte; means for introducing a second sample comprising a second analyte; optionally, means for mixing the first sample and the second sample; a coherent light source for generating a coherent light beam, the light source being positioned to direct the light beam onto the substrate such that the light beam is incident on the channel to thereby generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample; a photodetector for receiving the backscattered light and generating one or more intensity signals that vary as a function of positional shifts of the light bands; and a signal analyzer for receiving the intensity signals, and determining therefrom, a characteristic property of the fluid sample in the channel, wherein the system is employed as an electrochemical measurement device.

11. Atomic Force Microscopy

A further type of detector that can be replaced or used in combination with BSI is one that utilizes atomic force microscopy (AFM). AFM utilizes the deflection of a microscalc cantilever by forces such as electrostatic or Van Der Waal etc. in order to scan a specimen at the nanometer scale. The technique can be used to image, measure or manipulate matter. For example, AFM has been used to measure the dissociation rate constants of aptamer protein complexes (Chem Asian J 2007 2:284-9). In contrast to AFM, BSI can be used to measure equilibrium dissociation rate constants of aptamer protein complexes in free solution.

12. End User Applications

BSI can be used in any market where measuring macromolecular interactions is desired. In basic life science research, better understanding of how proteins interact with one another in the complex networks that form biochemical and genetic regulatory pathways can lead to a better understanding of new potential intervention points.

For example, improperly functioning networks, due to inherited or somatic genetic mutations, can be probed with the disclosed systems and methods.

Drug discovery and development, as well as translational research, can also greatly benefit from the disclosed invention, because it offers alternatives for analysis wherein therapeutics bind a target molecule, thereby enabling further development of drug candidates. Modifications to drug candidates can also be assessed using BSI as a tool to determine binding properties to the target of interest. Strong and specific binding can be important for effective therapeutics. Moreover, understandings of which biomarkers are useful for predicting drug efficacy can benefit from tests for their presence in patients, as well as tests that help elucidate their basic biochemical and physiologic properties. It is contemplated that the disclosed invention can facilitate drug discovery, drug development, and translational research.

In the food industry, as well as in biodefense applications, a rapid methodology that can assay for the presence of toxins, xenobiotics, allergens, additives, or biowarfare agents whether chemicals, viruses, or cellular pathogens such as certain bacteria can be useful as evidenced today by a large number of such items for which no easy to use tests are readily available today. It is contemplated that the disclosed invention can find utility in food industry and biodefense applications.

The disclosed invention can also be used in clinical diagnostics for early diagnosis of disease, monitoring disease progression, measurement of drug response to disease, and other applications of personalized medicine diagnostics, such as determining optimum drug dosage or drug for each individual based on diagnostic testing.

F. Experimental

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Device Fabrication

A fluidic network was designed using commercially available software (CleWin 2.7). A soda lime/chrome lithographic mask (chrome thickness approximately 100 nm) was then prepared (Delta Mask, The Netherlands) using this fluidic network design. Master molds were subsequently created from the lithographic mask using conventional optical and soft lithographic techniques.

Three inch silicon wafers (P <100>) were cleaned by sonication in acetone followed by treatment with piranha solution. The sonicated and treated wafers were then rinsed with deionized water and placed on a hot plate at 95° C. for 5 minutes just prior to deposition of a photoresist. A negative photoresist (SU-8 2050, available from Microchem, Newton, Mass., USA) was then evenly deposited on the surface of the Si wafer using a bench-top single wafer spinner (Laurell WS-400). A few milliliters of the negative photoresist were poured onto the center of the wafer and spinning commenced for 10 seconds at 500 rpm to spread the photoresist. The speed of the wafer was then increased to 3000 rpm for 40 seconds to form a homogeneous coating. The wafer was then removed from the spin coater and placed on a hot plate for a soft bake (3 min at 65° C.⇒9 min at 95° C.). The wafer was subsequently allowed to cool to room temperature. UV exposure through the photolithographic mask for ~15 seconds was accomplished using a Laurell WS-400 Bench-top single wafer spinner contact mask aligner. Following irradiation, a post exposure bake (PEB) was performed (1 min at 65° C.⇒7 min at 95° C.). The wafer was again cooled to room temperature.

Unexposed areas of photoresist were then removed using an organic developer (SU-8, available from Microchem). Isopropyl alcohol (IPA) was used to ensure the wafer was completely developed. IPA will form a milky white substance on the wafer if any unexposed photoresist remains. The master mold was then rinsed and hard baked (~5 hours at 2200° C.) to ensure device stability. An Alphastcp 200 stylus surface profiler (Tencor Instruments) was used to accurately measure the height of the standing relief structures.

All binding assays were performed in microchips created by cast molding onto the master mold fabricated above. Cast molding was performed using a silicon elastomer, polydimethylsiloxane (PDMS), purchased as Sylgard 184 (Dow Corning, Midland, Mich.). Prior to casting, the PDMS was mixed in a 10:1 ratio (base:curing agent) and degassed.

PDMS was cast over the master that had been placed into a 100×15 mm Falcon Petri dish (Becton Dickinson, Franklin Lakes, N.J.) such that the height of the PDMS was ~2 mm. The Petri dish was placed into a desiccator, and a vacuum was applied for further degassing. Once no air bubbles were visibly present, the Petri dish was removed from the desiccators and set in a large convection oven for roughly 8 hours at 65° C.

After the curing process was complete, the Petri dish was removed from the oven and allowed to cool briefly. The PDMS microchip device was physically removed from the Si master mold by fine precision scalpel and tweezers. Access ports for sample introduction (2 ports) and applied vacuum/waste removal (1 port) were mechanically punched out by stainless steel capillary tubing. PDMS, with the fluidic network facing up, was then plasma oxidized for ~10 sec along with a 3"×1"×1 mm microscope glass slide (Fisher Scientific) cleaned in the same fashion as the bare Si wafer. Following oxidation, the PDMS was sealed to the microscope slide so that the fluidic network was in contact with the glass. Water was kept in the channels molded in the PDMS until experiments were run to help maintain the hydrophilic surface created by plasma oxidation.

2. DNA Hybridization

Figure 20:
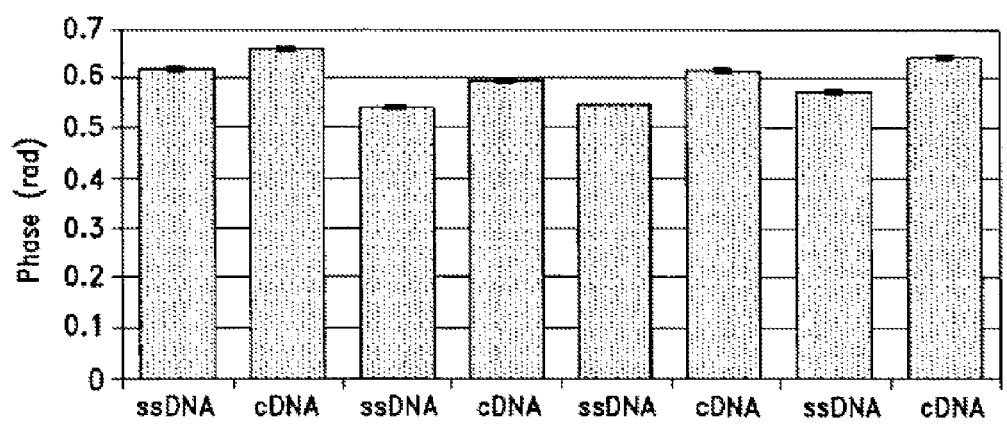
FIG. 20 shows a bar graph showing the change in absolute signal for mouse Actin DNA hybridization reactions using an OCIBD constructed in accordance with the present invention: ssDNA corresponds to a single strand DNA immobilized on the surface and PBS buffer present in the channel; cDNA corresponds to complete hybridization reaction when ssDNA and its complimentary cDNA are on the surface and PBS buffer is in the channel.
Figure 21:
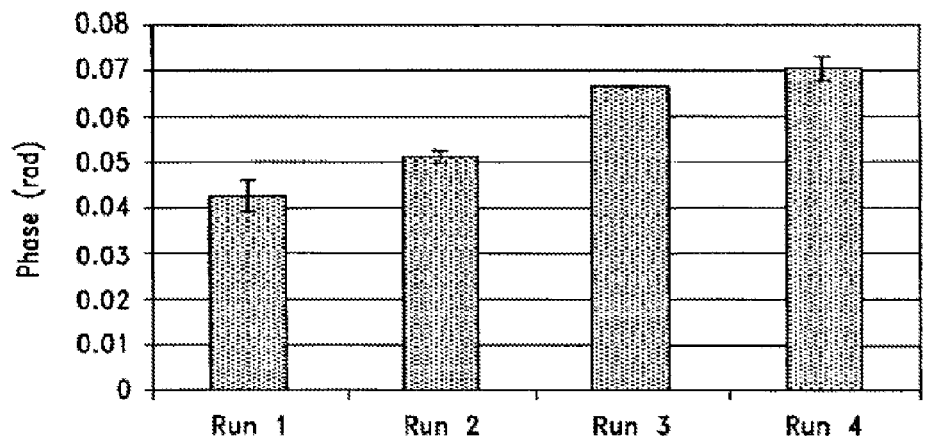
FIG. 21 shows a bar graph showing the change in the signal produced by repetitive hybridization and denaturation of mouse Actin DNA molecules immobilized on the surface. Variation in the signal between runs can be attributed to incomplete cDNA removal.

Hybridization of single stranded DNA (ssDNA) to its complimentary strand (cDNA) were performed in 50 μm×50 μm rectangular microfluidic channels molded in PDMS in the probe volume of $2.5\times10^{-10}$ L. The mouse Actin ssDNA surface immobilization was performed in three steps: first a photoactive form of biotin was deposited onto channel walls and activated with UV light; then avidin was introduced into the channel and allowed to react with immobilized photobiotin; next injected biotinalated ssDNA was allowed to react with the immobilized avidin. A 2048-element array in combination with Fourier analysis was used to quantify the positional change of the fringe pattern. The change in absolute signal due to hybridization and denaturization is shown in FIG. 20. Using the single-channel configuration of OCIBD and when reaction kinetics are not desired, the signal is recorded in two stages: a) when only ssDNA present on the channel surface and the fluid within the channel is the PBS buffer; and b) after the introduced cDNA strand has fully reacted with the immobilized ssDNA strand and after the PBS buffer has been reintroduced into the channel. This approach allows for the elimination of erroneous results due to bulk RI changes from the target species solution. From the signal magnitude of a determination, the analytical utility is demonstrated with a simple calculation. Using the parameters: Avidin dimensions of 5.6×5 nm, a probe volume of $2.5\times10^{-10}$ L, Avogadro's number, and based on the worst-case scenario assumption that 100% of the surface is covered with avidin and 100% of it is reacted with ssDNA $1.2\times10^{-16}$ mol (12 fmol) of bound DNA can be reliably detected. As shown in FIG. 21 this determination gives a result with a relatively large signal to noise (S/N) ratio. Further interrogation of the data suggests the S/N=13, so the 3σ detection limits would be 3 fmol of target DNA reacting with its counter part. These results represent an approximately two-decade improvement over SPR.

3. Interaction of calmodulin with a small molecule inhibitor

Interactions of Calmodulin (Sigma, St. Louis, Mo.) with a small molecule inhibitor, a small peptide, and a binding protein were performed in a calcium containing buffer system (i.e., 0.1 M HEPES ((4-(2-hydroxyethyl)-1-piperazineethanesulfonic acid), 0.1 M KCl, and 0.2 mM $CaCl_2$ at pH=7.5) while reactions of Calmodulin to $Ca^{2+}$ were investigated using a non-calcium containing buffer (i.e., 0.1 M HEPES, 0.1 M KCl, and 0.1 mM ethylene glycol tetraacetic acid (EGTA) at pH=7.5). The pH of buffer solutions was adjusted to the required pH by addition of 1N HCl or 1N KOH. Solutions were subsequently filtered and degassed prior to binding experiments. These experiments were conducted at 25±0.01° C. maintained by a thermoelectric temperature controller (MELCOR, Trenton, N.J.) coupled to a Peltier device. Binding experiments were monitored in real-time at frequencies ca. 50-100 Hz.

A small molecule inhibitor, trifluoperazine dihydrochloride (480 g/mol, Sigma, St. Louis, Mo.), was varied in concentration from 5-25 μM using the calcium containing Buffer prepared above. Calmodulin, held constant at 2 μM, and the inhibitor were both introduced on-chip and mixed in-line. CaM's interaction with each concentration of inhibitor was monitored and the real-time association observed.

4. Binding Kinetics of Calmodulin and M13 Peptide

The small M13 peptide used was a 17 residue (Arg-Arg-Lys-Trp-Gln-Lys-Thr-Gly-His-Ala-Val-Arg-Ala-Ile-Gly-Arg-Leu) peptide from the sequence of myosin light chain kinase. The M13 peptide, (2074.5 g/mol, Calbiochem, La Jolla, Calif.) was aliquoted into concentrations ranging from 5-50 nM using the calcium containing buffer.

Calmodulin, held constant at 5 nM, was mixed on-chip with each concentration of the M13 peptide. The kinetics of Calmodulin binding M13 peptide was monitored and recorded for later analysis.

5. Interaction of Cam and Calcineurin

The CaM and Calcineurin interactions were performed in similar conditions to those of the M13 peptide. CaM was again buffered at a pH=7.5 with 0.1M HEPES and 0.1M KCl. CaM's concentration was held constant throughout the experiment at 10 nM.

The CaM solution once more contained 0.2 mM CaCl2 to ensure CaM was in its active conformational state. The interaction of CaM with various concentrations (10-100 nM) of Calcineurin was monitored by BSI. All concentrations of Calcineurin used for the association curves were made using the same buffer prepared above and held at the same pH as CaM. The temperature was held constant at 25° C. throughout the entire experiment. A 10 nM solution of CaM and a 100 nM solution of Calcineurin both in the absence of $Ca^{2+}$ were mixed to serve as a control. The control showed <1.5% of the signal observed at the equivalent CaM and Calcineurin concentrations when $Ca^{2+}$ was present.

Calmodulin was also reacted to a small metal ion, $Ca^{2+}$. CaM was buffered at a pH=7.5 with 0.1M HEPES and 0.1M KCl with its concentration held constant throughout the experiment at 5 μM. The CaM solution contained a small amount of EGTA to chelate any free $Ca^{2+}$. BSI monitored, in real-time, the sequential reactions of 5 μM CaM with concentrations of $Ca^{2+}$ ranging from 12.5-100 μM.

6. Determination of Binding Affinity

A laser and temperature controller were powered on and allowed to equilibrate over a one hour period prior to starting the experiments. A mirror above a microfluidic chip was positioned so that the incident laser beam was directed onto a flow channel orthogonal to fluid flow. The centroid of the backscattered interference pattern was located just above the focusing lens insuring that the alignment of the system was along a central plane. A CCD array was positioned near direct backscatter in order to obtain a high-contrast fringe pattern and a dominant Fourier frequency, generally near the $5^{th}$ or $6^{th}$ fringe from the centroid.

Recorded kinetic data was analyzed according to the following derivation. Since two reactants are mixed on-chip in solution phase BSI molecular interactions, a quantitative solution to a generic, bimolecular reversible reaction was modeled by the analytical solution of a homogeneous linear first order ordinary differential equation (ODE).

Interactions of CaM and various ligands were analyzed in this manner. Observed rates determined from exponential fits of kinetic traces were plotted versus the concentrations of the various ligands. The resulting plots exhibited a linear response to concentration with coefficients of correlation ranging from 0.989 to 0.997. Equilibrium dissociation constants ($K_D$) can be determined from each graph to yield the binding affinity of each interaction.

Division of the y-intercept by the slope of each best fit line yields can then provide the desired $K_D$. The approximation of constant ligand concentration during a reaction was affirmed from the linearity of each data set and a quantitative test of the approximation performed by using the rate constants obtained from the linear least-squares results, along with the initial concentrations in the experiments, to compare the concentration of the reaction product at a specific time to the initial concentration of one of the reactants. Data analysis software can be used to determine $K_D$.

7. Free-Solution Label-Free Detection of α-Crystallin Chaperone Interactions

The binding of various protein targets by the small heat-shock protein (sHSP) α-crystallin was monitored in real time using nanoliter volumes of sample at physiologically relevant concentrations. BSI was used to monitor the kinetics and analyze the thermodynamics of interactions between α-crystallin and a model substrate, T4 lysozyme (T4L), in a label-free, tether-free format. Traditional detection methodologies including fluorescence and calorimetry were also used to cross-validate BSI. The specificity of the detection methodology was determined by comparing the interaction of αB-crystallin with two mutants of T4L having similar structures but different free energies of unfolding. Lastly, a physiologically relevant system was chosen to demonstrate the potential use of BSI in screening libraries of structural analogs and mutant constructs. Molecular interactions of a mutant α-crystallin genetically linked to autosomal dominant cataract [Mackay, D. S., Andley, U. P. & Shiels, A. Cell death triggered by a novel mutation in the alphaA-crystallin gene underlies autosomal dominant cataract linked to chromosome 21q. Eur J Hum Genet. 11, 784-93 (2003)] with another lens protein, β-crystallin, was analyzed by BSI. Quantitative kinetic and thermodynamic results from BSI were compared to the label-free, surface sensing technique SPR.

a. Method Comparison and Benchmarking of BSI

Figure 26:
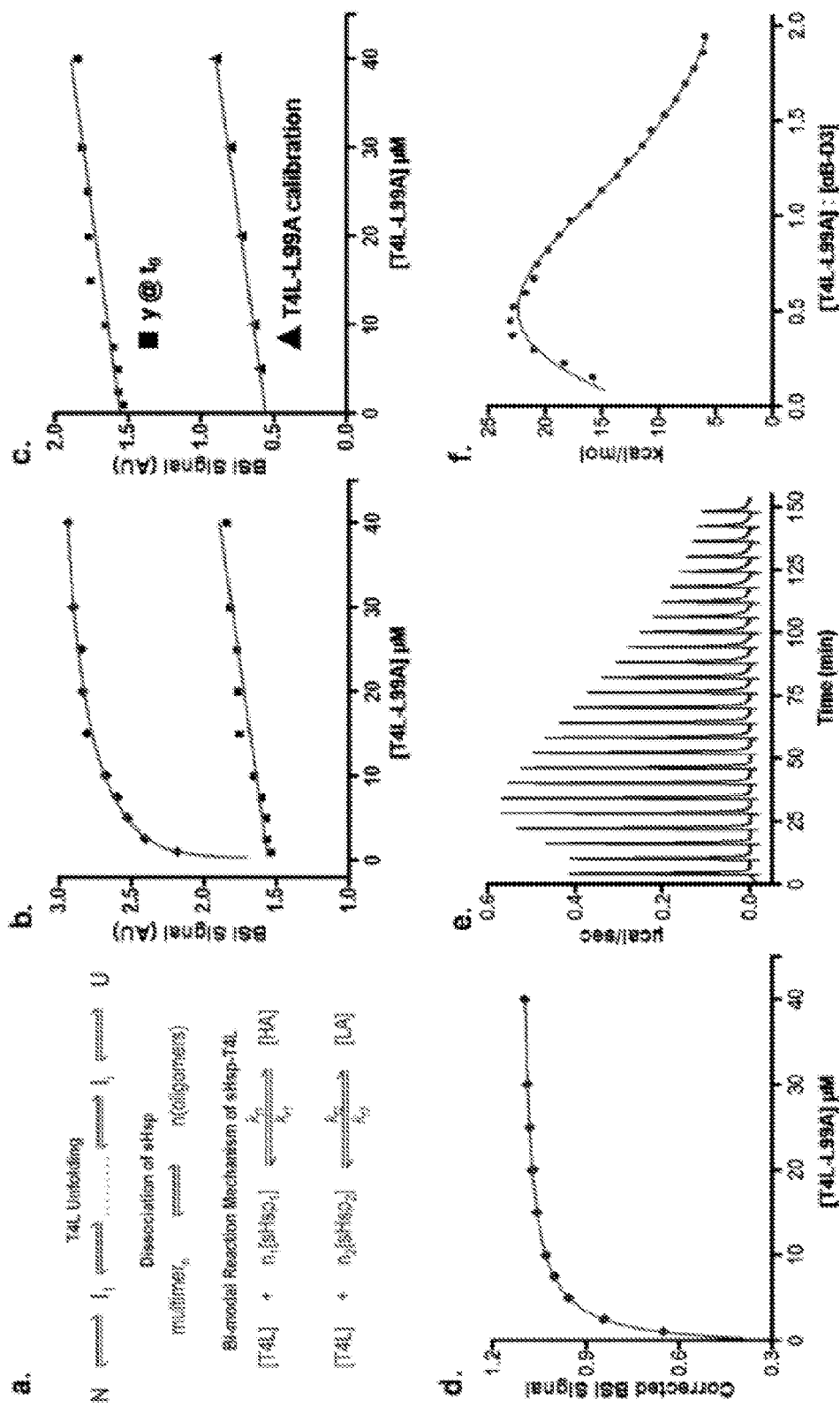
FIG. 26 shows a) equations for binding of sHSP to the substrate: (1) T4L transition from native state (N) to unfolded protein (U), (2) dissociation of the sHSP large oligomer into dimers or tetramers, and (3) formation of the sHSP/T4L complex. Steady-state BSI data (♦) shows that the magnitude of the binding signal increases with higher concentrations of T4L-L99A. The linear rise in starting values (■) reflects the response of BSI to increased concentrations of free L99A. c) The slope of the starting values of the traces in c) is identical to that obtained from direct injection of T4L without αB-D3. (d) The calibration curve was used as a baseline subtraction to obtain a corrected steady-state binding trace. Isothermal titration calorimetry (ITC) analysis αB-D3•T4L-L99A binding. (e) Heat evolved after each injection (10 μL of T4L-L99A) was detected for 25 injections. f) The area under the curve was extracted and plotted against the molar ratio to obtain a binding isotherm. Non-linear least-squares analysis was used to determine thermodynamic parameters.

The interaction of sHSP with T4L can be represented by a coupled system (FIG. 26). T4L can partially or globally unfold, occupying different energy states thus altering the affinity for sHSP binding. sHSP themselves rapidly exchange subunits and dissociate into different sized multimers that have higher affinity for substrate [Shashidharamurthy, R., Koteiche, H. A., Dong, J. & McHaourab, H. S. Mechanism of chaperone function in small heat shock proteins: dissociation of the HSP27 oligomer is required for recognition and binding of destabilized T4 lysozyme. J Biol Chem 280, 5281-9 (2005)]. Furthermore, the binding of sHSP to T4L has been shown to be bi-modal with sHSP having low and high affinity sites [Sathish, H. A., Stein, R. A., Yang, G. & McHaourab, H. S. Mechanism of chaperone function in small heat-shock proteins. Fluorescence studies of the conformations of T4 lysozyme bound to alphaB-crystallin. J Biol Chem 278, 44214-21 (2003); Shi, J., Koteiche, H. A., McHaourab, H. S. & Stewart, P. L. Cryoelectron microscopy and EPR analysis of engineered symmetric and polydisperse Hsp16.5 assemblies reveals determinants of polydispersity and substrate binding. J Biol Chem 281, 40420-8 (2006)]. Here, we compare the binding affinity determined from steady-state ITC and fluorescence analyses for a bimane-labeled T4L mutant and the B subunit of α-crystallin to that determined by BSI.

The αB-crystallin construct used in this study was a triply substituted analog of the native protein in which serine residues 19, 45, and 59 were mutated to aspartic acids. At physiological pH, the acidic residues create a triply charged αB-crystallin species that mimics phosphorylation. Referred to as αB-D3, this sHSP construct has increased affinity for non-native proteins presumably due to a shift in the equilibrium of sHSP dissociation21 (FIG. 26a). The substrate, T4L-L99A, is a mutant which has been exhaustively characterized against multiple sHSP20-24. With an alanine substituted for leucine at the hydrophobic core position 99, the buried surface area of T4L-L99A is reduced causing enlargement of preexisting cavities [Eriksson, A. E., Baase, W. A. & Matthews, B. W. Similar hydrophobic replacements of Leu99 and Phe153 within the core of T4 lysozyme have different structural and thermodynamic consequences. J Mol Biol 229, 747-69 (1993)]. The structure of T4L-L99A is nearly identical to that of the wild-type (WT) T4L with only minor rearrangement in the core. The mutation lowers the Gibb's free energy of unfolding ($\Delta G_{unf}$) by 5.1 kcal/mol relative to WT23, 24.

Upon titration with increasing T4L-L99A concentrations to a constant amount of αB-D3 (FIG. 26b), an increase in the absolute BSI signal was observed. A binding isotherm was obtained by plotting the steady-state amplitude of the BSI signal versus the concentration of T4L-L99A. This is equivalent to the fluorescence-based binding isotherms [Sathish, H. A., Stein, R. A., Yang, G. & McHaourab, H. S. Mechanism of chaperone function in small heat-shock proteins. Fluorescence studies of the conformations of T4 lysozyme bound to alphaB-crystallin. J Biol Chem 278, 44214-21 (2003)]. except that the concentration of T4L is being varied rather than sHSP. There are at least two distinguishing characteristics of the BSI isotherm. First, the end point values do not appear to reach saturation; rather, they increase linearly at high concentrations of ligand (♦—FIG. 26b). Second, a similar pattern was also observed with the starting values (■—FIG. 26b) for each αB-D3•T4L-L99A binding event. The linear increase in signal at t=0 was found to reflect increases in the free T4L concentration. This trend was not seen in previous binding assays using BSI as concentrations of the reactants used were small; therefore, changes in the amount of free ligand led to signal contributions that were near or below the sensitivity of the instrument 5. However, the span of high concentrations for the relatively large ligand, T4L (16.7 kDa), produces a linear response with increased amounts of free T4L-L99A. To confirm this interpretation, a calibration curve of T4L-L99A was constructed to detect the response of BSI to free concentrations of ligand (FIG. 26c). The slope of the calibration curve matches ($\Delta m=2.3\%$) the slope of the ascending starting values from αB-D3•T4L-L99A binding traces (y @ t0—FIG. 26c). This indicates the linear rise of end point values at high concentrations is due to an increase in free T4L-L99A. Baseline subtraction accounts for this slope in the steady-state data and was performed prior to further data analysis.

Thermodynamic analysis of binding was carried out on the baseline-corrected data using a two-mode binding model as described by Sathish, et. al [Sathish, H. A., Stein, R. A., Yang, G. & McHaourab, H. S. Mechanism of chaperone function in small heat-shock proteins. Fluorescence studies of the conformations of T4 lysozyme bound to alphaB-crystallin. J Biol Chem 278, 44214-21 (2003)]. The detected signal was modeled as arising from two components: free T4L and the sHSP•T4L complex. Binding depletes the free ligand pool and increases the contribution of the complex to the signal.

Using the two-mode binding formalism, steady-state data can be fit to obtain the dissociation constants, the number of binding sites, and the BSI signal arising from each mode. A simpler single-site binding model was also performed and served as a null hypothesis. F ratio comparison of the single and two-site binding formalisms led to a rejection of the null hypothesis at $\alpha=0.05$ signifying BSI was detecting a bi-modal molecular interaction. Further confirmation of two-mode binding was obtained from a phenomenological analysis of the real-time binding data. All kinetic traces were fit to both a single and double exponential by nonlinear least squares regression. A comparison of the square of residuals from each fitting routine confirmed the double exponential nature of the data. The observed rates, as determined from the iterative fitting process, are linear functions of L99A concentration. This dependence is predicted by the law of mass action and suggests at least two separate kinetic events are being monitored by BSI.

Thermodynamic parameters determined by BSI were compared to results obtained from ITC experiments (FIG. 26e,f) and fluorescent binding measurements in TABLE 1. The calculated low affinity dissociation constant (KD2) is very similar across platforms. However, calorimetric and fluorescence studies of high affinity binding between αB-D3 and T4L-L99A yielded close to a 20-fold increase in the equilibrium dissociation constant (KD1) when compared to BSI analysis. Without wishing to be bound by theory, it is likely that the overestimation of the affinity by BSI reflects the limited data set in the range of large molar ratios between αB-D3 and T4L in FIG. 26C. A thorough analysis using determination of forward and reverse kinetic rates yield more consistent parameters as shown below. For the purpose of this comparison, however, steady state data was exclusively used because kinetic data cannot be obtained from traditional ITC.

TABLE 1

| Data | T = 37° C. and pH = 7.2 | | |
| --- | --- | --- | --- |
| | ITC | Fluorescence | BSI |
| moles of αB-D3 used | $24 \times 10^{-9}$ | $\sim 50 \times 10^{-9}$ | $1.5 \times 10^{-9}$ |
| moles of L99A used | $54 \times 10^{-9}$ | $\sim 50 \times 10^{-9}$ | $2.93 \times 10^{-9}$ |
| $n_1$ | 0.25 | 0.24 | 0.24 |
| $K_{D1}$ (µM) | 0.015 | 0.020 | 0.001 |
| $n_2$ | 1.1 | 1.1 | 1.1 |
| $K_{D2}$ (µM) | 2.44 | 1.00 | 3.11 |

The three methods examined provide consistent levels of binding since the high affinity binding sites are saturated and low affinity binding is comparable. However, BSI analysis was carried out with considerably lower amounts of reagent. ITC and fluorescence required roughly 100 nanomoles each of sHSP and T4L, while, BSI experiments consumed nearly 20 times less. The reduced consumption of analytes is an intrinsic property of BSI and can be valuable in molecular interaction studies. Different constructs or mutated sequences often have lower expression yields, limiting the number of analyses that can be performed. In fact, the level of T4L expression for double mutants is enough to run only two experiments via ITC. The same amount of protein is sufficient for approximately forty experiments with BSI.

b. Specificity of BSI-Detected Binding: Increased α-Crystallin Affinity for Destabilized Proteins The coupled equations (FIG. 26a) predict that the affinity of sHSP to their substrates reflect the propensity of the latter to occupy non-native states. This prediction was verified for a number of sHSP using a set of T4L mutants differing in their free energy of unfolding but having similar overall structure to the native state [Matthews, B. W. Structural and genetic analysis of the folding and function of T4 lysozyme. Faseb J 10, 35-41 (1996)]. In order to establish the specificity of detection by BSI and highlight the additional kinetic dimension provided by this technique, the interaction between αB-D3 and two T4L mutants (FIG. 27a) having different free energies of unfolding. The double mutant, L99A/A130S, is the most destabilized construct of T4L with a ΔGunf equal to 3.5 kcal/mole. T4L-D70N is more stable mutant with a free energy of unfolding equal to 6.8 kcal/mol [Matthews, B. W. Structural and genetic analysis of the folding and function of T4 lysozyme. Faseb J 10, 35-41 (1996)].

Figure 27:
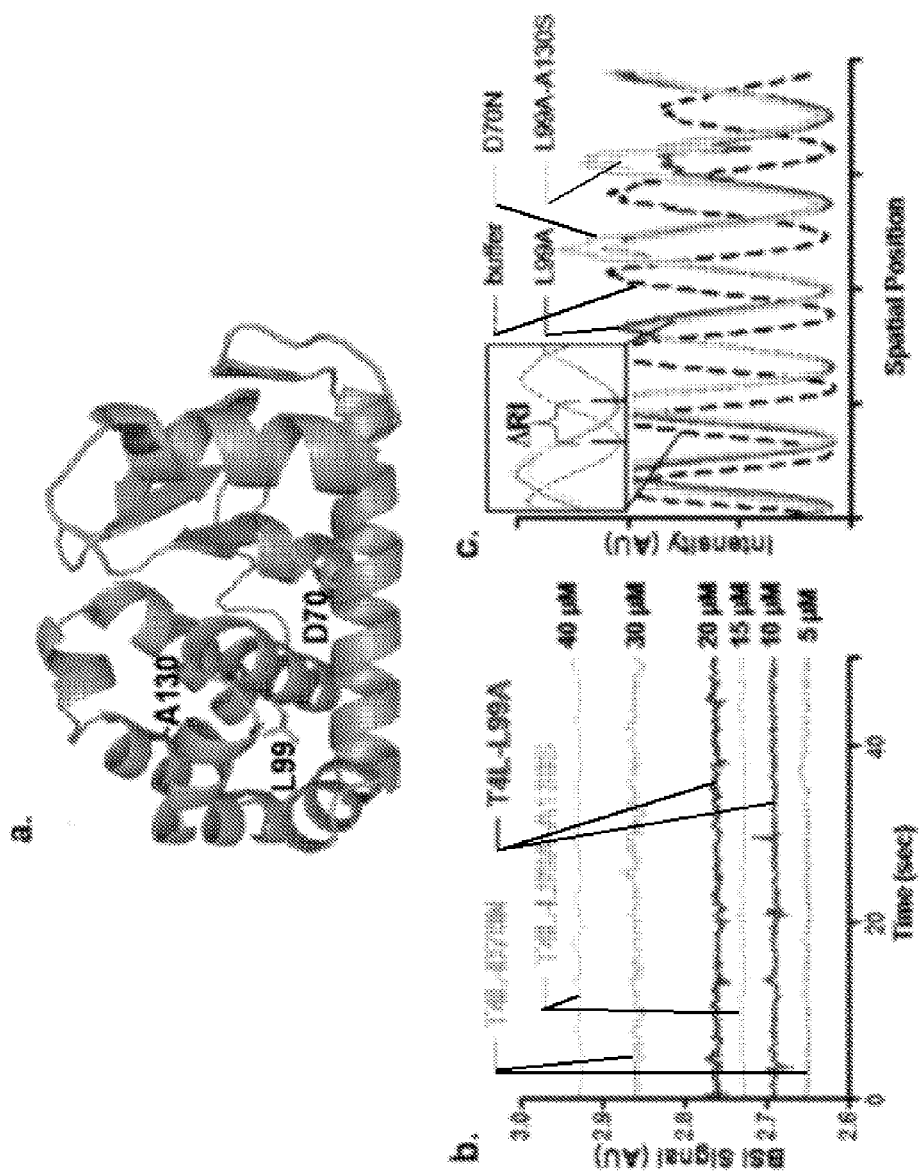
FIG. 27 shows a) the structure of T4L highlighting the sites of mutation. b) BSI signals following the injection of T4L mutants without sHSP. Increasing T4L concentration shifts the baseline but does not lead to a time-dependent change, ruling out mixing artifacts. c) Raw BSI data show an overlap in the fringe patterns of the mutants demonstrating BSI is insensitive to differences in their stabilities. A zoomed in region of the interference patterns is shown and compared to a fringe pattern from a buffer solution demonstrating the sensitivity of the instrument to changes in refractive index.

To determine if BSI is sensitive to possible mixing artifacts, mutants of T4L were mixed in channels with buffer solution and the kinetic traces of multiple concentrations recorded (FIG. 27b). With linearity of the traces approaching one, real-time data confirms that BSI signals observed in the presence of αB-D3 are not an artifact of mixing, but a true binding signal. FIG. 27c shows the interference pattern observed for each T4L mutant and the buffer solution while contained within the microfluidic channel. The zoomed-in region of the fringe pattern demonstrates the sensitivity of BSI to intrinsic refractive index, with a substantial shift seen between the interference patterns of the T4L mutants and buffer. Simultaneously, the fringe patterns produced for all T4L mutants studied precisely overlap with point-to-point minima matching Thus, differences in BSI signals for different B-crystallin/T4L-mutants must reflect changes in their interactions and not merely different BSI signals for different mutants.

Figure 28:
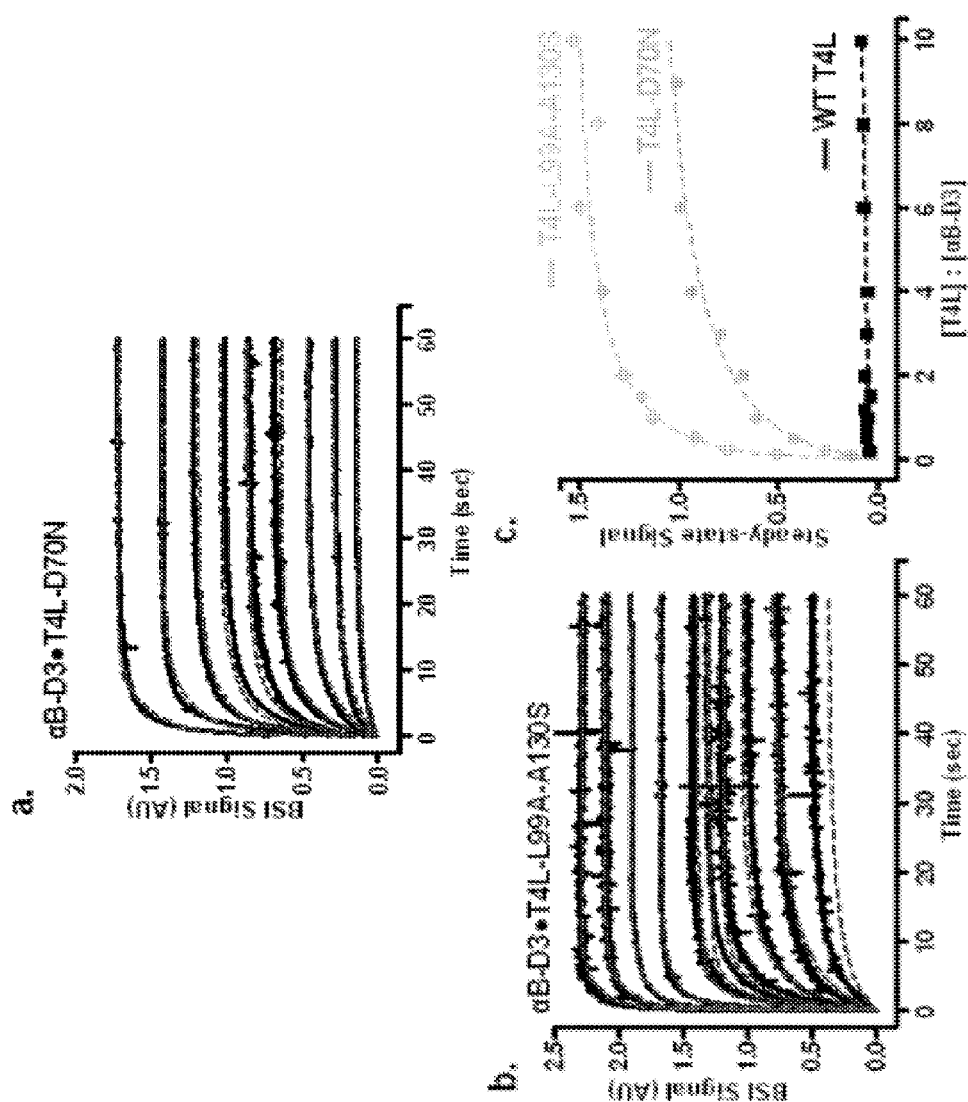
FIG. 28 shows graphs of kinetics of αB-D3 binding to T4L-D70N (a) and T4L-L99A-A130S (b) monitored by BSI (black) with kinetic traces fit via global analysis (red). Analysis of the steady-state data (c) shows that the magnitude of binding as detected by BSI for αB-D3•T4L-L99A-A130S is significantly greater than seen with αB-D3•T4L-D70N. As a control, αB-D3 was assayed against multiple concentrations of WT-T4L, exhibiting no binding across the concentration range. [T4L-D70N]=1, 2.5, 5, 10, 20, 30, 40, 60, and 90 μM. [T4L-L99A-A130S]=1, 2.5, 5, 10, 15, 20, 40, 60, 80, and 100 μM.

The association of αB-D3 with multiple concentrations of T4L was monitored in real-time by BSI analysis performed at 25° C., pH 8.0 (FIG. 28a,b). As described above, T4L calibration curves were calculated for each mutant and used for baseline subtraction of the initial starting values. Comparison of corrected steady-state data for αB-D3•T4L interactions reveals a qualitative difference between the BSI signals of each mutant (FIG. 28c). An ~40% reduction in the magnitude is observed for D70N relative to L99A/A130S at equivalent αB-D3:T4L ratios suggesting lower levels of binding. Furthermore, saturation is observed at lower molar ratios of αB-D3 to T4L for the L99A/A130S mutant. Interactions, or lack thereof, between αB-D3 and WT-T4L serve as a control. Given the larger $\Delta G_{UNF}$ of the WT, the equilibrium fraction of unfolded or non-native conformations is negligible (equation 1). Therefore marginal binding is predicted across the entire concentration range. Experimentally, BSI signals for αB-D3•T4L-WT were within the experimental noise level.

In order to quantitatively describe the kinetics of the αB-D3•T4L system observed by BSI, a more robust analysis was developed to overcome the shortcomings of the kinetic analysis performed in earlier BSI studies. Bornhop, et. al [Bornhop, D. J. et al. Free-solution, label-free molecular interactions studied by back-scattering interferometry. Science 317, 1732-6 (2007)] fit real-time traces to a single exponential regardless of the complexity of the system. This was mandated by derivation of a first order, ordinary differential equation (ODE) based on pseudo-first order kinetics under conditions of excess ligand concentration. Given the two-mode binding of T4L by α-crystallin, such a restricted parametric approach is not adequate for quantitative data analysis. Complex systems are more accurately described by higher ordered functions, generally a double exponential for interaction studies. Although extraction of multiple, highly linear rates from a single kinetic trace is feasible, considering the overall complexity of the sHSP molecular interaction system and the number of parameters corresponding to these interactions a more statistically sound approach in determining equilibrium dissociation constant(s) is needed. For instance, in the presence of molar excess of substrate, the contribution of low affinity mode to binding is marginal and the corresponding kinetic trace provides little constraints on the parameters associated with that mode.

Therefore, all the traces were fit simultaneously to one set of parameters that minimizes a global error function, $\chi^2$ Analysis of the kinetic data is based on simple rate equations derived from the binding equilibria. The time dependent BSI signal was fit to obtain forward ($k_f$) and reverse ($k_r$) rate constants. Commonly referred to as global analysis [Beechem, J. M. Expanding time scales usher in a new era for kinetic studies. Biophys J 74, 2141 (1998)], this strategy reduces the effects of instrumental artifacts in a particular kinetic trace on the final parameters and overcomes the uneven sensitivity to the parameters at either extreme of molar ratios.

Results from the global analysis of BSI experiments (TABLE 2) indicate that the affinity of αB-D3 binding in the high affinity mode increases by a factor of 4 for the more destabilized mutant, L99A/A130S. The interaction of αB-D3 with both constructs of T4L in the low affinity mode appears similar and weak for both mutants. These results clearly indicate that BSI is capable of measuring molecular interactions with high specificity, resolving binding of a sHSP to structurally homologous T4L mutants differing only in their unfolding energies. Furthermore, comparison of the data obtained from the global analysis of BSI kinetic data is consistent with previously published fluorescent analyses of the same sHSP•T4L binding systems [Koteiche, H. A. & McHaourab, H. S. Mechanism of chaperone function in small heat-shock proteins. Phosphorylation-induced activation of two-mode binding in alphaB-crystallin. J Biol Chem 278, 10361-7 (2003)].

TABLE 2

| Data | T4 Lysozyme | | |
|---|---|---|---|
| | WT | D70N | L99A-A130S |
| ?$G_{unf}$ (kcal/mol) | 14 | 9.2 | 7.9 |
| $k_{f1}$ (M$^{-1}$s$^{-1}$) | UND | 25545 | 58515 |
| $k_{-1}$ (s$^{-1}$) | UND | 1.52 × 10$^{-2}$ | 5.03 × 10$^{-6}$ |
| $K_{D1}$ | UND | 0.595 µM | 0.132 µM |
| $k_{f2}$ (M$^{-1}$s$^{-1}$) | UND | 2342 | 2970 |
| $k_{-1}$ (s$^{-1}$) | UND | 6.82 × 10$^{-2}$ | 0.115 |
| $K_{D2}$ | UND | 29.1 µM | 33.0 µM |

ID ? undetectable c. Interaction of an α-Crystallin Mutant with Another Lens Protein βB1-Crystallin The molecular targets of α-crystallin are lens proteins such as β and γ-crystallins. These proteins are long lived and undergo extensive post-translational modifications; some of which reduce the free energy of unfolding and hence are expected to trigger binding to α-crystallin. A detailed study of the energetics of α- and β-crystallin interaction via bimane fluorescence of labeled β-crystallin has been reported [McHaourab, H. S., Kumar, M. S. & Koteiche, H. A. Specificity of alphaA-crystallin binding to destabilized mutants of betaB1-crystallin. FEBS Lett 581, 1939-43 (2007)]. Results from this previous binding study demonstrate that α-crystallins have low affinity even for highly destabilized β-crystallins.

Here, BSI was used to evaluate binding of a αA-crystallin mutant genetically-linked to hereditary cataract to β-crystallin. Mackay, et. al [Mackay, D. S., Andley, U. P. & Shiels, A. Cell death triggered by a novel mutation in the alphaA-crystallin gene underlies autosomal dominant cataract linked to chromosome 21q. Eur J Hum Genet 11, 784-93 (2003)] identified a missense mutation in the HspB4 gene on chromosome 21q causing the formation of nuclear cataract. The point mutation underlying cataractogenesis was determined to be a replacement of arginine for cysteine at residue 49 (αA-R49C). αA-R49C was the first mutation found outside the conserved α-crystallin domain which gave rise to autosomal dominant cataract. Evidence from cellular studies (Mackey, et al.) suggest the deleterious effect of the mutated protein is caused by a toxic gain of function. αA-R49C was reported to have substantially higher affinity to destabilized mutants of T4L with Koteiche and Mchaourab suggesting that this mutant acts to unfold cellular proteins forming insoluble substrate-saturated complexes Koteiche, H. A. & McHaourab, H. S. Mechanism of a hereditary cataract phenotype. Mutations in alphaA-crystallin activate substrate binding. J Biol Chem 281, 14273-9 (2006)]. Furthermore, interaction of αA-R49C with thiolated substrates leads to formation of disulfide-linked α-crystallin dimers [Kumar, M. S., Koteiche, H. A., Claxton, D. P. & McHaourab, H. S. Disulfide cross-links in the interaction of a cataract-linked αA-crystallin mutant with bB1-crystallin. FEBS Lett Submitted (2008)].

To highlight the utility of BSI in monitoring native protein-protein interactions, binding studies of the cataract-linked mutant, αA-R49C, were performed with the lens protein βB1-crystallin at physiological pH and at 37° C. To mimic thiolation in the lens, βB1-crystallin was labeled with a monobromobimane probe via a disulfide linkage. Other experimental conditions and the optical setup were kept consistent with the sHSP studies described above. A similar system was studied by Kamei, et. al [Kamei, A. & Matsuura, N. Analysis of crystallin-crystallin interactions by surface plasmon resonance. Biol Pharm Bull 25, 611-5 (2002)] with the use of SPR. However, as is compulsory for SPR studies, αA-crystallin was immobilized onto a gold substrate. β-crystallin was passed over the substrate bound αA-crystallin for 25 minutes at a flow rate of 2 µL/min with changes in the local refractive index near the gold substrate used to monitor binding. In addition, regeneration of the SPR surface was accomplished by introduction of a 15 µL solution of 0.1M sodium acetate and 0.15M sodium chloride at an extreme pH of 2.3.

Figure 29:
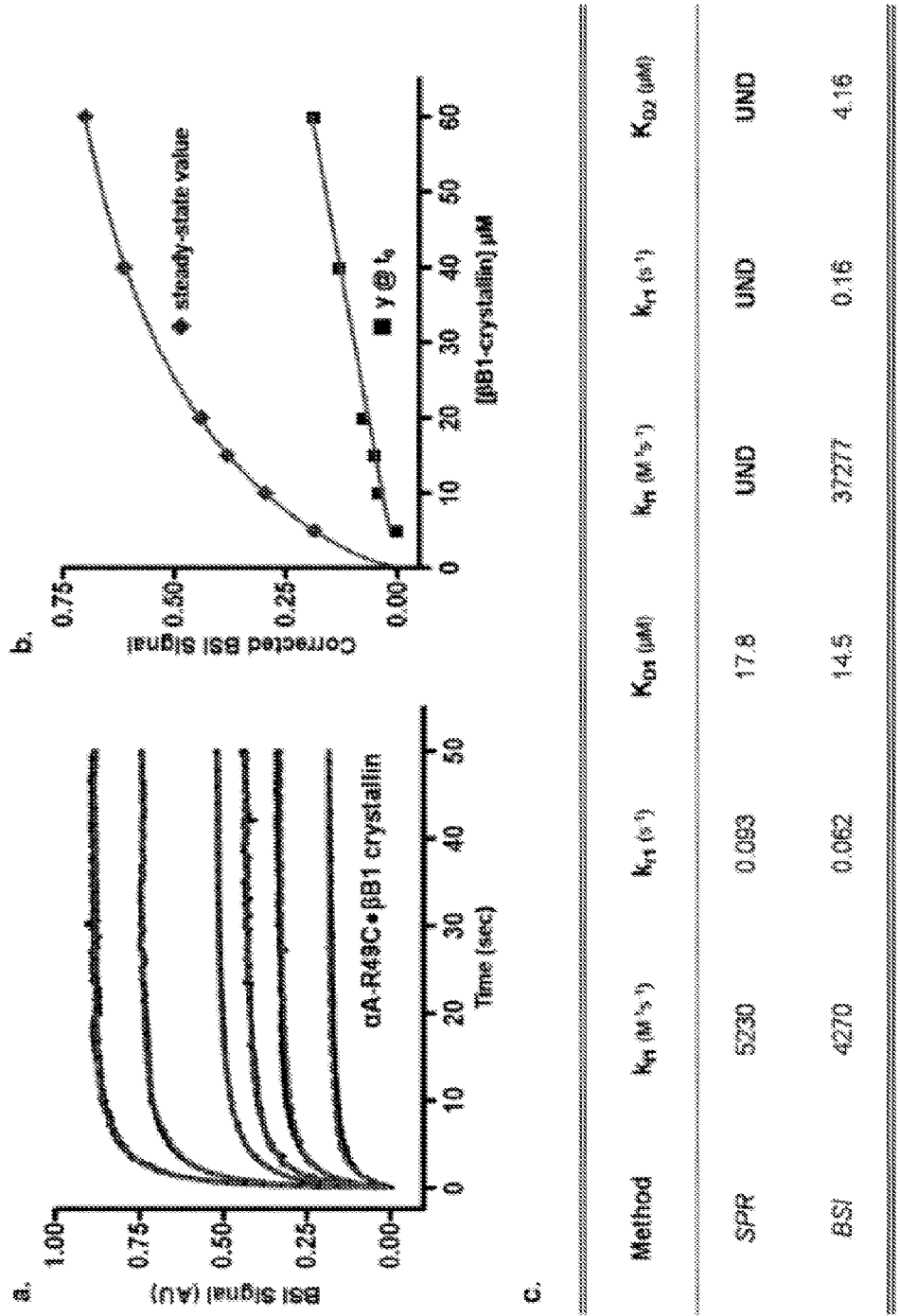
FIG. 29 shows (a) Interaction of αA-R49C-crystallin with multiple concentrations of βB1-crystallin at physiologically relevant conditions as detected by BSI. Corrected steady-state values (b) matched well with those obtained from a global analysis of the kinetic data (c).

Multiple concentrations of βB1-crystallin were assayed against a constant concentration of the mutated αA-crystallin (FIG. 29a). Global analysis was used to analyze the αA-R49C•βB1-crystallin interaction monitored by BSI. Kinetic data determined for one binding mode was quantifiable by both BSI and SPR, giving similar values for $k_f$ and $k_r$, varying by 20% and 33% respectively (FIG. 29c). However, SPR was unable to distinguish a high affinity binding mode evident in the analysis of the BSI data. The inability of SPR to detect a second rate could be due to α-crystallin being immobilized on the gold surface. BSI results for the αA-R49C•βB1-crystallin were found to be in agreement with steady-state analysis of BSI data (FIG. 29b) as well as fluorescent data published previously by Koteiche, et. al [Shi, J., Koteiche, H. A., McHaourab, H. S. & Stewart, P. L. Cryo-electron microscopy and EPR analysis of engineered symmetric and polydisperse Hsp16.5 assemblies reveals determinants of polydispersity and substrate binding. J Biol Chem 281, 40420-8 (2006)].

d. General Methods

Site-directed mutagenesis of T4L32, αA-crystallin [Berengian, A. R., Parfenova, M. & McHaourab, H. S. Site-directed spin labeling study of subunit interactions in the alpha-crystallin domain of small heat-shock proteins. Comparison of the oligomer symmetry in alphaA-crystallin, HSP 27, and HSP 16.3. J Biol Chem 274, 6305-14 (1999)], αB-crystallin [Koteiche, H. A. & McHaourab, H. S. Mechanism of chaperone function in small heat-shock proteins. Phosphorylation-induced activation of two-mode binding in alphaB-crystallin. J Biol Chem 278, 10361-7 (2003), and β-crystallin [Sathish, H. A., Koteiche, H. A. & McHaourab, H. S. Binding of destabilized betaB2-crystallin mutants to alpha-crystallin: the role of a folding intermediate. J Biol Chem 279, 16425-32 (2004)] has been described previously. Protein expression was carried out in competent BL21 (sHSP) or K38 (T4L) cell lines. Cells were transformed with mutant plasmids and cultured in Luria-Burtani (LB) broth containing small concentrations of ampicillin overnight at 32° C. This seed culture was then increased in volume and incubated for 2-3 hours at 37° C. until mid-log phase was reached. After cooling to room temperature, protein expression was induced by the addition of 0.4 mM isopropyl β-D-thioglactopyranoside (IPTG). Protein expression was carried out for 3 hours at 32° C. and 2 hours at ~30° C. post-induction for sHSP and T4L respectively.

All T4L mutants were purified by a two step separation process. Cation exchange using a Resource S column was used as an initial clean-up step. Immediately following elution, T4L mutants were labeled with monobromobimane in a 10 fold stoichiometric ratio. Reaction of the fluorophore with cysteine at position 151 was allowed to proceed overnight to ensure complete derivatization. Although neither BSI nor calorimetry require a labeled analyte for detection, all T4L mutants were fluorescently derivatized and used throughout the experiments to ensure no variability existed between the ligands used in each detection method. Labeled solutions were further purified by size exclusion chromatography using a Superdex 75 column. The eluted analyte was concentrated using Amicon® centrifugal concentrators and characterized by UV-Vis spectroscopy. Labeling efficiency was determined by monitoring absorbance peaks at 280 and 380 nm. Mutant T4L concentrations were determined by absorbance at 280 nm using an extinction coefficient of 1.231 cm2/mg.

αB-crystallin was purified in a three step separation process. αB-crystallin was loaded onto a Source Q column for anion exchange and eluted with a sodium chloride gradient. After the eluent had been adjusted to a final concentration of 0.5M ammonium sulfate, the solution was loaded onto a phenyl-Sepharose column and eluted with a gradient transitioning from 1M to 0M ammonium sulfate. A final purification step was performed by size-exclusion chromatography using a Superose 6 column. No phenyl-Sepharose column was used in the purification of β-crystallin or αA-crystallin. Following anion exchange, purified β-crystallin was reacted with a 10-fold molar excess of bimane label and incubated for 2 hours at room temperature. Excess bimane label was removed and the fluorescently labeled β-crystallin was purified by size-exclusion chromatography on a Superdex 75 column. Solutions of sHSP were concentrated using centrifugal filters and then characterized by UV-V is spectroscopy. The concentration of each sHSP construct was determined at 280 nm using the appropriate extinction coefficient.

BSI. Solutions of T4L and sHSP variants used in BSI experiments were buffered with 9 mM Tris, 6 mM MES, 500 mM NaCl, and 0.2% sodium azide. The pH of each solution was adjusted by the addition of small amounts of 5N NaOH or 5N HCl and monitored by a standard pH electrode. All solutions were filtered and degassed prior to binding experiments. Solutions were kept on ice during the experiment and briefly allowed to warm to room temperature prior to their introduction into the microchannel. The mixing chip design used was a hybrid serpentine-hydrodynamic focusing mixer as described by Bornhop, et. al [Bornhop, D. J. et al. Free-solution, label-free molecular interactions studied by back-scattering interferometry. Science 317, 1732-6 (2007)]. Experiments were maintained at the desired temperature by a MELCOR temperature controller coupled to a Peltier device. Approximately 4 µL of each sHSP and T4L construct was used in obtaining a single association curve. Binding experiments were monitored in real-time at frequencies approximately 50-100 Hz and in detection volumes on the order of picoliters.

A MicroCal VP-ITC (Isothermal Titration calorimetry) was employed to cross validate results obtained by BSI. Solutions of αB-crystallin and T4L-L99A were buffered with 0.15M Na2H2PO4, 0.1M KCl, 0.1 mM EGTA, and 0.1% sodium azide. Solutions were kept on ice before the experiment and allowed to warm near the experimental temperature prior to sample introduction. All solutions were filtered through a 0.2 micron disc and degassed before calorimetric experiments. αB-crystallin (~1.4 mL) was housed in the sample cell for ITC experiments and had an initial concentration of 12 µM. The buffer solution was kept in the reference cell. Approximately 260 µL of T4L mutant at a concentration equal to 120 µM was drawn into a syringe housed within an automated pipette system. The syringe was placed in the sample cell and spun at 300 RPM. The system was allowed to equilibrate for roughly 2 hours. Once no drift was observed in the baseline and the temperature remained fairly constant, an automated injection sequence was initiated. 10 µL of the T4L mutant was injected into the sample cell containing αB-crystallin twenty-five times with ~7 minutes allowed between injections to bring the signal back to baseline. The heat evolved after each injection was recorded and experimental data was analyzed by Origin software to calculate thermodynamic parameters for comparison to BSI and fluorescence experiments.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for free-solution determination of molecular interactions comprising the steps of:
   (a) providing a substrate having a channel formed therein for reception of a fluid sample to be analyzed;
   (b) introducing a first sample comprising a first non-immobilized analyte to be analyzed into the channel;
   (c) introducing a second sample comprising a second non-immobilized analyte to be analyzed into the channel;
   (d) allowing the first analyte to interact with the analyte to form one or more interaction products;
   (e) directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample;
   (f) detecting positional shifts in the light bands; and
   (g) determining an equilibrium constant of the interaction from the detected shifts.

2. The method of claim 1, further comprising the step of determining the formation of the one or more interaction products of the first analyte with the second analyte from the positional shifts of the light bands in the interference patterns.

3. The method of claim 1, wherein detecting positional shifts in the light bands comprises determining a change in a physical or chemical property of the fluid sample corresponding to the formation of the one more interaction products of the first analyte with the second analyte.

4. The method of claim 1, wherein the first analyte and/or the second analyte is/are unlabeled.

5. The method of claim 1, wherein the substrate further comprises a reference channel.

6. The method of claim 1, wherein the interaction is the formation of one or more covalent bonds, electrostatic bonds, hydrogen bonds, or hydrophobic interactions.

7. The method of claim 1, wherein the interaction is a binding event between small molecule-protein.

8. The method of clam 1, wherein the substrate and channel together comprise a capillary tube.

9. The method of claim 1, further comprising the step of performing a chromatographic or electrophoretic separation on the sample prior to the determining the characteristic property step.

10. The method of claim 7, wherein interaction is a binding event involving a protein associated with plasma or organelle membranes.

11. The method of claim 7, wherein the interaction is a binding event involving calmodulin.

12. A method for free-solution determination of molecular interactions comprising the steps of:
 (a) providing a substrate having a channel formed therein for reception of a fluid sample to be analyzed;
 (b) introducing a first sample comprising a first non-immobilized analyte to be analyzed into the channel;
 (c) introducing a second sample comprising a second non-immobilized analyte to be analyzed into the channel;
 (d) allowing the first analyte to interact with the second analyte to form one or more interaction products;
 (e) directing a coherent light beam onto the substrate such that the light beam is incident on the channel to generate backscattered light through reflective and refractive interaction of the light beam with a substrate/channel interface and the sample, the backscattered light comprising interference fringe patterns including a plurality of spaced light bands whose positions shift in response to changes in the refractive index of the fluid sample;
 (f) detecting positional shifts in the light bands; and
 (g) determining an end-point value of the interaction from the detected shifts.

13. The method of claim 12, further comprising the step of determining the formation of the one or more interaction products of the first analyte the second analyte from the positional shifts of the light bands in the rote interference patterns.

14. The method of claim 12, wherein detecting positional shifts in the light bands comprises determining a change in a physical or chemical property of the fluid sample corresponding to the formation of the one or more interaction products of the first analyte with the second analyte.

15. The method of claim 12, wherein the first analyte and/or the second analyte is/are unlabeled.

16. The method of claim 12, wherein the substrate further comprises a reference channel.

17. The method of claim 12, wherein the interaction is the formation of one or more covalent bonds, electrostatic bonds, hydrogen bonds, or hydrophobic interactions.

18. The method of claim 12, wherein the interaction is a binding event between small molecule-protein.

19. The method of claim 12, wherein the substrate and channel together comprise a capillary tube.

20. The method of claim 12, further comprising the step of performing a chromatographic or electrophoretic separation on the sample prior to the determining the characteristic property step.

21. The method of claim 18, wherein the interaction is a binding event involving a protein associated with plasma or organelle membranes.

22. The method of claim 18, wherein the interaction is a binding event involving calmodulin.

* * * * *

UNITED STATES PATENT AND TRADEMARK OFFICE
CERTIFICATE OF CORRECTION

PATENT NO. : 8,445,217 B2
APPLICATION NO. : 12/674610
DATED : May 21, 2013
INVENTOR(S) : Darryl J. Bornhop It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 79 days.

Signed and Sealed this
Eighth Day of September, 2015

Michelle K. Lee
*Director of the United States Patent and Trademark Office*

UNITED STATES PATENT AND TRADEMARK OFFICE
CERTIFICATE OF CORRECTION

PATENT NO. : 8,445,217 B2
APPLICATION NO. : 12/674610
DATED : May 21, 2013
INVENTOR(S) : Darryl J. Bornhop It is certified that error appears in the above-identified patent and that said Letters Patent is hereby corrected as shown below:

IN THE SPECIFICATION

In column 11, line 40, replace "$1.0 \times 10^{-1o}M$" with -- $1.0 \times 10^{-10}M$ --

In column 14, line 50, replace "$1.0 \times 10^{-1o}M$" with -- $1.0 \times 10^{-10}M$ --

In column 17, line 18 and 19, replace "photodiodc" with -- photodiode --

In column 29, line 57, replace "points d through f in Fig. 9" with -- points d through f in FIG. 9 --

In column 29, line 67, replace "points a c in Fig. 9" with -- points a through c in FIG. 9 --

In column 30, line 1, replace "d through f in FIG. 9)." with -- d through f in FIG. 9). --

In column 32, line 46, replace "25 gm" with -- 25 μm --

In column 32, line 2, replace "OD/24 um" with -- OD/24 μm --

In column 32, line 4, replace "OD/24 um" with -- OD/24 μm --

In column 32, line 5, replace "OD/24 um" with -- OD/24 μm --

In column 35, line 52, replace "to a 1.000-fold more" with -- to a 1,000-fold more --

In column 36, line 8, replace "trifluoperazinc" with -- trifluoperazine --

In column 36, line 9, replace "Calcincurin" with -- Calcineurin --

Signed and Sealed this
Twelfth Day of April, 2016

Michelle K. Lee
*Director of the United States Patent and Trademark Office*

CERTIFICATE OF CORRECTION (continued)

U.S. Pat. No. 8,445,217 B2

In column 37, line 32, replace "Sturgi II, O. M." with -- Sturgill, O. M. --

In column 39, line 18, replace "Biacorc" with -- Biacore --

In column 44, line 36, replace "BST" with -- BSI --

In column 57, line 33, replace "BST" with -- BSI --

In column 59, line 23 and 34, replace "microscalc" with -- microscale --

In column 60, line 51, replace "so the 38 detection limit" with -- so the 3δ detection limit --

In column 60, line 53, replace "2200°_C" with -- 2200_°C. --

In column 61, lines 2-3, replace "65°_C" with -- 65_°C. --

In column 62, line 2, replace "25±.01°_C" with -- 25±.01_°C. --

In column 62, line 32, replace "CaCl2" with -- $CaCl_2$ --

In column 62, line 39, replace "Ca2+" with -- $Ca^{2+}$ --

In column 69, line 17, replace "37°_C" with -- 37_°C. --

In column 69, line 20, replace "32°_C" with -- 32_°C. --

In column 69, line 21, replace "~30°_C" with -- ~30_°C. --

In column 69, line 39, replace "cm2/mg" with -- $cm^2$/mg --

In column 69, line 56, replace "UV-V is" with -- UV-Vis --

In column 70, line 53, replace "with the analyte" with -- with the second analyte --

In column 71, line 6, replace "one more interaction" with -- one or more interaction --

In column 71, line 17, replace "method of clam 1" with -- method of claim 1 --

In column 71, line 23, replace "wherein interaction" with -- wherein the interaction --

In column 72, line 12, replace "first analyte the second analyte" with -- first analyte with the second analyte --

In column 72, line 13, replace "in the rote interference" with -- in the interference --